US008206903B2

(12) United States Patent
Wang et al.

(10) Patent No.: US 8,206,903 B2
(45) Date of Patent: *Jun. 26, 2012

(54) DEVICE AND METHOD FOR ELECTROPORATION-BASED DELIVERY OF MOLECULES INTO CELLS AND DYNAMIC MONITORING OF CELL RESPONSES

(75) Inventors: Xiaobo Wang, San Diego, CA (US); Yama A. Abassi, San Diego, CA (US); Josephine Atienza, San Diego, CA (US); Xiao Xu, San Diego, CA (US); Junquan Xu, San Diego, CA (US)

(73) Assignee: Acea Biosciences, San Diego, CA (US)

( * ) Notice: Subject to any disclaimer, the term of this patent is extended or adjusted under 35 U.S.C. 154(b) by 1249 days.

This patent is subject to a terminal disclaimer.

(21) Appl. No.: 11/286,882

(22) Filed: Nov. 23, 2005

(65) Prior Publication Data

US 2006/0121446 A1 Jun. 8, 2006

Related U.S. Application Data

(63) Continuation-in-part of application No. PCT/US2005/034561, filed on Sep. 27, 2005, and a continuation-in-part of application No. 11/235,938, filed on Sep. 27, 2005, now Pat. No. 7,732,127, which is a continuation-in-part of application No. 11/197,994, filed on Aug. 4, 2005, now Pat. No. 7,468,255, which is a continuation-in-part of application No. 11/055,639, filed on Feb. 9, 2005, now Pat. No. 7,560,269, which is a continuation-in-part of application No. 10/987,732, filed on Nov. 12, 2004, now Pat. No. 7,192,752, said application No. 10/987,732 is a continuation-in-part of application No. 10/705,447, filed on Nov. 10, 2003, now Pat. No. 7,470,533, said application No. 11/235,938 is a continuation-in-part of application No. 11/198,831, filed on Aug. 4, 2005, said application No. 10/987,732 is a continuation-in-part of application No. 10/705,615, filed on Nov. 10, 2003, now Pat. No. 7,459,303.

(60) Provisional application No. 60/542,927, filed on Feb. 9, 2004, provisional application No. 60/647,159, filed on Jan. 26, 2005, provisional application No. 60/469,572, filed on May 9, 2003, provisional application No. 60/435,400, filed on Dec. 20, 2002, provisional application No. 60/633,019, filed on Dec. 3, 2004, provisional application No. 60/397,749, filed on Jul. 20, 2002, provisional application No. 60/519,567, filed on Nov. 12, 2003, provisional application No. 60/397,749, filed on Jul. 20, 2002, provisional application No. 60/469,572, filed on May 9, 2003, provisional application No. 60/613,749, filed on Sep. 27, 2004, provisional application No. 60/630,809, filed on Nov. 24, 2004, provisional application No. 60/613,872, filed on Sep. 27, 2004, provisional application No. 60/653,904, filed on Feb. 17, 2005, provisional application No. 60/630,071, filed on Nov. 22, 2004, provisional application No. 60/630,131, filed on Nov. 22, 2004, provisional application No. 60/689,422, filed on Jun. 10, 2005, provisional application No. 60/435,400, filed on Dec. 20, 2002, provisional application No. 60/673,678, filed on Apr. 25, 2005, provisional application No. 60/548,713, filed on Feb. 27, 2004, provisional application No. 60/614,601, filed on Sep. 29, 2004, provisional application No. 60/598,608, filed on Aug. 4, 2004, provisional application No. 60/630,131, filed on Nov. 22, 2004, provisional application No. 60/689,422, filed on Jun. 10, 2005, provisional application No. 60/598,609, filed on Aug. 4, 2004, provisional application No. 60/613,749, filed on Sep. 27, 2004, provisional application No. 60/647,189, filed on Jan. 26, 2005, provisional application No. 60/647,075, filed on Jan. 26, 2005, provisional application No. 60/660,829, filed on Mar. 10, 2005, provisional application No. 60/660,898, filed on Mar. 10, 2005, provisional application No. 60/630,809, filed on Nov. 24, 2004, provisional application No. 60/633,019, filed on Dec. 3, 2004, provisional application No. 60/653,904, filed on Feb. 17, 2005, provisional application No. 60/673,678, filed on Apr. 21, 2005.

(51) Int. Cl.
*C12Q 1/68* (2006.01)
(52) U.S. Cl. .......... 435/6.1; 435/461; 435/470; 435/476
(58) Field of Classification Search .................. None
See application file for complete search history.

(56) References Cited

U.S. PATENT DOCUMENTS 2,656,508 A 10/1953 Coulter
(Continued)

FOREIGN PATENT DOCUMENTS

EP 1 138 758 A1 4/2001
(Continued)

OTHER PUBLICATIONS

Wegner et al. Electric Cell-Substrate Impedance Sensing (ECIS) as a Noninvasive Means to Monitor the Kinetics of Cell Spreading to Artificial Surfaces. Experimental Cell Research 259, 158-166 (2000).

(Continued)

*Primary Examiner* — Jim Ketter
(74) *Attorney, Agent, or Firm* — Biotech Beach Law Group PC; Raymond Wagenknecht

(57) ABSTRACT

The present invention includes devices and methods for transfecting a cell or cell population and dynamic monitoring of cellular events. A variety of microelectronic devices are provide that incorporate functions such as electroporation, modulation of a transmembrane potential and dynamic monitoring of cellular functions and mechanisms.

30 Claims, 15 Drawing Sheets

U.S. PATENT DOCUMENTS

| | | | |
|---|---|---|---|
| 3,259,842 | A | 7/1966 | Coulter et al. |
| 3,743,581 | A | 7/1973 | Cady et al. |
| 3,890,201 | A | 6/1975 | Cady |
| 4,072,578 | A | 2/1978 | Cady et al. |
| 4,225,410 | A | 9/1980 | Pace |
| 4,686,190 | A | 8/1987 | Cramer et al. |
| 4,920,047 | A | 4/1990 | Giaever et al. |
| 5,001,048 | A | 3/1991 | Taylor et al. |
| 5,134,070 | A | 7/1992 | Casnig |
| 5,187,096 | A | 2/1993 | Giaever et al. |
| 5,218,312 | A | 6/1993 | Moro |
| 5,247,827 | A | 9/1993 | Shah et al. |
| 5,278,048 | A | 1/1994 | Parce et al. |
| 5,284,753 | A | 2/1994 | Goodwin |
| 5,514,555 | A | 5/1996 | Springer et al. |
| 5,563,067 | A | 10/1996 | Sugihara et al. |
| 5,601,997 | A | 2/1997 | Tchao et al. |
| 5,622,872 | A | 4/1997 | Ribi |
| 5,626,734 | A | 5/1997 | Docoslis et al. |
| 5,643,742 | A | 7/1997 | Malin et al. |
| 5,766,934 | A | 6/1998 | Guiseppi-Elie |
| 5,801,055 | A | 9/1998 | Henderson |
| 5,810,725 | A | 9/1998 | Sugihara et al. |
| 5,851,489 | A | 12/1998 | Wolf et al. |
| 5,981,268 | A * | 11/1999 | Kovacs et al. ............. 435/287.1 |
| 6,051,422 | A | 4/2000 | Kovacs et al. |
| 6,132,683 | A | 10/2000 | Sugihara et al. |
| 6,169,394 | B1 | 1/2001 | Frazier et al. |
| 6,232,062 | B1 | 5/2001 | Kayyem et al. |
| 6,235,520 | B1 | 5/2001 | Malin et al. |
| 6,280,586 | B1 | 8/2001 | Wolf et al. |
| 6,288,527 | B1 | 9/2001 | Sugihara et al. |
| 6,368,795 | B1 | 4/2002 | Hefti |
| 6,368,851 | B1 | 4/2002 | Baumann et al. |
| 6,376,233 | B1 | 4/2002 | Wolf et al. |
| 6,440,662 | B1 | 8/2002 | Gerwen et al. |
| 6,448,030 | B1 | 9/2002 | Rust et al. |
| 6,448,794 | B1 | 9/2002 | Cheng et al. |
| 6,461,808 | B1 | 10/2002 | Bodner et al. |
| 6,472,144 | B2 | 10/2002 | Malin et al. |
| 6,485,905 | B2 | 11/2002 | Hefti |
| 6,492,175 | B1 * | 12/2002 | Muller et al. ............... 435/450 |
| RE37,977 | E | 2/2003 | Sugihara et al. |
| 6,566,079 | B2 | 5/2003 | Hefti |
| 6,573,063 | B2 | 6/2003 | Hochman |
| 6,596,499 | B2 | 7/2003 | Jalink |
| 6,626,902 | B1 | 9/2003 | Kucharczyk et al. |
| 6,627,461 | B2 | 9/2003 | Chapman et al. |
| 6,630,359 | B1 | 10/2003 | Caillat |
| 6,637,257 | B2 | 10/2003 | Sparks et al. |
| RE38,323 | E | 11/2003 | Sugihara et al. |
| 6,686,193 | B2 | 2/2004 | Maher et al. |
| 6,716,620 | B2 | 4/2004 | Bashir et al. |
| 6,723,523 | B2 | 4/2004 | Lynes et al. |
| 7,192,752 | B2 | 3/2007 | Xu et al. |
| 2002/0032531 | A1 | 3/2002 | Mansky et al. |
| 2002/0076690 | A1 | 6/2002 | Miles et al. |
| 2002/0086280 | A1 | 7/2002 | Lynes et al. |
| 2002/0090649 | A1 | 7/2002 | Chan et al. |
| 2002/0110847 | A1 | 8/2002 | Baumann et al. |
| 2002/0150886 | A1 | 10/2002 | Miles et al. |
| 2003/0032000 | A1 | 2/2003 | Liu et al. |
| 2003/0072549 | A1 | 4/2003 | Facer et al. |
| 2003/0116447 | A1 | 6/2003 | Surridge et al. |
| 2003/0143625 | A1 | 7/2003 | Martin et al. |
| 2003/0157587 | A1 | 8/2003 | Gomez et al. |
| 2003/0166015 | A1 | 9/2003 | Zarowitz et al. |
| 2004/0091397 | A1 | 5/2004 | Picard |
| 2004/0146849 | A1 | 7/2004 | Huang et al. |
| 2005/0014130 | A1 | 1/2005 | Liu et al. |

FOREIGN PATENT DOCUMENTS

| | | |
|---|---|---|
| EP | 1195432 B1 | 9/2004 |
| WO | 96/01836 | 1/1996 |
| WO | 99/66329 | 12/1999 |
| WO | WO 0037628 A1 * | 6/2000 |
| WO | 00/71669 | 11/2000 |
| WO | 01/25769 | 4/2001 |
| WO | 01/38873 | 5/2001 |
| WO | 02/04943 | 1/2002 |
| WO | 02/42766 | 5/2002 |
| WO | 03/016887 | 2/2003 |
| WO | 2005/005979 | 1/2005 |

OTHER PUBLICATIONS

Mohr et al., Performance of a thin film microelectrode array for monitoring electrogenic cells in vitro, Sensors and Actuators B34:265-269. 1996.
Aravanis et al. Biosensors & Bioelectronics 16:571-577 (2001).
Baumann et al. Sensors & Accuators B55:77-89 (1999).
Becker et al, Cell Biology. 92:960-964 (1995).
Berens et al, Clin. Exp. Metastasis 12:405-415 (1994).
Bergveld, Biosensors & Bioelectronics. 6:55-72 (1991).
Bieberich and Guiseppi-Elie, Biosensors and Bioelectronics, 19:923-931 (2004).
Burnett et al., J. Biomo. Screening, 8(6):660-667 (2003).
Burns et al, Journal of Immunology 2893-2903 (1997).
Ciambrone et al., J. Biomo. Screening, 9(6):467-480 (2004).
Connolly et al, Biosensors & Bioelectronics 5: 223-234 (1990).
Duan et al, Anal. Chem. 66:1369-1377 (1994).
Ehret et al, Biosensors and Bioelectronics 12(1):29-41 (1997).
Ehret et al, Medical & Biological Engineering and Computing 36:365-370.
Falk et al, J. Immunol. Meth. 33:239-247 (1980).
Fuhr et al, Sensors and Materials 7(2):131-146 (1995).
Gaiever et al, Proc. Natl. Acad. Sci 81:3761-3764 (1984).
Giaever et al, Proc. Natl. Acad. USA 88: 7896-7900 (1991).
Gutmann et al, Pharmaceutical Research, 16(3):402-407 (1999).
Hadjout et al., BioTechniques 31: 1130-1138 (2001).
Henning et al, Anti-Cancer Drugs 12:21-32 (2001).
Hidalgo et al, Gastroenterology 96:736-749 (1989).
Huang et al, Anal. Chem. 74:3362-3371 (2002).
Hug, Assay and Drug Dev. Tech., 1(3):479-488 (2003).
Keese et al, Biotechniques 33:842-850 (2002).
Kleinmann et al, Biochemistry. 26:312-318 (1986).
Kowolenko et al, Journal of Immunological Methods 127: 71-77 (1990).
Larsen et al, Micro Total Analysis Systems 103-106 (2000).
Lin and Huang, J. Micromech. Microeng., 11:542-547 (2001).
Lin et al., Min. for Chem., Bio., & Bioeng., 4:104-108 (2004).
Lo et al, Experimental Cell Research 204:102-109 (1993).
Lo et al, Experimental Cell Research 213: 391-397 (1994).
Lo et al, Biophysical Journal 69: 2800-2807 (1995).
Loffert et al., QIAGENNews, 4:15-18 (1997).
Luong, et al, Analytical Chemistry 73: 1844-1848 (2001).
Mitra et al, Biotechniques 11(4):504-510 (1991).
Miyata et al, Jpn. J. Ophthalmol. 34:257-266 (1990).
Nerurkar et al, Pharmaceutical Research 13(4):528-534 (1996).
Ong et al, Sensors 2:219-222 (2002).
Pancrazio et al, Sensors and Actuators B 53:179-185 (1998).
Yang et al, Anal. Chem. 71:911-918 (1999).
New Products page. Science 298:2409 (2002).
Abstract: Real-Time Impedance Assay to Follow the Invasive Activities of Metastatic Cells in Culture. Biotechniques 33: 842 (2002).
Blagbrough et al., Polyamines and novel polyamine conjugates interact with DNA in ways that can be exploited in non-viral gene therapy, Biomed. Soc. Trans. 2003;31(2):397-406.
Bonetta, The inside scoop-evaluating gene delivery methods, Nature Methods 2005;2(11):875-883.
Hapala, Breaking the Barrier: Methods for Reversible Permeabilization of Cellular Membranes 1997;17(2):105-133.
Nicolazzi et al., Cationic Lipids for Transfection, Curr. Med. Chem, 2003;10:1263-1277.

* cited by examiner

A
B

DEVICE AND METHOD FOR ELECTROPORATION-BASED DELIVERY OF MOLECULES INTO CELLS AND DYNAMIC MONITORING OF CELL RESPONSES

CROSS REFERENCE TO RELATED APPLICATIONS

This application is a continuation-in-part of PCT patent application serial number PCT/US05/34561 filed on Sep. 27, 2005 and a continuation-in-part of U.S. patent application Ser. No. 11/235,938 entitled, "Dynamic Monitoring of Cell Adhesion and Spreading Using the RT-CES System", filed on Sep. 27, 2005 now U.S. Pat. No. 7,732,127 which is a continuation in part of U.S. patent application Ser. No. 11/197,994 entitled, "Method for Assaying for Natural Killer, Cytotoxic T-Lymphocyte and Neutrophil-Mediated Killing of Target Cells Using Real-Time Microelectronic Cell Sensing Technology", filed on Aug. 4, 2005 now U.S. Pat. No. 7,468,255, which is a continuation-in-part of U.S. patent application Ser. No. 11/055,639, entitled "Real time electronic cell sensing system and applications for cytotoxicity profiling and compound assays" filed on Feb. 9, 2005 now U.S. Pat. No. 7,560,269 which is a continuation-in-part of U.S. patent application Ser. No. 10/987,732, entitled "Real time electronic cell sensing system and application for cell based assays" filed on Nov. 12, 2004 now U.S. Pat. No. 7,192,752, which claims priority from U.S. provisional application Ser. No. 60/519,567, filed on Nov. 12, 2003. All applications referred to in this paragraph are incorporated by reference in their entireties herein.

Parent U.S. patent application Ser. No. 10/987,732 is itself a continuation-in-part of U.S. patent application Ser. No. 10/705,447 filed on Nov. 10, 2003 now U.S. Pat. No. 7,470,533, entitled "Impedance Based Devices and Methods for Use in Assays" which claims priority to U.S. provisional patent application Ser. No. 60/397,749, filed on Jul. 20, 2002; U.S. provisional patent application Ser. No. 60/435,400, filed on Dec. 20, 2002; U.S. provisional patent application Ser. No. 60/469,572, filed on May 9, 2003; and PCT patent application serial number PCT/US03/22557, filed on Jul. 18, 2003. All of the applications referred to in this paragraph are incorporated by reference in their entireties herein.

Parent U.S. patent application Ser. No. 11/235,938 also claims benefit of priority to U.S. provisional patent application Ser. No. 60/630,131, filed on Nov. 22, 2004; U.S. provisional patent application Ser. No. 60/630,071 filed on Nov. 22, 2004; U.S. provisional patent application Ser. No. 60/613,872 filed on Sep. 27, 2004; U.S. provisional patent application Ser. No. 60/613,749, filed on Sep. 27, 2004; U.S. provisional patent application Ser. No. 60/630,809 filed on Nov. 24, 2004; U.S. provisional patent application Ser. No. 60/633,019 filed on Dec. 3, 2004; U.S. provisional patent application Ser. No. 60/647,159 filed on Jan. 26, 2005; U.S. provisional patent application Ser. No. 60/653,904 filed on Feb. 17, 2005; and U.S. provisional patent application Ser. No. 60/673,678 filed on Apr. 25, 2005; U.S. provisional patent application Ser. No. 60/689,422 filed on Jun. 10, 2005; PCT patent application serial number PCT/US05/27943 filed on Aug. 4, 2005 and PCT patent application serial number PCT/US05/27891 filed on Aug. 4, 2005. All of which are incorporated by reference in their entirety.

Parent U.S. patent application Ser. No. 11/235,938 is also a continuation-in-part of U.S. patent application Ser. No. 11/198,831, entitled, "Dynamic Monitoring of Activation of G-Protein Coupled Receptor (GPCR) and Receptor Tyrosine Kinase (RTK) in Living Cells using Real-Time Microelectronic Cell Sensing Technology, filed on Aug. 4, 2005, which is herein incorporated by reference in its entirety.

Parent U.S. patent application Ser. No. 10/987,732 is also a continuation-in-part of U.S. patent application Ser. No. 10/705,615, entitled "Impedance Based Apparatuses and Methods for Analyzing Cells and Particles", filed on Nov. 10, 2003, now U.S. Pat. No. 7,459,303 which claims priority to U.S. provisional patent application Ser. No. 60/397,749 filed on Jul. 20, 2002; U.S. provisional patent application Ser. No. 60/435,400, filed on Dec. 20, 2002; U.S. provisional patent application Ser. No. 60/469,572, filed on May 9, 2003; and PCT patent application serial number PCT/US03/22537, filed on Jul. 18, 2003. All of the applications referred to in this paragraph are incorporated by reference in their entireties herein.

Parent U.S. patent application Ser. No. 11/055,639 also claims priority to U.S. provisional patent application Ser. No. 60/542,927 filed on Feb. 9, 2004; U.S. provisional patent application Ser. No. 60/548,713, filed on Feb. 27, 2004, and U.S. provisional patent application Ser. No. 60/614,601, filed on Sep. 29, 2004. All of the applications referred to in this paragraph are incorporated by reference in their entireties herein.

Parent U.S. patent application Ser. No. 11/197,994 is also a continuation-in-part of PCT patent application serial number PCT/US05/04481, filed on Feb. 9, 2005, which is a continuation-in-part of PCT patent application serial number PCT/US04/37696, filed on Nov. 12, 2004. All of the applications referred to in this paragraph are incorporated by reference in their entireties herein.

Parent U.S. patent application Ser. No. 11/197,994 also claims priority to U.S. provisional patent application Ser. No. 60/598,608, filed on Aug. 4, 2004, U.S. provisional patent application Ser. No. 60/630,131, filed on Nov. 22, 2004, U.S. provisional patent application Ser. No. 60/689,422, filed on Jun. 10, 2005, U.S. provisional patent application Ser. No. 60/598,609, filed on Aug. 4, 2004, U.S. provisional patent application Ser. No. 60/613,749, filed on Sep. 27, 2004, U.S. provisional patent application Ser. No. 60/647,189, filed on Jan. 26, 2005, U.S. provisional patent application Ser. No. 60/647,075, filed on Jan. 26, 2005, U.S. provisional patent application Ser. No. 60/660,829, filed on Mar. 10, 2005, and U.S. provisional patent application Ser. No. 60/660,898, filed on Mar. 10, 2005. All of the applications referred to in this paragraph are incorporated by reference in their entireties herein.

This application also claims benefit of priority to U.S. provisional patent application Ser. No. 60/630,809, filed on Nov. 24, 2004; U.S. provisional patent application Ser. No. 60/633,019 filed on Dec. 3, 2004; U.S. provisional patent application Ser. No. 60/653,904 filed on Feb. 17, 2005; and U.S. provisional patent application Ser. No. 60/673,678 filed on Apr. 21, 2005. All of the applications referred to in this paragraph are incorporated by reference in their entireties herein.

TECHNICAL FIELD

The present application relates to microelectronic devices and methods of use of to detect changes in impedance of a cell, and more specifically to microelectronic devices for electroporation-based delivery of molecules into cells and dynamic monitoring of cellular responses and microelectronic devices for monitoring the effects of compounds on voltage gated ion channels and methods of use.

BACKGROUND

The mapping and sequencing of the human genome will probably be one of the most remarkable achievements of the 21st century. This effort, led by the Human Genome Project has created an unprecedented opportunity to characterize and understand the function of the repertoire of newly discovered genes at the individual gene level and the complexities in the interaction of the gene products at the organism level (Austin, C. P, 2004, Annu. Rev. Med. Vol. 55, pp 1-13). Only when this task is truly achieved and understood can the scientific community deliver on the promise of the Human Genome Project for blockbuster drugs and targeted therapy for different ailments afflicting mankind (Austin, C. P, 2004, Annu. Rev. Med. Vol. 55, pp 1-13).

The task of functional characterization of newly discovered genes is initiated by the introduction of plasmids containing a copy of the gene of interest into mammalian cells so that its function can be assessed in an appropriate cellular context such as proliferation, viability, gene expression and differentiation amongst others (Kramer, R. and Cohen D., 2004, Nat. Rev. Drug Discov. Vol. 3, pp 965-972). Alternatively, dominant negative versions of the gene of interest which interfere with the function of the wildtype gene or reagents which down regulate gene expression such as antisense oligonucleotides or interfering RNA (RNAi) can also be introduced into mammalian cells and its impact assessed in various cell-based assays described above (Kramer, R. and Cohen D., 2004, Nat. Rev. Drug Discov. Vol. 3, pp 965-972). Regardless of the approach taken the main hurdle in introducing these reagents into the cell is the penetration of the plasma membrane lipid bilayer. First of all, the plasma membrane lipid bilayer is fairly impervious to most molecules of biologic and medical interest. Moreover, the fact that the lipid bilayer can vary significantly in terms of its polar lipid, protein, glycoprotein and carbohydrate composition from cell type to cell type poses a significant and arduous challenge in introducing various macromolecules into the cells in a systematic manner.

A number of chemical, physical and biological techniques have been devised for introducing macromolecules such as DNA and RNA into mammalian cells. The most widely used method encompasses lipid-mediated transfection which works well for some cell types but not others in particular primary cells and immune cells (Liu, D., Ren, T., and Gao, X., 2003, Curr. Med. Chem. Vol. 10, pp 1307-1315; Nicolazzi, C., Garinot, M., Mignet, N., Scherman, D. and Bessodes, M. 2003, Curr. Med. Chem., Vol. 10, pp 1263-1277). In addition, a number of cells are extremely sensitive to lipid-mediated transfection and there can be significant degree of cytotoxicity associated with this method. Amine-based transfection is another technique that has been utilized for transfection (Blagbrough, I. S., Geall, A. J. and Neal, A. P., 2003, Biochem. Soc. Trans, Vol. 31, pp 397-406). However, it is also prone to the same challenges as lipid-mediated transfection. Another method for introduction of macromolecules into mammalian cells is based on microinjection where a specially designed microcapillary needles are used in conjunction with a micromanipulator apparatus and a microscope (Lamb, N. J., Gauthier-Rouviere, C. m and Fernandez, A. 1996, Front Biosci. Vol. 1, pp 19-29). While, this method is fairly efficient specially for hard to transfect cells such as primary cells and neurons (Washbourne, P. and McAllister, A. K., 2002, Curr Opin Neurobiol. Vol. 12, pp 566-573), its wide scale use has been restricted due to its technical hurdle as well as its throughput and at this moment in time is certainly not feasible for genome-scale procedures. Viral-mediated gene transfer is another method of introducing DNA and RNA into mammalian cells (Hapala, I., 1997, Crit. Rev. Biotechnol. Vol. 17, pp 105-122). Several different systems such as adenovirus and vaccinia virus systems have been successfully used for efficient transfection of mammalian cells, especially neuronal cells. While viral system may work efficiently at the level of single genes, it utility at genome-wide scale is significantly compromised due to the time it takes for construction of viral vectors and for obtaining optimal viral titers for infection. In summary, while a number of procedures have been optimized for transfection and some have been used for genome-wide introduction of genes and RNAi into mammalian cells, none of the procedures discussed are optimal for high throughput, efficient and reproducible introduction of macromolecules into mammalian cells. There is a need to develop a novel, efficient, and reproducible method that can introduce and deliver molecules to cells.

Subsequent to cellular transfection of macromolecules by various means, the effect of the macromolecule(s) are analyzed in the appropriate cellular context by different end-point assays. These end-point assays can only provide information about the cellular effects of the macromolecule transfected only at a specific time point. In addition, these assays typically are applicable to only a single cellular event that is to be analyzed.

U.S. Pat. No. 6,686,193 disclosed instrumentation and methods for screening drug candidate compounds with activity against ion channel targets. The method included modulating the transmembrane potential of host cells in a plurality of sample wells with a repetitive application of electrical fields so as to set the transmembrane potential to some target levels. A number of devices were disclosed. However, the devices had limitations in delivering effective electrical fields to population of cells in the wells.

In a publication by Burnett et al ("Fluoresence Imaging of Electrically Stimulated Cells", by P Burnett, J K Robertson, J M Palmer, R R Ryan, A E Dubin and R A Zivin, in Journal of Biomolecular Screening, volume 8 (6), 2003, pp 660-667), the authors described some preliminary results obtained from devices that were designed to supply electrical stimuli to population of cells. Using a digital fluorescent microscope, changes in voltage-gated ion channel activity were monitored. As an example, a device with an interdigitated electrode fingers were used to electrically stimulate cells. However, these techniques have not been successfully coupled to a real time electronic cell sensing system.

SUMMARY

In one aspect of the present invention a method of monitoring a cellular response in real time is provided including transfecting a cell or cell population with a molecule or molecules; and monitoring impedance of said cell or said cell population. Examples of cell transfection may include chemical transfection methods, electroporation, thermal transfection methods and viral transfection methods. Non-limiting examples of chemical transfection methods include lipid-mediated transfection method and amine-based transfection method. Electroporation methods may include applying a sine wave, a square wave or a waveform following an exponential decay. Molecules for electroporation into a cell or cell population include nucleic acid molecules, DNA molecules, RNA molecules, RNAi molecules and siRNA molecules, microRNA molecules, native RNA molecules, ribozyme RNA molecules, aptamers, plasmids, cDNA molecules, antisense DNA strands, oligonucleotides, oligopeptides, polypeptides, proteins and organic compounds. The methods will have particular utility to eukaryotic cells including human cells. Also are included molecules capable of affecting transcription, translation, RNA splicing, RNA editing or a cellular function such as cell proliferation, cell adhesion, and cell spreading. The molecule is capable of affecting cell morphology, a cellular receptor or a signal transduction pathway that is activated by a cellular receptor.

Impedance monitoring may be performed by conducting a series of impedance measurements and optionally determining a change in impedance for cells prior to and after transfection with molecules. The impedance of control cells can also be monitored. Control cells may refer to cells that are transfected with control molecules using the same transfection method as that for the test cells. Control molecules are molecules that do not have direct effects on cellular functions that are being tested. Control cells may also refer to cells that are not transfected with any molecules. Control cells may also refer to cells that are transfected with molecules of interest with different transfection method. A cell index or normalized cell index may also be determined. The cell or cell index may be compared at different time points within the same cell or cell population or may be compared between cells or cell populations.

In the present application, monitoring of impedance of cell or cell population may be performed prior to transfection of cells with molecules, or after transfection of cells with molecules, or prior to and after transfection of cells with molecules. Impedance monitoring is used as a method to assess cell proliferation, cell growth, cell death, cell morphology, cell membrane properties (for example, size, morphology, or composition of the cell membrane) cell adhesion, cell spreading and/or cell motility and to assess the effects of transfected molecules in cells on cell proliferation, cell growth, cell death, cell morphology, cell membrane properties (for example, size, morphology, or composition of the cell membrane) cell adhesion, cell spreading and/or cell motility. Thus the assays in the present application can be cytotoxicity assays, proliferation assays, apoptosis assays, cell adhesion assays, cell activation or stimulation assays, anti-cancer compound efficacy assays, receptor-ligand binding or signal transduction analysis, assays of cytoskeletal changes, assays of cell structural changes (including but not limited to, changes in cell membrane size, morphology, or composition), cell quantification, cell quality control, time-dependent cytotoxicity profiling, assays of cell differentiation or de-differentiation, detection or quantitation of neutralizing antibodies, specific T-cell mediated cytotoxic effect assays, assays of cell adhesion or spreading, assays of cell-cell interactions, analysis of microbial, viral, or environmental toxins, etc.

In some embodiments, impedance measurements are used in conjunction with an end point assays such as a cell viability assay, apoptosis assay, enzymatic assay, signal transduction analysis assay, or a reporter assay. An impedance measurement may be used as a guide to determine the time for performing an endpoint assay. For example, the end-point assay may not be conducted until the time-dependent impedance of cells meets certain criteria. In some embodiments, such criteria may include that the impedance has to be above certain threshold values, within certain ranges, and below certain threshold values. In some other embodiments, such criteria may refer that the impedance of cells passes a minimum or maximum along the time dependent course. For example, the time-dependent impedance may initially decrease with time until reaching a minimum, then increase with time after the minimum. In this example, the end-point assay may be conducted immediately after the impedance has passed the minimum point.

Cells or cell populations may be electroporated and monitored in the same device or a different device. Impedance may be monitored prior to, after or both prior to and after electroporation. Impedance monitoring may include a series of impedance. A predetermined threshold or range of impedance may be required prior to electroporating a cell or cell population.

In another aspect of the present invention a method of monitoring the effect of a compound on an ion channel is provided including providing a device capable of monitoring impedance of a cell or cell population and capable of inducing a change in a cell membrane potential; adding a cell or cell population comprising a voltage gated ion channel to the device; adding a test compound to the device; inducing a change in a cell membrane potential; and monitoring the impedance. Monitoring the impedance may be conducted before, during, after, or before and during and after adding the test compound the device. Monitoring the impedance may be conducted before and after inducing the change in cell membrane potential. The cell or cell population may further be monitored optically or by other means to measure cell membrane potential or other ion-channel activity associated parameters before and after inducing a change in cell membrane potential. In an exemplary embodiment, monitoring cell membrane potential is performed using an optical detection method after an optically detectable compound is added to the device. For example, a cell or cell population may be observed by detecting a membrane-potential-sensitive fluorescent dye added to the cell or cell population. Assessing or measuring cell membrane potential or other ion-channel activity-associated parameters may be performed at the same time as, or different times from, monitoring the impedance of cell population. The change in membrane potential may open or close a voltage gated ion channel. A cell index or normalized cell index may be determined and may be compared to the same cell or cell population or may be compared between different cells or cell populations.

In another aspect of the present invention a device for monitoring a cell or cell population is provided including a nonconductive substrate; a plurality of electrode arrays positioned on the substrate, wherein each electrode array includes at least two electrodes, further wherein each electrode is separated from at least one adjacent electrode by an area of non-conductive material; and at least one set of electroporation or electrostimulation electrodes, the electroporation or electrostimulation electrodes are capable of electroporating a cell or cell population or affecting the membrane potential of a cell. The change in membrane potential may result in opening or closing of a voltage gated ion channel. In some embodiments, a first half of the electroporation or electrostimulation electrodes may be in the plane of the substrate and a second half of the set of electrodes may be outside the plane of the substrate. In some embodiments, the nonconductive substrate is a porous substrate that is located above one half of the at least one set of electroporation or electrostimulation electrodes.

In some embodiments, the device includes a plate including multiple wells, further wherein at least one of the multiple wells includes a top, bottom and sidewall, further wherein the bottom and the sidewall are constructed from the nonconductive substrate, further wherein the plurality of electrode arrays are positioned at the bottom, further wherein a first half of the at least one set of electroporation or electrostimulation electrodes are positioned at the bottom and a second half of the at least one set of electroporation or electrostimulation electrodes are positioned at the top. The electroporation or electrostimulation electrodes at the top may take the form of a disc electrode or an electrical wire. Examples include a device having a 96 well, a 384 well or 1536 well configuration, which may have dimensions and footprint same as those of standard microtiter plates. The multiple wells are capable of electroporating or electrostimulating cells together or separately. In some embodiments, the plate is capable of stacking on top of a second plate.

In another aspect of the present invention, a method of identifying an ion channel inhibitor is provided including providing a microelectronic cell sensor array operably connected to an impedance analyzer, the microelectronic cell sensor array including a non-conductive substrate, a plurality of electrode arrays positioned on the substrate, each electrode array including at least two electrodes, and each electrode is separated from at least one adjacent electrode by an area of non-conductive material. The device is capable of affecting the membrane potential in a cell or cell population such that a voltage gated ion channel may open or close. A suspected inhibitor is added to a cell or cell population, the membrane potential is affected and the cell or cell population is monitored to determine whether a voltage gated ion channel has opened or closed.

DETAILED DESCRIPTION

A. Definitions

Figure 1:
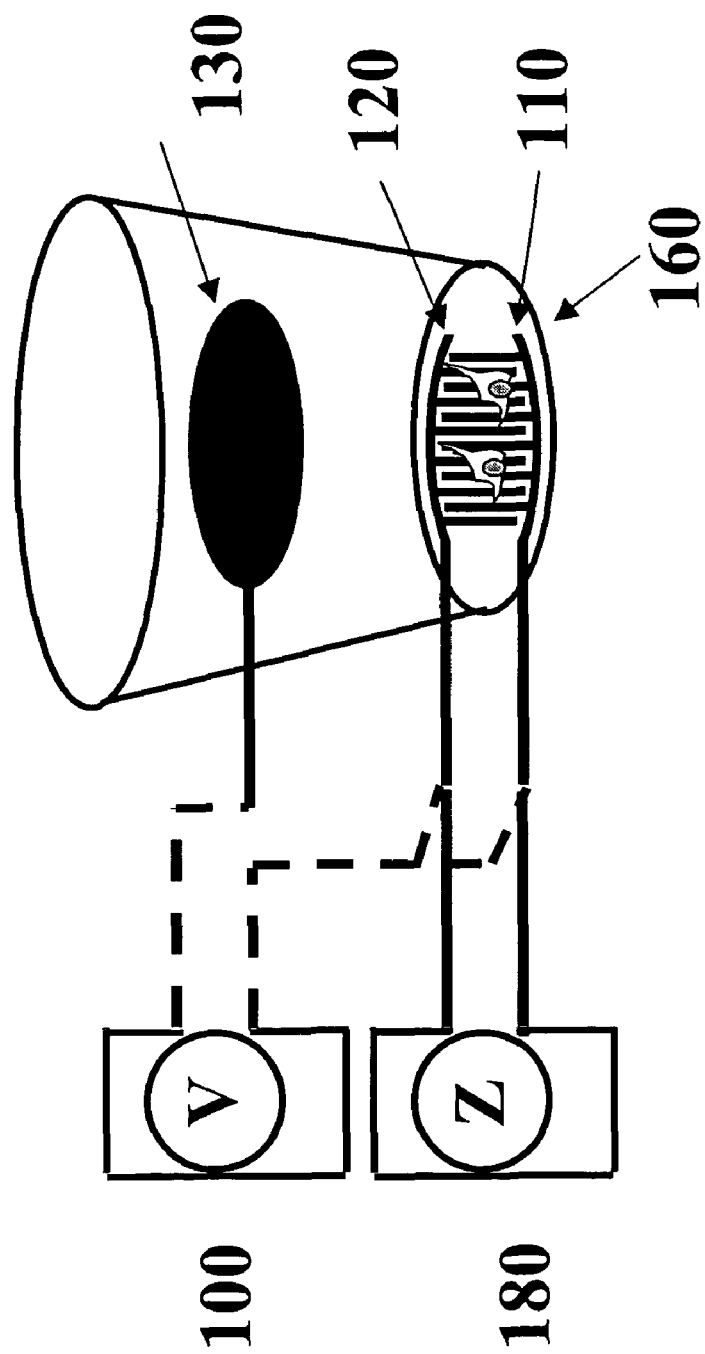
FIG. 1 depicts a well in a multi-well plate of a device of the present invention for monitoring cell-substrate impedance as well as for cell electroporation or cell electrostimulation. The device comprises electrode structures 110 and 120 on a non-conductive substrate 160, which are used for monitoring cell-substrate impedance with an impedance analyzer Z (180). The device further comprises a set of electroporation or electrostimulation electrodes: (1) the top electrode 130 and (2) the electrode structures 110 and 120 linked together. The set of electroporation or electrostimulation electrodes is connected to a signal source V (100) that can generate appropriate electrical signals for electroporation or electrostimulation of the cells.

For clarity of disclosure, and not by way of limitation, the detailed description of the invention is divided into the subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "membrane" is a sheet of material.

As used herein, "biocompatible membrane" means a membrane that does not have deleterious effects on cells, including the viability, attachment, spreading, motility, growth, or cell division.

A "biomolecular coating" or a "biological molecule coating" is a coating on a surface that comprises a molecule that is a naturally occurring biological molecule or biochemical, or a biochemical derived from or based on one or more naturally occurring biomolecules or biochemicals. For example, a biological molecule coating can include an extracellular matrix component (e.g., fibronectin, collagens), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occurring biochemicals.

An "organic compound coating" is a coating on a surface that includes an organic compound. For example an organic compound may include a natural ligand or an agonist or an antagonist for a cell surface receptor.

An "extracellular matrix component" is a molecule that occurs in the extracellular matrix of an animal. It can be a component of an extracellular matrix from any species and from any tissue type. Nonlimiting examples of extracellular matrix components include laminins, collagens fibronectins, other glycoproteins, peptides, glycosaminoglycans, proteoglycans, etc. Extracellular matrix components can also include growth factors.

An "electrode" is a structure having a high electrical conductivity, that is, an electrical conductivity much higher than the electrical conductivity of the surrounding materials. For the present application, electrodes are used for performing impedance measurement to monitor cellular effects or processes for cells attached to or located near the electrode surfaces or electrode regions, or for electroporating cells that are attached to or located near electrode regions, or for electrostimulating cells that are attached to or located near electrode regions. For the present application, electrostimulating cells refer to affecting cell membrane potential or inducing a change in cell membrane potential by subjecting cells to an appropriate electric field distribution in the region close to an electrostimulation electrode via applying an appropriate signal to an electrostimulation electrode.

As used herein, an "electrode structure" refers to a single electrode, particularly one with a complex structure (as, for example, a spiral electrode structure), or a collection of at least two electrode elements that are electrically connected together. All the electrode elements within an "electrode structure" are electrically connected.

As used herein, "electrode element" refers to a single structural feature of an electrode structure, such as, for example, a fingerlike projection of an interdigitated electrode structure.

As used herein, an "electrode array" or "electrode structure unit" is two or more electrode structures that are constructed to have dimensions and spacing such that they can, when connected to a signal source, operate as a unit to generate an electrical field in the region of spaces around the electrode structures. Preferred electrode structure units of the present invention can measure impedance changes due to cell attachment to an electrode surface. Or, preferred electrode structure units of the present invention, when connected to a signal source, can generate an electric field in the regions of spaces around the electrode structures so that when a cell or cell population is present in the space, the membranes of the cell or the population of cells can be electroporated so that molecules of interest can be delivered or transfected to the cells through electroporation-generated pores on the cell membrane. Or, preferred electrode structure units of the present invention, when connected to a signal source, can generate an electric field in the regions of spaces around the electrode structures so that when a cell or cell population is present in the space, the cell membrane potential is affected, leading to a change in cell membrane potential. Such a change in cell membrane potential can be localized so that the change for membrane potential may depend on the location of the cell membrane. Thus for a given cell, there may be a large change in cell membrane potential for some locations on the cell membrane and there may be a small change or no change in cell membrane potential for some other locations of the cell membrane. Non-limiting examples of electrode structure units are interdigitated electrode structure units and concentric electrode structure units.

An "electrode bus" is a portion of an electrode that connects individual electrode elements or substructures. An electrode bus provides a common conduction path from individual electrode elements or individual electrode substructures to another electrical connection. In the devices of the present invention, an electrode bus can contact each electrode element of an electrode structure and provide an electrical connection path to electrical traces that lead to a connection pad.

"Electrode traces" or "electrically conductive traces" or "electrical traces", are electrically conductive paths that extend from electrodes or electrode elements or electrode structures toward one end or boundary of a device or apparatus for connecting the electrodes or electrode elements or electrode structures to an impedance analyzer. The end or boundary of a device may correspond to the connection pads on the device or apparatus.

A "connection pad" is an area on an apparatus or a device of the present invention which is electrically connected to at least one electrode or all electrode elements within at least one electrode structure on an apparatus or a device and which can be operatively connected to external electrical circuits (e.g., an impedance measurement circuit or a signal source). The electrical connection between a connection pad and an impedance measurement circuit or a signal source can be direct or indirect, through any appropriate electrical conduction means such as leads or wires. Such electrical conduction means may also go through electrode or electrical conduction paths located on other regions of the apparatus or device.

"Interdigitated" means having projections coming one direction that interlace with projections coming from a different direction in the manner of the fingers of folded hands (with the caveat that interdigitated electrode elements preferably do not contact one another).

As used herein, a "high probability of contacting an electrode element" means that, if a cell is randomly positioned within the sensor area of a device or apparatus of the present invention, the probability of a cell (or particle) contacting on an electrode element, calculated from the average diameter of a cell used on or in a device or apparatus of the present invention, the sizes of the electrode elements, and the size of the gaps between electrode elements, is greater than about 50%, more preferably greater than about 60%, yet more preferably greater than about 70%, and even more preferably greater than about 80%, greater than about 90%, or greater than about 95%.

As used herein, "at least two electrodes fabricated on said substrate" means that the at least two electrodes are fabricated or made or produced on the substrate. The at least two electrodes can be on the same side of the substrate or on the different side of the substrate. The substrate may have multiple layers, the at least two electrodes can be either on the same or on the different layers of the substrate.

As used herein, "at least two electrodes fabricated to a same side of said substrate" means that the at least two electrodes are fabricated on the same side of the substrate.

As used herein, "at least two electrodes fabricated to a same plane of said substrate" means that, if the nonconducting substrate has multiple layers, the at least two electrodes are fabricated to the same layer of the substrate.

As used herein, "said . . . electrodes (or electrode structures) have substantially the same surface area" means that the surface areas of the electrodes referred to are not substantially different from each other, so that the impedance change due to cell attachment or growth on any one of the electrodes (or electrode structures) referred to will contribute to the overall detectable change in impedance to a same or similar degree as the impedance change due to cell attachment or growth on any other of the electrodes (or electrode structures) referred to. In other words, where electrodes (or electrode structures) have substantially the same surface area, any one of the electrodes can contribute to overall change in impedance upon cell attachment or growth on the electrode. In most cases, the ratio of surface area between the largest electrode and the smallest electrode that have "substantially the same surface area" is less than 10. Preferably, the ratio of surface area between the largest electrode and the smallest electrode of an electrode array is less than 5, 4, 3, 2, 1.5, 1.2 or 1.1. More preferably, the at least two electrodes of an electrode structure have nearly identical or identical surface area.

As used herein, "said device has a surface suitable for cell attachment or growth" means that the electrode and/or non-electrode area of the apparatus has appropriate physical, chemical or biological properties such that cells of interest can viably attach on the surface and new cells can continue to attach, while the cell culture grows, on the surface of the apparatus. However, it is not necessary that the device, or the surface thereof, contain substances necessary for cell viability or growth. These necessary substances, e.g., nutrients or growth factors, can be supplied in a medium. Preferably, when a suspension of viable, unimpaired, epithelial or endothelial cells is added to the "surface suitable for cell attachment" when at least 50% of the cells are adhering to the surface within twelve hours. More preferably, a surface that is suitable for cell attachment has surface properties so that at least 70% of the cells are adhering to the surface within twelve hours of plating (i.e., adding cells to the chamber or well that comprises the said device). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating.

As used herein, "detectable change in impedance between or among said electrodes" (or "detectable change in impedance between or among said electrode structures") means that the impedance between or among said electrodes (or electrode structures) would have a significant change that can be detected by an impedance analyzer or impedance measurement circuit when molecule binding reaction occurs on the electrode surfaces. The impedance change refers to the difference in impedance values when molecule binding reaction occurs on the electrode surface of the apparatus and when no molecular reaction occurs on the electrode surface. Alternatively, the impedance change refers to the difference in impedance values when cells are attached to the electrode surface and when cells are not attached to the electrode surface, or when the number, type, activity, adhesiveness, or morphology of cells attached to the electrode-comprising surface of the apparatus changes. In most cases, the change in impedance is larger than 0.1% to be detectable. Preferably, the detectable change in impedance is larger than 1%, 2%, 5%, or 8%. More preferably, the detectable change in impedance is larger than 10%. Impedance between or among electrodes is typically a function of the frequency of the applied electric field for measurement. "Detectable change in impedance between or among said electrodes" does not require the impedance change at all frequencies being detectable. "Detectable change in impedance between or among said electrodes" only requires a detectable change in impedance at any single frequency (or multiple frequencies). In addition, impedance has two components, resistance and reactance (reactance can be divided into two categories, capacitive reactance and inductive reactance). "Detectable change in impedance between or among said electrodes" requires only that either one of resistance and reactance has a detectable change at any single frequency or multiple frequencies. In the present application, impedance is the electrical or electronic impedance. The method for the measurement of such impedance is achieved by, (1) applying a voltage between or among said electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. Measurement of such electric impedance is an electronic or electrical process that does not involve the use of any reagents.

As used herein, "said at least two electrodes have substantially different surface area" means that the surface areas of any electrodes are not similar to each other so that the impedance change due to cell attachment or growth on the larger electrode will not contribute to the overall detectable impedance to a same or similar degree as the impedance change due to cell attachment or growth on the smaller electrodes. Preferably, any impedance change due to cell attachment or growth on the larger electrode is significantly smaller than the impedance change due to cell attachment or growth on the smaller electrode. Ordinarily, the ratio of surface area between the largest electrode and the smallest electrode is more than 10. Preferably, the ratio of surface area between the largest electrode and the smallest electrode is more than 20, 30, 40, 50 or 100.

As used herein, "multiple pairs of electrodes or electrode structures spatially arranged according to wells of a multi-well microplate" means that the multiple pairs of electrodes or electrode structures of a device or apparatus are spatially arranged to match the spatial configuration of wells of a multi-well microplate so that, when desirable, the device can be inserted into, joined with, or attached to a multiwell plate (for example, a bottomless multiwell plate) such that multiple wells of the multi-well microplate will comprise electrodes or electrode structures.

As used herein, "arranged in a row-column configuration" means that, in terms of electric connection, the position of an electrode, an electrode array or a switching circuit is identified by both a row position number and a column position number.

As used herein, "each well contains substantially same number . . . of cells" means that the lowest number of cells in a well is at least 50% of the highest number of cells in a well. Preferably, the lowest number of cells in a well is at least 60%, 70%, 80%, 90%, 95% or 99% of the highest number of cells in a well. More preferably, each well contains an identical number of cells.

As used herein, "each well contains . . . same type of cells" means that, for the intended purpose, each well contains same type of cells; it is not necessary that each well contains exactly identical type of cells. For example, if the intended purpose is that each well contains mammalian cells, it is permissible if each well contains same type of mammalian cells, e.g., human cells, or different mammalian cells, e.g., human cells as well as other non-human mammalian cells such as mice, goat or monkey cells, etc.

As used herein, "each well contains . . . serially different concentration of a test compound" means that each well contains a test compound with a serially diluted concentrations, e.g., an one-tenth serially diluted concentrations of 1 M, 0.1 M, 0.01 M, etc.

As used herein, "dose-response curve" means the dependent relationship of response of cells on the dose concentration of a test compound. The response of cells can be measured by many different parameters. For example, a test compound is suspected to have cytotoxicity and cause cell death. Then the response of cells can be measured by percentage of non-viable (or viable) cells after the cells are treated by the test compound. Plotting this percentage of non-viable (or viable) cells as a function of the dose concentration of the test compound constructs a dose response curve. In the present application, the percentage of non-viable (or viable) cells can be expressed in terms of measured impedance values, or in terms of cell index derived from impedance measurement, or in terms of cell change indexes. For example, for a give cell type and under specific cellular physiological condition (e.g., a particular cell culture medium), cell index can be shown to have a linear correlation or positive correlation with the number of viable cells in a well from which cell index was derived from the impedance measurement. Thus, in the present application, one can plot cell index as a function of the dose concentration of the test compound to construct a "dose-response curve". Note that, generally, cell index not only correlate with the number of viable cells in the wells but also relate to the cell morphology and cell attachment. Thus plotting cell index versus doss concentration provides information not only about number of cells but also about their physiological status (e.g. cell morphology and cell adhesion). Furthermore, an important advantage offered by the system and devices of the present invention is that in a single experiment, one can obtain "dose-response curves" at multiple time points since the system allows for the continuous monitoring of cells and provides impedance measurement at many time points over a time range as short as a few minutes to as long as days or weeks.

As used herein, "the electrodes have, along the length of the microchannel, a length that is substantially less than the largest single-dimension of a particle to be analyzed" means that the electrodes have, along the length of the microchannel, a length that is at least less than 90% of the largest single-dimension of a particle to be analyzed. Preferably, the electrodes have, along the length of the microchannel, a length that is at least less than 80%, 70%, 60%, 50%, 40%, 30%, 20%, 10%, 5% of the largest single-dimension of a particle to be analyzed.

As used herein, "the microelectrodes span the entire height of the microchannel" means that the microelectrodes span at least 70% of the entire height of the microchannel. Preferably, microelectrodes span at least 80%, 90%, 95% of the entire height of the microchannel. More preferably, microelectrodes span at least 100% of the entire height of the microchannel.

As used herein, "an aperture having a pore size that equals to or is slightly larger than size of said particle" means that aperture has a pore size that at least equals to the particle size but less than 300% of the particle size. Here both pore size and particle size are measured in terms of single dimension value.

As used herein, "microelectrode strip or electrode strip" means that a non-conducting substrate strip on which electrodes or electrode structure units are fabricated or incorporated. The non-limiting examples of the non-conducting substrate strips include polymer membrane, glass, plastic sheets, ceramics, insulator-on-semiconductor, fiber glass (like those for manufacturing printed-circuits-board). Electrode structure units having different geometries can be fabricated or made on the substrate strip by any suitable microfabrication, micromachining, or other methods. Non-limiting examples of electrode geometries include interdigitated electrodes, circle-on-line electrodes, diamond-on-line electrodes, castellated electrodes, or sinusoidal electrodes. Characteristic dimensions of these electrode geometries may vary from as small as less than 5 micron, or less than 10 micron, to as large as over 200 micron, over 500 micron, over 1 mm. The characteristic dimensions of the electrode geometries refer to the smallest width of the electrode elements, or smallest gaps between the adjacent electrode elements, or size of a repeating feature on the electrode geometries. The microelectrode strip can be of any geometry for the present invention. One exemplary geometry for the microelectrode strips is rectangular shape—having the width of the strip between less than 50 micron to over 10 mm, and having the length of the strip between less than 60 micron to over 15 mm. An exemplary geometry of the microelectrode strips may have a geometry having a width of 200 micron and a length of 20 mm. A single microelectrode strip may have two electrodes serving as a measurement unit, or multiple such two-electrodes serving as multiple measurement units, or a single electrode structure unit as a measurement unit, or multiple electrode structure units serving as multiple electrode structure units. In one exemplary embodiment, when multiple electrode structure units are fabricated on a single microelectrode strip, these electrode structure units are positioned along the length direction of the strip. The electrode structure units may be of squared-shape, or rectangular-shape, or circle shapes. Each of electrode structure units may occupy size from less than 50 micron by 50 micron, to larger than 2 mm×2 mm.

As used herein, "sample" refers to anything which may contain a moiety to be isolated, manipulated, measured, quantified, detected or analyzed using apparatuses, microplates or methods in the present application. The sample may be a biological sample, such as a biological fluid or a biological tissue. Examples of biological fluids include suspension of cells in a medium such as cell culture medium, urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbohydrates, chemical molecules binding to biological molecules).

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

A "compound" or "test compound" is any compound whose activity or direct or indirect effect or effects on cells is investigated in any assay. A test compound can be any compound, including, but not limited to, a small molecule, a large molecule, a molecular complex, an organic molecule, an inorganic molecule, a biomolecule or biological molecule such as but not limited to a lipid, a steroid, a carbohydrate, a fatty acid, an amino acid, a peptide, a protein, a nucleic acid, or any combination thereof. A test compound can be a synthetic compound, a naturally occurring compound, a derivative of a naturally-occurring compound, etc. The structure of a test compound can be known or unknown. In one application of the present invention, a compound is capable of, or is suspected of, effecting cell adhesion or cell spreading. In another application of present invention, a compound is capable of, or is suspected of, stimulating or inhibiting cell adhesion or cell spreading. In still another application, a compound is capable of, or is suspected of, interacting with cells (for example, binding to cell surface receptor, or inhibiting certain intracellular signal transduction pathway, or activating cells) In still another application, a compound is capable of, or is suspected of, affecting an ion channel activity (for example, blocking an ion channel).

A "known compound" is a compound for which at least one activity is known. In the present invention, a known compound preferably is a compound for which one or more direct or indirect effects on cells is known. Preferably, the structure of a known compound is known, but this need not be the case. Preferably, the mechanism of action of a known compound on cells is known, for example, the effect or effects of a known compound on cells can be, as nonlimiting examples, effects on cell viability, cell adhesion, apoptosis, cell differentiation, cell proliferation, cell morphology, cell cycle, IgE-mediated cell activation or stimulation, receptor-ligand binding, cell number, cell quality, cell cycling, cell adhesion, cell spreading, or effects on ion channel activity (for example, an ion channel blocker), etc.

An "impedance value" is the impedance measured for electrodes in a well with or without cell present. Impedance is generally a function of the frequency, i.e., impedance values depend on frequencies at which the measurement was conducted. For the present application, impedance value refers to impedance measured at either single frequency or multiple frequencies. Furthermore, impedance has two components, one resistance component and one reactance component. Impedance value in the present application refers to resistance component, or reactance component, or both resistance and reactance component. Thus, when "impedance value" was measured or monitored, we are referring to that, resistance, or reactance, or both resistance and reactance were measured or monitored. In many embodiments of the methods of the present application, impedance values also refer to parameter values that are derived from raw, measured impedance data. For example, cell index, or normalized cell index, or delta cell index could be used to represent impedance values.

An "impedance of a cell or cell population" is the impedance measured for electrodes when a cell or a cell population is attached to the electrodes or is placed in the regions close to the electrodes. When a cell or a cell population is attached to or adhered to the impedance-measurement electrodes, the "impedance of the cell or cell population" refers to the cell-substrate impedance. If a cell or a cell population is not attached to the impedance-measurement electrodes or a cell or a cell population is suspended in the regions close to the impedance-measurement electrodes, the "impedance of the cell or cell population" refers to the impedance of whole cell suspension. In some context of the present application, an "impedance of a cell or cell population" refers to the cell's impedance itself, or the cell population's impedance itself, without the contribution of the impedance from the measurement electrodes. Mathematical modeling may be needed in order to derive the cell's impedance or cell population's impedance from the impedance measured on the electrodes, for the cases of cells attached to the electrode/substrate surfaces or cells suspended in the regions close to the electrodes, A "Cell Index" or "CI" is a parameter that can derived from measured impedance values and that can be used to reflect the change in impedance values. There are a number of methods to derive or calculate Cell Index.

A "Normalized Cell Index" at a given time point is calculated by dividing the Cell Index at the time point by the Cell Index at a reference time point. Thus, the Normalized Cell Index is 1 at the reference time point.

A "delta cell index" at a given time point is calculated by subtracting the cell index at a standard time point from the cell index at the given time point. Thus, the delta cell index is the absolute change in the cell index from an initial time (the standard time point) to the measurement time.

A "Cell Change Index" or "CCI" is a parameter derived from Cell Index and "CCI" at a time point is equal to the $1^{st}$ order derive of the Cell Index with respect to time, divided by the Cell Index at the time point. In other words, CCI is calculated as $$CCI(t) = \frac{dCI(t)}{CI(t) \cdot dt}.$$

As used herein, "target cell" or "target cells" refers to any cell that is to be monitored for adhesion or spreading. Non-limiting examples of target cells include eukaryotic or prokaryotic cells of interest. Eukaryotic cells of particular interest may be human cells, a human cell population or a human cell line. Immune cells may be utilized such as B-lymphocytes, T-lymphocytes Natural Killer (NK) cells, Cytotoxic T-Lymphocytes (CTLs), neutrophils, easonophils, macrophages, Natural Killer T (NKT) cells, PBMCs and the like.

As used herein, "primary cell" or "primary cells" refers to any non-immortalized cell that has been derived from various tissues and organs of a patient or an animal.

B. Devices and Systems for Monitoring Cell-Substrate Impedance and for Electroporating or Electrostimulating Cells Devices for Measuring Cell-Substrate Impedance and for Electroporating or Electrostimulating Cells The present invention includes a number of devices capable of incorporating transfection with real time monitoring of impedance. The devices include the provided microelectronic devices. In one aspect the invention includes a device including a nonconductive substrate, a plurality of electrode arrays positioned on the substrate and at least one set of electroporation or electrostimulation electrodes. Each electrode array may include at least two electrodes and may be separated from at least one adjacent electrode by an area of non-conductive material. Each electrode array may be used for measuring cell-substrate impedance. In one embodiment the electroporation or electrostimulation electrodes are capable of electroporating a cell such that transfection of a molecule, a biomolecule or test compound into the cell via electroporation generated pores on the cell membrane may occur. For the present application, cell electroporation, or electroporation of cells or electroporating a cell all refer to transiently generating pores on cell membrane by applying appropriate electrical pulses or waveforms to electroporation electrodes so that molecules of interest can be delivered or transfected to cells. In another embodiment, the electrostimulation electrodes are capable of altering or affecting the membrane potential of a cell. The change in membrane potential allows the selective opening and/or closing of a voltage gated ion channel. For the present application, cell electrostimulation, electrostimulation of cells or electrostimulating cells all refer to transiently affecting cell membrane potential or inducing a change in cell membrane potential by applying appropriate electrical pulses or waveforms to electrostimulation electrodes.

Preferably the nonconducting substrate is planar, and is flat or approximately flat. Exemplary substrates can comprise many materials, including, but not limited to, silicon dioxide on silicon, silicon-on-insulator (SOI) wafer, glass (e.g., quartz glass, lead glass or borosilicate glass), sapphire, ceramics, polymer, fiber glass, plastics, e.g., polyimide (e.g. Kapton, polyimide film supplied by DuPont), polystyrene, polycarbonate, polyvinyl chloride, polyester, polypropylene and urea resin. A portion of the substrate may be substantially transparent to allow the passage of light. For cell-substrate impedance monitoring, any surface of the nonconducting substrate that can be exposed to cells during the use of a device of the present invention is preferably biocompatible. Substrate materials that are not biocompatible can be made biocompatible by coating with another material, such as polymer or biomolecular coating.

All or a portion of the surface of a substrate can be chemically treated, including but not limited to, modifying the surface such as by addition of functional groups, or addition of charged or hydrophobic groups. In some embodiments the surface is modified with compounds that are agonists or antagonists for a cell surface receptor involved in cell adhesion, including integrins, growth factor receptors, E-cadherins, N-cadherins, PECAMS and ICAMS.

An electrode array is two or more electrode structures that are constructed to have dimensions and spacing such that they can, when connected to a signal source, operate as a unit to generate an electrical field in the region of spaces around the electrode structures. An electrode structure refers to a single electrode, particularly one with a complex structure. (For example, an electrode structure can comprise two or more electrode elements that are electrically connected together.) In devices of the present invention, an electrode array comprises two electrode structures, each of which comprises multiple electrode elements, or substructures. In preferred embodiments of the present invention, the electrode structures of each of the two or more electrode arrays of a device have substantially the same surface area. In preferred embodiments of a device of the present invention, each of the two or more electrode arrays of a device includes two electrode structures, and each electrode structure includes multiple electrode elements. Each of the two electrode structures of an electrode array is connected to a separate connection pad that is located at the edge of the substrate.

Thus, in devices of the present invention, for each of the two or more electrode arrays of the device, the first of the two electrode structures is connected to one of the two or more connection pads, and the second of the two electrode structures is connected to another of the two or more connection pads. In some embodiments, each array of a device is individually addressed, meaning that the electrical traces and connection pads of the arrays are configured such that an array can be connected to an impedance analyzer in such a way that a measuring voltage can be applied across a single array at a given time by using switches (such as electronic switches). In other embodiments, groups or sections of a multiwell device are addressed.

Each electrode array of the device has an approximately uniform electrode resistance distribution across the entire array. By "uniform resistance distribution across the array" is meant that when a measurement voltage is applied across the electrode structures of the array, the electrode resistance at any given location of the array is approximately equal to the electrode resistance at any other location on the array. Preferably, the electrode resistance at a first location on an array of the device and the electrode resistance at a second location on the same array does not differ by more than 30%. More preferably, the electrode resistance at a first location on an array of the device and the electrode resistance at a second location on the same array does not differ by more than 15%. Even more preferably, the electrode resistance at a first location on an array of the device and a second location on the same array does not differ by more than 5%. More preferably yet, the electrode resistance at a first location on an array of the device and a second location on the same array does not differ by more than 2%.

For a device of the present invention, preferred arrangements for the electrode elements, gaps between the electrodes and electrode buses in a given electrode array for measuring cell-substrate impedance are used to allow all cells, no matter where they land and attach to the electrode surfaces, to contribute similarly to the total impedance change measured for the electrode array. Thus, it is desirable to have similar electric field strengths at any two locations within any given array of the device when a measurement voltage is applied to the electrode array. At any given location of the array, the field strength is related to the potential difference between the nearest point on a first electrode structure of the array and the nearest point on a second electrode structure of the array. It is therefore desirable to have similar electric potential drops across the electrode elements and across the electrode buses of a given array. Based on this requirement, it is preferred to have an approximately uniform electrode resistance distribution across the whole array where the electrode resistance at a location of interest is equal to the sum of the electrode resistance between the nearest point on a first electrode structure (that is the point on the first electrode structure nearest the location of interest) and a first connection pad connected to the first electrode structure and the electrode resistance between the nearest point on a second electrode structure (that is the point on the first electrode structure nearest the location of interest) and a second connection pad connected to the second electrode structure.

Devices of the present invention are designed such that the arrays of the device have an approximately uniform distribution across the whole array. This can be achieved, for example, by having electrode structures and electrode buses of particular spacing and dimensions (lengths, widths, thicknesses and geometrical shapes) such that the resistance at any single location on the array is approximately equal to the resistance at any single other location on the array. In most embodiments, the electrode elements (or electrode structures) of a given array will have even spacing and be of similar thicknesses and widths, the electrode buses of a given array will be of similar thicknesses and widths, and the electrode traces leading from a given array to a connection pad will be of closely similar thicknesses and widths. Thus, in these preferred embodiments, an array is designed such that the lengths and geometrical shapes of electrode elements or structures, the lengths and geometrical shapes of electrode traces, and the lengths and geometrical shapes of buses allow for approximately uniform electrode resistance distribution across the array.

In some preferred embodiments of cell-substrate impedance measurement devices, electrode structures comprise multiple electrode elements, and each electrode element connects directly to an electrode bus. Electrode elements of a first electrode structure connect to a first electrode bus, and electrode elements of a second electrode structure connect to a second electrode bus. In these embodiments, each of the two electrode buses connects to a separate connection pad via an electrical trace. Although the resistances of the traces contribute to the resistance at a location on the array, for any two locations on the array the trace connections from the first bus to a first connection pad and from the second bus to a second connection pad are identical. Thus, in these preferred embodiments trace resistances do not need to be taken into account in designing the geometry of the array to provide for uniform resistances across the array.

In some embodiments of the present invention, a device for monitoring cell-substrate impedance has two or more electrode arrays that share a connection pad. Preferably one of the electrode structures of at least one of the electrode arrays of the device is connected to a connection pad that also connects to an electrode structure of at least one other of the electrode arrays of the device. Preferably for at least two arrays of the device, each of the two or more arrays has a first electrode structure connected to a connection pad that connects with an electrode structure of at least one other electrode array, and each of the two or more arrays has a second electrode structure that connects to a connection pad that does not connect with any other electrode structures or arrays of the device. Thus, in preferred designs of a device there are at least two electrode arrays each of which has a first electrode structure that is connected to a common connection pad and a second electrode structure that is connected to an independent connection pad.

In some preferred embodiments of the present invention, each of the electrode structures of an array is connected to an electrode bus that is connected to one of the two or more connection pads of the device via an electrically conductive trace. In preferred embodiments, each of the two electrode structures is connected to a single bus, such that each array connects to two buses, one for each electrode structures. In this arrangement, each of the two buses connects to a separate connection pad of the substrate.

The electrically conductive traces that connect a bus with a connection can be fabricated of any electrically conductive material. The traces can be localized to the surface of the substrate, and can be optionally covered with an insulating layer. Alternatively the traces can be disposed in a second plane of the substrate. Description of arrangements and design of electrically conductive traces on impedance measurement devices can be found in U.S. patent application Ser. Nos. 10/705,447, 10/705,615, 10/987,732 and 11/055,639, herein incorporated by reference for all disclosure on fabrication and design of electrically conductive trace on substrates.

Appropriate electronic connection means such as metal clips engaged onto the connection pads on the substrate and connected printed-circuit-boards can be used for leading the electronic connections from the connection pads on the devices to external electronic circuitry (e.g. an impedance analyzer). Description of the design of cell-substrate impedance devices and their manufacture can be found in U.S. patent application Ser. Nos. 10/705,447, 10/705,615, 10/987, 732 and 11/055,639, herein incorporated by reference for all description and disclosure of the design, features, and manufacture of impedance device comprising electrode arrays.

Preferred electrode arrays for devices of the present invention for monitoring cell-substrate impedance include arrays comprising two electrode structures, such as, for example, spiral electrode arrays and interdigitated arrays. In some preferred devices of the present invention, electrode arrays are fabricated on a substrate, in which the arrays comprises two electrode structures, each of which comprises multiple circle-on-line electrode elements, in which the electrode elements of one structure alternate with the electrode elements of the opposite electrode structure.

Preferably, the electrode elements (or electrode structures) of an array of the present device of the present invention are of approximately equal widths. Preferably the electrode elements (or electrode structures) of an array of the present device of the present invention are greater than 30 microns in width, more preferably from about 50 to about 300 microns in width, and more preferably yet about 90 microns in width.

Preferably, the electrode elements (or electrode structures) of an array of the present device of the present invention are approximately evenly spaced. Preferably, the gap between electrode elements (or electrode structures) of an array of the present device of the present invention is less than 50 microns in width, more preferably from about 5 to about 30 microns in width, and more preferably yet about 20 microns in width.

A device of the present invention can include one or more fluid-impermeable receptacles which serve as fluid containers. Such receptacles may be reversibly or irreversibly attached to or formed within the substrate or portions thereof (such as, for example, wells formed as in a microtiter plate). In another example, the device of the present invention includes microelectrode strips reversibly or irreversibly attached to plastic housings that have openings that correspond to electrode structure units located on the microelectrode strips. Suitable fluid container materials comprise plastics, glass, or plastic coated materials such as ceramics, glass, metal, etc. Descriptions and disclosure of devices that comprise fluid containers can be found in U.S. patent application Ser. Nos. 10/705,447, 10/705,615, 10/987,732 and 11/055, 639, herein incorporated by reference for all disclosure of fluid containers and fluid container structures that can engage a substrate comprising electrodes for impedance measurements, including their dimensions, design, composition, and methods of manufacture.

In preferred embodiments, each electrode array on the substrate of a device of the present invention is associated with a fluid-impermeable container or receptacle, such as, for example, a well. Preferably, the device of the present invention is assembled to a bottomless, multiwell plastic plate or strip with a fluid tight seal. The device is assembled such that a single array of the substrate is at the bottom of a receptacle or well. Preferably, each array of a device is associated with a well of a multiwell plate. In some preferred embodiments, a multiwell device for cell-substrate impedance measurement has "non-array" wells that are attached to the substrate but not associated with arrays. Such wells can optionally be used for performing non-impedance based assays, or for viewing cells microscopically.

The design and assembly of multiwell impedance measurement devices is described in U.S. patent application Ser. No. 10/705,447, and also in U.S. patent application Ser. No. 10/987,732, both herein incorporated by reference for disclosure of multiwell impedance measurement devices, including their design, composition, and manufacture. A device of the present invention preferably has between 2 and 1,536 wells, more preferably between 4 and 384 wells, and even more preferably, between 16 and 96 wells, all or less than all or which are associated with electrode arrays.

In some preferred embodiments, commercial tissue culture plates can be adapted to fit a device of the present invention. Bottomless plates may also be custom-made to preferred dimensions. Preferably, well diameters are from about 1 millimeter to about 20 millimeters, more preferably from about 2 millimeters to about 8 millimeters at the bottom of the well (the end disposed on the substrate). The wells can have a uniform diameter or can taper toward the bottom so that the diameter of the container at the end in contact with the substrate is smaller than the diameter of the opposing end.

Electroporation or electrostimulation of cells may be performed using the electrode array described for performing cell-substrate impedance measurement above or may be performed using an additional set of electrodes. A set of electrodes include at least two electrodes. Electroporation or electrostimulation of the cell or cell population may employ a variety of pulses and waveforms applied to the electroporation or electrostimulation electrodes. Sinusoidal waveforms may allow for the straight forward yet accurate predication of the electric field applied to the cell membranes. Alternatively a square wave or waveform following an exponential delay may be applied.

In another configuration, a first half of the set of electroporation or electrostimulation electrodes are in or substantially in the plane of the substrate and a second half of the set of electrodes are not within the plane of the substrate. The electroporation or electrostimulation electrodes are separated such that a voltage may be induced across the electrodes thus causing electroporation-based transfecrion of a cell with a molecule, a biomolecule, a compound, an organic compound, a protein, a polypeptide, a nucleic acid molecule, a DNA molecule, a cDNA molecule, a native DNA, an isolated genomic DNA, a recombinant DNA, a plasmid, an anti-sense DNA strand, an oligonucleotide, an interfering RNA (RNAi) such as a small interfering RNA (siRNA), a micro RNA molecule, native RNA molecule, ribozyme RNA, an aptamer and the like. The molecule or compound may be capable of affecting transcription, translation, RNA splicing, RNA editing and the like. The molecule or compound may be capable of affecting cellular function such as cell proliferation, cell adhesion and cell spreading, or affecting cell morphology, or affecting a cellular receptor or signal transduction pathway activated by a cellular receptor.

In some embodiments the device comprises a plate including multiple wells and such wells are configured to include a top, bottom and sidewall. The bottom is constructed from nonconductive materials and a plurality of electrode arrays for impedance measurement are positioned at the bottom. The electroporation or electrostimulation electrodes may be in any suitable position such as generally along the bottom of the well and the top of the well or along the sidewall so long as an appropriate electrical field distribution may be induced to result in cell electroporation or electrostimulation after electrical pulses or waveforms are applied to electroporation or electrostimulation electrodes.

For example, a half of a set of electroporation or electrostimulation electrodes are positioned at the bottom and a second half of the set of electroporation or electrostimulation electrodes are positioned at the top. FIG. 1 shows a schematic drawing of a well in a multi-well plate of a device of the present invention for monitoring cell-substrate impedance as well as for cell electroporation or cell electrostimulation. The device comprises electrode structures 110 and 120 on a nonconductive substrate 160, which are used for monitoring cell-substrate impedance with an impedance analyzer Z (180). The device further comprises a set of electroporation or electrostimulation electrodes: (1) the top electrode 130 and (2) the electrode structures 110 and 120 linked together. The set of electroporation or electrostimulation electrodes is connected to a signal source V (100) that can generate appropriate electrical signals for electroporation or electrostimulation of the cells. In FIG. 1, electrode structures 110 and 120 are connected to impedance analyzer Z (180) for monitoring cell-substrate impedance. Electrode structure 120 refers to all the electrode elements connected to the parallel element 1, 3, 5, 7, 9 and 11 (counting from left of FIG. 1) and electrode structure 110 refers to all the electrode elements connected to the parallel element 2, 4, 6, 8, 10 and 12 (counting from left of FIG. 1). On the other hand, for electroporating or electrostimulating cells on the electrode structures 110 and 120, electrode structures 110 and 120 are connected together and are used as one electroporation or electrostimulation electrode to connect to one line (dashed lines in FIG. 1) from the signal source V (100). The top electrode 130 is used as the other electroporation or electrostimualtion electrode and is connected to the other line (dashed line in FIG. 1) from the signal source V (100). The top electrode may be a disc electrode, or an electrical wire, or an electrode of any suitable geometry. The distance from the top electrode 130 to the bottom electrode structures should be controlled so that an appropriate electric field distribution and strength can be generated in the well when electrical signals for electroporation or electrostimulation are applied.

Figure 2:
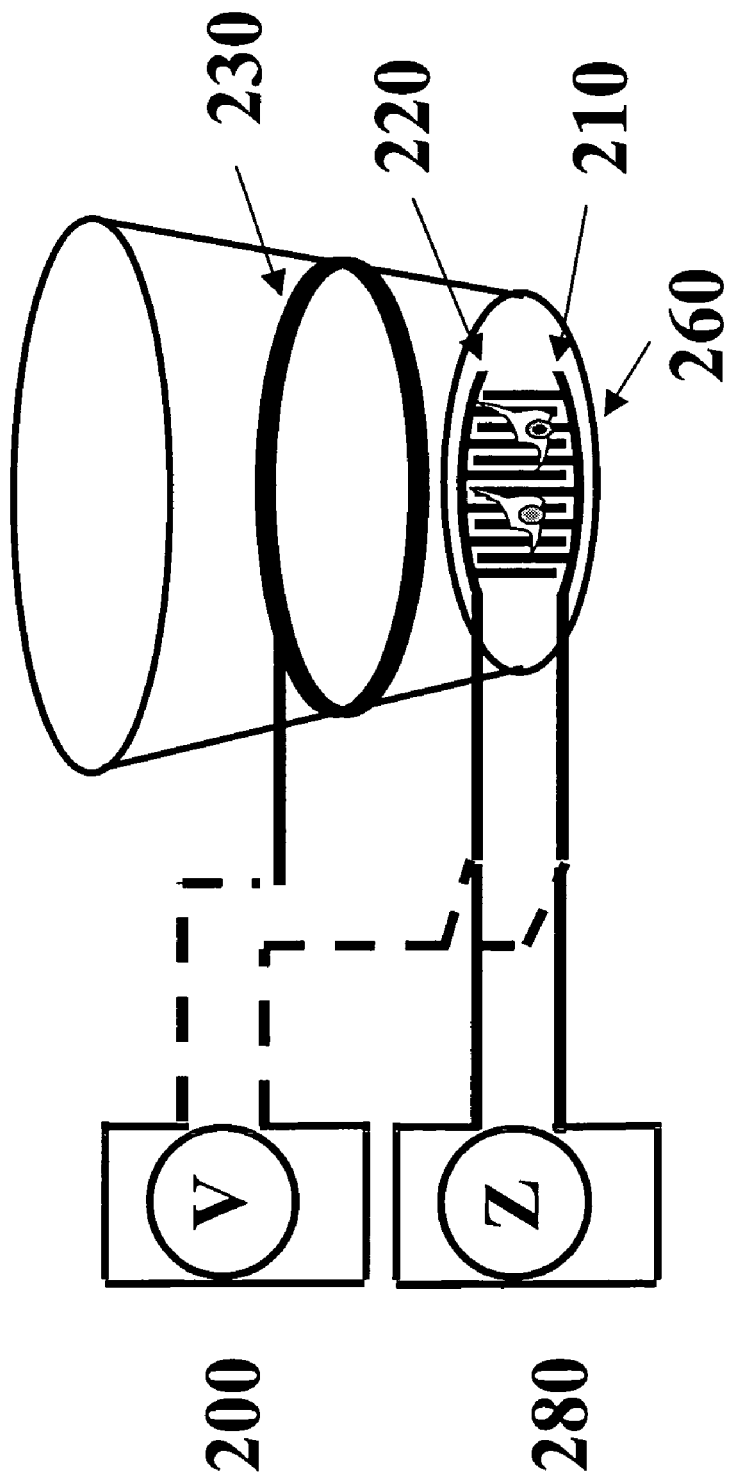
FIG. 2 depicts a well in a multi-well plate of a device of the present invention for monitoring cell-substrate impedance as well as for cell electroporation or cell electrostimulation. The device comprises electrode structures 210 and 220 on the nonconductive substrate 260, which are used for monitoring cell-substrate impedance with an impedance analyzer Z (280). The device further comprises a pair or a set of electroporation or electrostimulation electrodes: (1) the sidewall electrode 230 and (2) the electrode structures 210 and 220 linked together. The set of electroporation or electrostimulation electrodes is connected to a signal source V (200) that can generate appropriate electrical signals for electroporation or electrostimulation of the cells.

In another example, a half of a set of electroporation or electrostimulation electrodes are positioned at the bottom and a second half of the set of electroporation or electrostimulation electrodes are positioned along the sidewall. FIG. 2 shows a schematic drawing of a well in a muti-well plate of a device of the present invention for monitoring cell-substrate impedance as well as for cell electroporation or cell electrostimulation. The device comprises electrode structures 210 and 220 on a nonconductive substrate 260, which are used for monitoring cell-substrate impedance with an impedance analyzer Z (280). The device further comprises a pair or a set of electroporation or electrostimulation electrodes: (1) the sidewall electrode (ring-type on the sidewall) 230 and (2) the electrode structures 210 and 220 linked together. The set of electroporation or electrostimulation electrodes is connected to a signal source V (200) that can generate appropriate electrical signals for electroporation or electrostimulation of the cells. In FIG. 2, electrode structures 210 and 220 are connected to impedance analyzer Z (280) for monitoring cell-substrate impedance. Electrode structure 220 refers to all the electrode elements connected to the parallel element 1, 3, 5, 7, 9 and 11 (counting from left of FIG. 2) and electrode structure 210 refers to all the electrode elements connected to the parallel element 2, 4, 6, 8, 10 and 12 (counting from left of FIG. 2). On the other hand, for electroporating or electrostimulating cells on the electrode structures 210 and 220, electrode structures 210 and 220 are connected together and are used as one electroporation or electrostimulation electrode to connect to one line (dashed lines in FIG. 2) from the signal source V (200). The sidewall electrode 230 is used as the other electroporation or electrostimualtion electrode and is connected to the other line (dashed line in FIG. 2) from the signal source V (200). The sidewall electrode may be a ring electrode along the sidewall with suitable width of the ring, or an electrode of any geometry located on the sidewall. The distance from the sidewall electrode 230 to the bottom electrode structures should be controlled so that an appropriate electric field distribution and strength can be generated in the well when electrical signals for electroporation or electrostimulation are applied.

In another configuration a porous nonconductive film or substrate is positioned between a set of electroporation or electrostimulation electrodes. The porous nonconductive film or substrate is optionally beneath or under an electrode array for cell-substrate impedance measurement. In this configuration, upon application of electrical pulses or waveforms to the set of electroporation or electrostimulation electrodes, an electrical field is induced through the pores or channels in the porous, nonconductive film or substrate. Cells introduced onto or attached to the porous, nonconductive substrate may block or partially block the pores on the porous substrate, leading to a voltage drop across cell membrane and possible electroporation.

Figure 3:
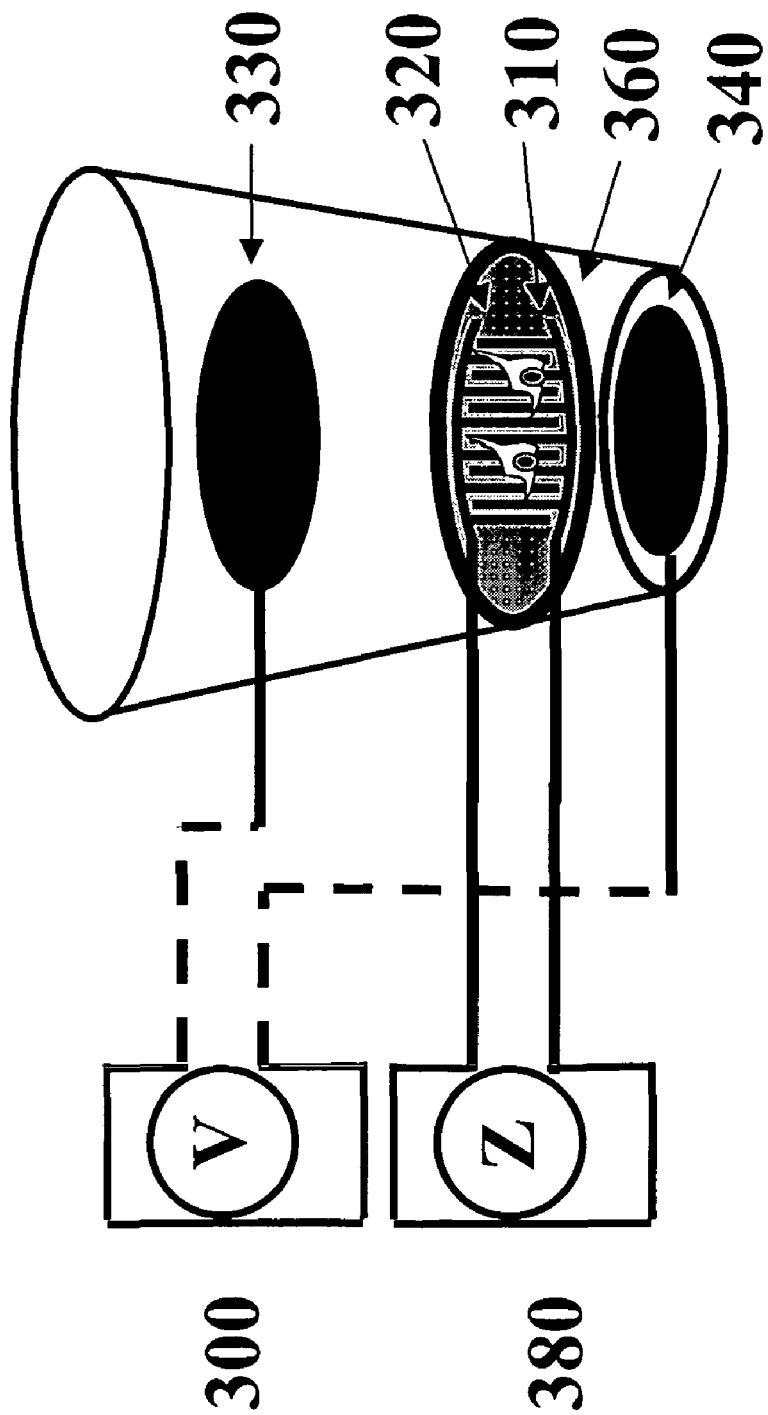
FIG. 3 depicts a well in a muti-well plate of a device of the present invention for monitoring cell-substrate impedance as well as for cell electroporation or cell electrostimulation. The device comprises electrode structures 310 and 320 on a porous, nonconductive substrate 360, which are used for monitoring cell-substrate impedance with an impedance analyzer Z (380). The device further comprises a pair or a set of electroporation or electrostimulation electrodes: (1) the top electrode 330 and (2) the bottom electrode 340. The set of electroporation or electrostimulation electrodes is connected to a signal source V (300) that can generate appropriate electrical signals for electroporation or electrostimulation of the cells.

FIG. 3 depicts a schematic drawing of a well in a muti-well plate of a device of the present invention for monitoring cell-substrate impedance as well as for cell electroporation or cell electrostimulation. The device comprises electrode structures 310 and 320 on a porous, nonconductive substrate 360, which are used for monitoring cell-substrate impedance with an impedance analyzer Z (380). Electrode structure 320 refers to all the electrode elements connected to the parallel element 1, 3, 5, 7, 9 and 11 (counting from left of FIG. 3) and electrode structure 310 refers to all the electrode elements connected to the parallel element 2, 4, 6, 8, 10 and 12 (counting from left of FIG. 3). The device further comprises a pair or a set of electroporation or electrostimulation electrodes: (1) the top electrode 330 and (2) the bottom electrode 340. For electroporation or electrostimulation of the cells, the set of electroporation or electrostimulation electrodes is connected to a signal source V (300) that can generate appropriate electrical signals. In FIG. 3, electrode structures 310 and 320 are connected to impedance analyzer Z (380) for monitoring cell-substrate impedance. On the other hand, for electroporating or electrostimulating cells on the electrode structures 310 and 320, the top electrode 330 is used as one electroporation or electrostimualtion electrode and is connected to one line (dashed line in FIG. 3) from the signal source V (300). The bottom electrode 340 is used as the other electroporation or electrostimulation electrode and is connected to the other line (dashed lines in FIG. 3) from the signal source V (300). The top electrode may be a disc electrode, or an electrical wire. The bottom electrodes 340 may be a disc electrode, or an electrode of any geometry underneath the porous substrate. The distance from the top electrode 330 to the bottom electrode 340 should be controlled so that an appropriate electric field distribution and strength can be generated in the well above the porous substrate 360 and in pores located on the porous substrate 360 when electrical signals for electroporation or electrostimulation are applied.

In another configuration a region of the substrate is used to optically detect a cell or cell population. This region may be free of electrode arrays, however this is not necessary. The region for optical detection of cells or cell populations may be used to visually or photographically or optically view cells or cell populations or may be accessible by a laser capable of detecting changes in a cell or cell population. The region for optical detection of cells or cell populations in a substrate may be of any regular or irregular shape, so long as it is suitable for optical detection or monitoring. For example, a circular shape, a square shape, a rectangular shape or an oval shape may be used. The area of such region for optical detection for a given well should be chosen to meet specific optical detection purposes. In some embodiments, minimum tens or hundreds of cells need to be optically monitored. Thus, the area for optical detection should be at least 1000 square-microns, or 10,000 square-microns, assuming that a minimum 100 or 1000 cells having 100 square microns are to be measured in a fully confluent state. On the other hand, the area can be as small as less 1000 square microns or as large as 10 square millimeters. Incorporating specific optical detection region on the substrate allows optical monitoring and electrical-impedance sensing of same cells located in a same well. Thus, the optical detection data can be directly compared or correlated with the electrical impedance measurement data. In some applications, electrical impedance measurement provides guide information about when an optical detection should be conducted.

The substrates or microelectronic plates capable of electroporation or electrostimulation may be multiwell plates such as a 96 well plate, 384 well plate a 1156 well plate and the like and may be capable of stacking one on top of another. Each well may be individually operable or addressable or may be provided in operably connected or addressable groups or sets.

Methods of Use

The present invention also includes methods of using the disclosed devices for cell electroporation, cell impedance monitoring and affecting the membrane potential of a cell. The methods may be used separately or in conjunction. The methods of the present invention for a cell-based assay include providing a device of the present invention having the capability of monitoring impedance and optionally electroporation or electrostimulation of cells, optionally including wells or fluid chambers situated over electrode arrays, attaching an impedance analyzer to a device of the present invention, adding cells to one or more fluid containers of the device, and measuring impedance over one or more arrays of the device.

In some embodiments, the method may also include transfecting a cell or cell population with a molecule of interest. In one exemplary approach, transfection of cell or cell population with the molecule of interest is achieved by applying appropriate electrical pulses or waveforms to electroporation electrodes to result in cell electroporation. Measuring impedance is performed before and after cell electroporation. The effect of transfected molecules in cell or cell population is determined by comparing the impedance of cell or cell population prior to and after cell electroporation. In another exemplary approach, transfection of cell or cell population is done with a chemical or viral transfection method. Measuring impedance is performed before and after the chemical or viral transfection. The effect of transfected molecules in cell or cell population is determined by comparing the impedance of cell or cell population prior to and after transfection of cell or cell population with the molecule of interest. In these embodiments, the molecule to be transfected include a biomolecule, a compound, an organic compound, a protein, a polypeptide, a nucleic acid molecule, a DNA molecule, a cDNA molecule, a native DNA, an isolated genomic DNA, a recombinant DNA, a plasmid, an anti-sense DNA strand, an oligonucleotide, an interfering RNA (RNAi) such as a small interfering RNA (siRNA), a micro RNA molecule, native RNA molecule, ribozyme RNA, an aptamer and the like. The molecule or compound may be capable of affecting transcription, translation, RNA splicing, RNA editing and the like. The molecule or compound may be capable of affecting cellular function such as cell proliferation, cell adhesion and cell spreading, or affecting cell morphology, or affecting a cellular receptor or signal transduction pathway activated by a cellular receptor.

In some embodiments, the effect of transfected molecules or compound on cells may be determined by monitoring impedance of cell or cell population before and after transfection of cells. In other embodiments, the effect of transfected molecules or compounds may be determined by monitoring impedance of cell or cell population at different time points after transfection of cells. In one approach, impedance of cell or cell population is monitored through the measurement of cell-substrate impedance for cells attached to electrode surfaces. In another approach, suspension cells are used and impedance or cell or cell population is determined by measuring impedance of suspension of cell population after transfection of cells.

Thus, the method of the present invention can be used generally to monitor effects of molecules transfected to or delivered to cells on cellular functions. Taking cell-substrate impedance measurement as an example, cell-substrate impedance reflects the cell number, cell distribution, cell morphology, cell adhesion, cell-substrate interaction for cells introduced in a well containing impedance-measurement electrodes on bottom of the wells. If the molecules transfected into cells have effects on any of above, their effects on cells may be directly and quantitatively monitored through cell-substrate impedance measurement. For example, if a siRNA molecule targeting Epidermal Growth Factor Receptor (EGFR) is used for transfecting the cells, cell proliferation is expected to be affected since the EGFR is an important factor for cell proliferation in many cells. Thus, the effect of such siRNA molecule can be monitored using cell-substrate impedance to measure cell proliferation. Similarly, if a siRNA molecule targeting EGFR is used for transfecting the cells, specific EGF-induced EGFR activation is expected to be affected. Since EGF-induced EGFR activation results in a change in cell morphology which can be detected through cell-substrate impedance monitoring, the effect of such siRNA can also be monitored using cell-substrate impedance to measure EGFR activation.

In other embodiments, the method may include affecting the membrane potential of a cell, leading to a change in cell membrane potential. A change in membrane potential may result in opening or closing a voltage gated ion channel.

In a preferred embodiment of the method of use of the device of the present invention, the method is directed to monitoring the effect of a compound on an ion channel is provided including providing a device capable of monitoring impedance of a cell or cell population and capable of inducing a change in a cell membrane potential; adding a cell or cell population comprising a voltage gated ion channel to the device; adding a test compound to the device; inducing a change in a cell membrane potential; and monitoring the impedance. Monitoring the impedance may be conducted before, during, after, or before and during and after adding the test compound the device. Monitoring the impedance may be conducted before and after inducing the change in cell membrane potential. The cell or cell population may further be monitored optically or by other means to measure cell membrane potential or other ion-channel activity associated parameters before and after inducing a change in cell membrane potential. In an exemplary embodiment, monitoring cell membrane potential is performed using an optical detection method after an optically detectable compound is added to the device. For example, a cell or cell population may be observed by detecting a membrane-potential-sensitive fluorescent dye added to the cell or cell population. Assessing or measuring cell membrane potential or other ion-channel activity-associated parameters may be performed at the same time as, or different times from, monitoring the impedance of cell population. The change in membrane potential may open or close a voltage gated ion channel. A cell index or normalized cell index may be determined and may be compared to the same cell or cell population or may be compared between different cells or cell populations.

Methods of performing cell assays using impedance measurement devices can be found in U.S. patent application Ser. No. 10/987,732, U.S. patent application Ser. No. 10/705,447, U.S. patent application Ser. No. 11/055,639, U.S. patent application Ser. No. 11/198,831, U.S. patent application Ser. No. 11/197,994, and U.S. patent application Ser. No. 11/235,938, all herein incorporated by reference for all disclosure of methods of using impedance measurement devices, as well as in Sections C and D of the present application.

Cell-Substrate Impedance Measurement Systems

In another aspect, the present invention is directed to a cell-substrate impedance measurement system comprising a) at least one multiple-well cell-substrate impedance measuring device, in which at least two of the multiple wells comprise an electrode array at the bottom of the well and optionally include a biological molecule or organic compound coating; b) an impedance analyzer electronically connected to the multiple-well cell-substrate impedance measuring device; c) a device station capable of engaging the one or more multiple-well devices and comprising electronic circuitry capable of selecting and connecting electrode arrays within any of the multiple wells to the impedance analyzer; and d) a software program connected to the device station and impedance analyzer to control the device station and perform data acquisition and data analysis from the impedance analyzer. The measuring device may also include a set of electroporation or electrostimulation electrodes.

In a cell-substrate impedance measurement system of the present invention, the impedance analyzer may engage connection pads of one or more multi-well devices to measure impedance. In one embodiment of the above system, the impedance analyzer is capable of measuring impedance between 0.1 ohm and $10^5$ ohm in frequency range of 1 Hz to 1 MHz. The impedance analyzer is preferably capable of measuring both resistance and reactance (capacitive reactance and inductive reactance) components of the impedance. In a preferred embodiment of the above system, the impedance analyzer is capable of measuring impedance between 0.1 ohm and $10^3$ ohm in frequency range of 100 Hz to 100 kHz.

Conventional electroporation typically uses DC voltage pulses or exponentially decaying voltage waveforms. For the disclosed technology, cell electroporation may use periodic waveforms such as sinusoidal waveforms, square waveforms or waveforms following an exponential decay for electroporating a cell sample or cell population. The application of such waveforms may allow for the straight forward yet accurate predication of the electrical field applied to the cell membranes, which may allow optimization of the voltage conditions that can achieve best electroporation efficiencies and lowest cell loss. There are a number of parameters that can be chose for such voltage waveforms, including but not limited to the magnitude, the frequency of the applied voltage signals, as well as the length of the voltage signals (Canatella, P. J., Karr, J. F., Petros, J. A., and Prausnitz, M. R., 2001, Biophys. J., Vol. 80, pp 755-764). Thus, the electroporator instrument may be used and such electroporator instrument can have the capabilities of generating the voltages with waveform frequency ranging from about 10 Hz to 1 MHz, the voltage from about 1 V to above 100 V with pulse lengths between 1 micro-second to several seconds. Waveform of the signals output from the electroporator instrument may include sinusoidal waveform, square waveform, triangular waveform and exponentially-decaying waveform. One important requirement for the electroporator instrument is that the generation of voltage signals of different parameters can be setup and controlled from a computer with a Windows base interface.

In another embodiment, a chemical, thermal or viral transfection method is used for transfecting cells with molecules of interest and the effect of transfected molecules in cells is monitored by monitoring impedance of cell or cell population after transfection. In one exemplary approach, cells are transfected using a chemical, thermal or viral transfection method after cell are preloaded into the device of the present invention for impedance monitoring. Thus, one exemplary embodiment of the method of the present invention comprises: providing a device of the present invention having the capability of monitoring impedance and including wells or fluid chambers situated over electrode arrays, attaching an impedance analyzer to a device of the present invention, adding cells to one or more fluid containers of the device, transfecting cells with molecules of interest and measuring impedance over one or more arrays of the device. The impedance measurement may be conducted before and after transfecting cells with molecules of interest. Since cell-substrate impedance reflects the cell number, cell distribution, cell morphology, cell adhesion, cell-substrate interaction, if the molecules transfected into cells have effects on any of above, their effects on cells may be directly and quantitatively monitored through cell-substrate impedance measurement. In another exemplary approach, cells are transfected using a chemical, thermal or viral transfection method in devices other than that for impedance monitoring. After transfection, cells are transferred to the device of the present invention for impedance monitoring.

For real time cell electronic sensing, one approach is as follows: a small electric voltage (~10 mV or smaller as a peak value) of sinusoidal waveform (other waveform is possible, but sine wave is preferred for the data interpretation) is applied to the two electrical connections, and the impedance is determined based on the measurement of the resulting electric current through the electrodes and some mathematical calculation involving the magnitudes and phases of voltage and current. In such a situation, it is preferred to apply as small voltages as possible so that the impedance measurement does not affect the cell biological status. As a contrast, for electrically stimulating the cells, voltages applied to the electrostimulation electrodes should be sufficient to affect and modulate the transmembrane potentials of the cells. For example, depending on the geometry of the microfabricated electrodes in the wells, voltage pulses ranging from less than 1 V to more than 100 V could be applied. The waveform of the voltage pulses can also be varied. As a non-limiting example, a variety of voltage waveforms described in U.S. Pat. No. 6,686,193 could be used. Still, as a contrast to cell electronic sensing, for electroporating cells, the voltages applied to the electroporation electrodes should be sufficient to result in the formation of transient pores at the cell membrane. Thus, depending on the geometry of the electroporation electrodes in the wells, voltage pulses ranging from less than 1 V to more than 100 V, having different waveforms such as sine wave, square wave, exponentially-decaying pulse waves may be used.

To generate electronic signals with suitable voltage waveforms and amplitude, suitable electronic signal generators are used or developed for such purposes. Signal generators may be capable of generating suitable electronic signals for stimulating the cells. For example, the signals can be appropriate periodic or aperiodic waveform (for example, single-polarity square wave, bi-polarity square wave, sine wave, triangular wave, exponential decay wave, or combination of above). For periodic waveform, the frequency of the signals can be from less than 1 Hz to more than 1 kHz. The magnitude of the signals can be varied, for example, from <1 V to >300 V. The signals can have any suitable length of time, for example, a series of square wave having period of 100 micro-second lasting from <1 ms to >100 ms. Preferably, the signal generator can be controlled from a computer so that any desired waveforms can be generated.

A cell-substrate measurement system can be used to efficiently and simultaneously perform multiple assays by using circuitry of the device station to digitally switch from recording from measuring impedance over an array in one well to measuring impedance over an array in another well. In one embodiment of the above system, the system under software control is capable of completing an impedance measurement for an individual well at a single frequency within less than ten seconds. In another embodiment, the averaged time used by the system to complete an impedance measurement for an individual well at a single frequency is less than one second. The impedance analyzer may measure or monitor impedance of groups of wells or different combinations of wells.

A multiple-well cell-substrate impedance measuring device in a system of the present invention can be any multiple-well cell-substrate impedance measuring device in which at least two of the multiple wells comprise an electrode array at the bottom of the well, and optionally in which at least two of the multiple wells comprise an electrode array are individually addressed. In one embodiment of the above system, the multi-well device takes the form of a specialized microtiter plate which has microelectronic sensor arrays integrated into the bottom of the wells and a biological molecule or organic compound covalently or noncovalently bound thereto.

A device used in a system of the present invention, when connected to an impedance analyzer, can measure differences in impedance values that relate to cell behavior. For example, a cell-substrate impedance measuring device used in a system of the present invention can measure differences in impedance values when cells are attached to the electrode array and when cells are not attached to the electrode array, or can detect differences in impedance values when the number, type, activity, adhesiveness, or morphology of cells attached to the electrode-comprising surface of the apparatus changes. In particular the present invention can detect adhesion of cells as well as cell spreading.

Preferred devices that can be part of a cell-substrate impedance monitoring system can be those described in U.S. patent application Ser. No. 10/705,447, in U.S. patent application Ser. No. 10/987,732, and in U.S. patent application Ser. No. 11/055,639, all herein incorporated by reference for disclosure of cell-substrate impedance monitoring devices that comprise electrode arrays, including disclosure of their design, composition, and manufacture. Preferred devices that can be part of a cell-substrate impedance monitoring system can also be those described in the present application.

Preferably a multi-well device of a system of the present invention comprises between 4 and 1,536 wells, some or all of which can comprise electrode arrays. In some embodiments of the present invention, a device station can comprise one or more platforms or one or more slots for positioning one or more multiwell devices. The one or more platforms or one or more slots can comprise sockets, pins or other devices for electrically connecting the device to the device station. The device station preferably can be positioned in a tissue culture incubator during cell impedance measurement assays. It can be electrically connected to an impedance analyzer and computer that are preferably located outside the tissue culture incubator.

The device station comprises electronic circuitry that can connect to an impedance monitoring device and an impedance analyzer and electronic switches that can switch on and off connections to each of the two or more electrode arrays of the multiwell devices used in the system. The device may further comprise electronic circuitry that can connect to a signal generator (for example, a electroporator instrument or electrostimulation waveform generator) and an electroporation or electrostimulation electrodes and electrical switches that can switch on and off connections to each set of electroporation or electrostimulation electrodes in the multiwell devices used in the system. The device station can control the switching of electrode arrays and electroporation or electrostimulation electrodes. The switches of the device station are controlled by a software program. The software program directs the device station to connect arrays of the device to an impedance analyzer and monitor impedance from one or more of the electrode arrays. The software program may further direct the device station to connect one set of electroporation or electrostimulation electrodes to a signal generator and direct the signal generator to produce desired signals with appropriate waveform and signal amplitudes. During impedance monitoring, the impedance analyzer can monitor impedance at one frequency or at more than one frequency. Preferably, impedance monitoring is performed at more than one time point for a given assay, and preferably, impedance is monitored at at least three time points. The device station can connect individual arrays of a device to an impedance analyzer to monitor one, some, or all of the arrays of a device for a measurement time point. The switches of the device station allow the selected individual arrays to be monitored in rapid succession for each desired monitoring time point. Each monitoring time point is in fact a narrow time frame (for example from less than one second to minutes) of measurement in the assay during which impedance monitoring is performed. In some preferred embodiments of the present invention, the device station software is programmable to direct impedance monitoring of any of the wells of the device that comprise arrays at chosen time intervals.

The software of the impedance monitoring system can also store and display data. Data can be displayed on a screen, as printed data, or both. Preferably the software can allow entry and display of experimental parameters, such as descriptive information including cells types, compound concentrations, time intervals monitored, etc.

Preferably, the software can also analyze impedance data. In preferred embodiments, the software can calculate a cell index (CI) for one or more time points for one or more wells of the multiwell device. In some preferred embodiments, the software can calculate a cell change index (CCI) from impedance measurements of one or more wells of the multiwell device. The software can preferably generate plots of impedance data and impedance values, such as but not limited to CI or CCI, with respect to time. The software may perform other analysis as well, such as calculate cell number from CI, generate dose-response curves based on impedance data, calculate IC values based on impedance values, and calculate kinetic parameters of cell growth or behavior based on impedance values and impedance value curves. The software of the impedance monitoring system can also store and display analyses of the data, such as calculated impedance values and kinetic parameters derived, Data can be displayed on a screen, as printed data, or both.

C. Methods for Calculating Cell Index (CI) and Cell Change Index (CCI)

Cell Index

Based on the dependent relationship between the measured impedance, cell number (more accurately, the viable cell number, or attached cell number) and cell attachment status, it is possible to derive a so-called "cell number index" or "cell index" from the measured impedance frequency spectra that provides a useful index for quantitating and comparing cell behavior in the impedance-based assays of the present invention. In some applications of the present invention, "cell index" in the present application is the same as "cell number index" in PCT Application No. PCT/US03/22557, entitled "IMPEDANCE BASED DEVICES AND METHODS FOR USE IN ASSAYS", filed on Jul. 18, 2003 and in U.S. patent application Ser. No. 10/705,447, entitled "IMPEDANCE BASED DEVICES AND METHODS FOR USE IN ASSAYS," filed on Nov. 10, 2003, U.S. patent application Ser. No. 10/987,732, filed Nov. 12, 2004, U.S. patent application Ser. No. 10/705,447 and PCT Application No. PCT/US03/22557 are hereby incorporated by reference for the discussions and disclosures of cell index and cell number index they contain.

Various methods for calculating such a cell number index can be used, some of which are novel methods disclosed herein.

The present invention provides several methods of calculating cell index numbers for cells attached to two or more essentially identical arrays of a cell-substrate impedance device, where the cells are monitored for impedance changes. In preferred embodiments of the present invention, the methods calculate cell index number with better accuracy than previous methods of calculating cell index for cells on two or more arrays of a cell-substrate monitoring device. In some preferred methods of the present invention, methods of calculating a cell index rely on novel methods for calculating the resistances of electrical traces leading to two or more essentially identical arrays. The present invention therefore also includes methods of calculating resistances of electrical traces leading to two or more essentially identical arrays on a substrate.

By "essentially identical electrode arrays" or "essentially identical arrays" is meant that the dimensions and arrangement of electrodes, electrode structures, and electrode elements is the same for the referenced arrays. Thus, two essentially identical electrode arrays will have electrode structures of the same dimensions (length, width, thickness), where the electrode structures have the same number of electrode elements, and the arrangement of electrode structures and electrode elements in each array are the same. By arrangement is meant the distance between structures or elements (gap width), their physical position with respect to one another, and their geometry (angles, degree of curvature, circle-on-line or castellated geometries, etc.), including the same features of any electrode buses that may be connected to electrode structures or electrode elements. Electrodes of essentially identical arrays also comprise the same materials. For the purposes of calculating trace resistances and cell index number, a substrate can have any number of essentially identical arrays.

The following discussion provides novel methods of calculating cell index of cells adhered to arrays of a cell-substrate impedance monitoring device and novel methods for the calculation of the resistances of the electrical connection traces leading to two or more electrode arrays of a cell-substrate impedance monitoring device.

Impedance (Z) has two components, namely the resistance Rs and reactance Xs. Mathematically, the impedance Z is expressed as follows, $$Z = Rs + jXs, \quad (2)$$

where $j=\sqrt{-1}$, depicting that for the (serial) reactance component Xs, the voltage applied over it is 90 degree phased-out from the current going through it. For the (serial) resistance, the voltage applied over it is in phase with the current going through it. As it is well-known in electronic and electrical engineering, the impedance can also be expressed in terms of parallel resistance Rp and parallel reactance Xp, as follows, $$Z = Rp*(jXp)/(Rp+jXp), \quad (3)$$

where $j=\sqrt{-1}$. Nevertheless, these expressions (serial resistance and serial reactance, or parallel resistance and parallel reactance) are equivalent. Those who are skilled in electrical and electronic engineering can readily derive one form of expression from the parameter values in the other expression. For the sake of clarity and consistency, the description and discussion in the present invention utilizes the expression of serial resistance and serial reactance. For simplicity, serial resistance and serial reactance are simply called resistance and reactance.

As described in U.S. patent application Ser. No. 10/705,447, entitled "Impedance based devices and methods for use in assays", filed on Nov. 10, 2003 and PCT application number PCT/US03/22557, entitled "Impedance based devices and methods for use in assays", filed on Jul. 18, 2003, both of which are herein incorporated by reference for disclosures relating to cell-substrate impedance monitoring, monitoring cell-substrate impedance for detection or measurement of change in impedance can be done by measuring impedance in any suitable range of frequencies. For example, the impedance can be measured in a frequency range from about 1 Hz to about 100 MHz. In another example, the impedance can be measured in a frequency range from about 100 Hz to about 2 MHz. The impedance is typically a function of the frequency, i.e., the impedance values change as frequency changes. Monitoring cell-substrate impedance can be done either in a single frequency or multiple frequencies. If the impedance measurement is performed at multiple frequencies, then a frequency-dependent impedance spectrum is obtained—i.e., there is an impedance value at each measured frequency. As mentioned above, the impedance has two components—a resistance component and a reactance component. A change in either resistance component or reactance component or both components can constitute a change in impedance.

As described in the U.S. patent application Ser. No. 10/705,447, entitled "Impedance based devices and methods for use in assays", filed on Nov. 10, 2003 and PCT application number PCT/US03/22557, entitled "Impedance based devices and methods for use in assays", filed on Jul. 18, 2003, herein incorporated by reference for disclosure of methods of measuring electrical impedance, the method for the measurement of electrical (or electronic) impedance is achieved by, (1) applying a voltage between or among said electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. As it is well-known in electrical and electronic engineering, in such calculations (e.g. divisions mentioned above), the current amplitude and voltage amplitude are expressed in the form of complex numbers, which take into account of how big the current and the voltage are and what the phase difference between the sinusoidal waves of the current and the voltage is. Similarly, the impedance value is also expressed in a complex form, having both resistance and reactance component, as shown in equations above.

As described in the U.S. patent application Ser. No. 10/705,447, entitled "Impedance based devices and methods for use in assays", filed on Nov. 10, 2003 and PCT application number PCT/US03/22557, entitled "Impedance based devices and methods for use in assays", filed on Jul. 18, 2003, both incorporated herein by reference for disclosure relating to Cell Index or Cell Number Index, the measured cell-substrate impedance can be used to calculate a parameter termed Cell Index or Cell Number Index. Various methods for calculating such a cell number index can be used based on the changes in resistance or reactance when cells are attached to the electrode structures with respect to the cases no cells are attached to the electrode structures. The impedance (resistance and reactance) of the electrode structures with no cell attached but with same cell culture medium over the electrode structures is sometimes referred as baseline impedance. The baseline impedance may be obtained by one or more of the following ways: (1) the impedance measured for the electrode structures with a cell-free culture medium introduced into the well containing the electrode structures, wherein the culture medium is the same as that used for the impedance measurements for the condition where the cell attachment or spreading is monitored; (2) the impedance measured shortly (e.g. 10 minutes) after the cell-containing medium was applied to the wells comprising the electrode structures on the well bottom (during the short period after cell-containing medium addition, cells do not have enough time to attach to the electrode surfaces. The length of this short-period may depend on cell type and/or surface treatment or modification on the electrode surfaces); (3) the impedance measured for the electrode structures when all the cells in the well were killed by certain treatment (e.g. high-temperature treatment) and/or reagents (e.g. detergent) (for this method to be used, the treatment and/or reagents should not affect the dielectric property of the medium which is over the electrodes).

In one example (A), the cell index or cell number index can be calculated by:
(A1) at each measured frequency, calculating the resistance ratio by dividing the resistance of the electrode arrays when cells are present and/or attached to the electrodes by the baseline resistance,
(A2) finding or determining the maximum value in the resistance ratio over the frequency spectrum,
(A3) and subtracting one from the maximum value in the resistance ratio.

Using a mathematically formula, Cell Index is derived as $$\text{Cell Index} = \max_{i=1,2,\ldots N}\left(\frac{R_{cell}(f_i)}{R_b(f_i)} - 1\right) \qquad (4)$$

Where N is the number of the frequency points at which the impedance is measured. For example, if the frequencies used for the measurements are at 10 kHz, 25 kHz and 50 kHz, then N=3, $f_1$=10 kHz, $f_2$=25 kHz, $f_3$=50 kHz. $R_{cell}(f_i)$ is the resistance (cell-substrate resistance) of the electrode arrays or electrode structures when the cells are present on the electrodes at the frequency $f_i$ and $R_b(f_i)$ is the baseline resistance of the electrode array or structures at the frequency $f_i$.

The cell index obtained for a given well reflects: 1) how many cells are attached to the electrode surfaces in this well, 2) how well cells are attached to the electrode surfaces in the well. In this case, a zero or near-zero "cell index or cell number index" indicates that no cells or very small number of cells are present on or attached to the electrode surfaces. In other words, if no cells are present on the electrodes, or if the cells are not well-attached onto the electrodes, $R_{cell}(f_i)$ is about the same as $R_b(f_i)$, leading to Cell Index=0. A higher value of "cell number index" indicates that, for same type of the cells and cells under similar physiological conditions, more cells are attached to the electrode surfaces. In other words, under same physiological conditions, more cells attached on the electrodes, the larger the values $R_{cell}(f_i)$ is, leading to a large value for Cell Index. Thus Cell Index is a quantitative measure of cell number present in a well. A higher value of "cell index" may also indicate that, for same type of the cells and same number of the cells, cells are attached better (for example, cells spread out more, or cell adhesion to the electrode surfaces is stronger) on the electrode surfaces. Thus, for same number of the cells present in the well, change in a cell status will lead to a change in cell index. For example, an increase in cell adhesion or a cell spread leading to large cell/electrode contact area will result in an increase in $R_{cell}(f)$ and a larger Cell Index. On the other hand, a cell death or toxicity induced cell detachment, cell rounding up, will lead to smaller $R_{cell}(f)$ and thus smaller Cell Index.

In another example (B), the cell number index can be calculated by:
(B1) at each measured frequency, calculating the reactance ratio by dividing the reactance of the electrode arrays when cells are present on and/or attached to the electrodes by the baseline reactance,
(B2) finding or determining the maximum value in the reactance ratio over the frequency spectrum,
(B3) and subtracting one from the maximum value in the resistance ratio.

In this case, a zero or near-zero "cell number index" indicates that no cells or very small number of cells are present on or attached to the electrode surfaces. A higher value of "cell number index" indicates that, for same type of the cells and cells under similar physiological conditions, more cells are attached to the electrode surfaces.

In yet another example (C), the cell index can be calculated by:
(C1) at each measured frequency, subtracting the baseline resistance from the resistance of the electrode arrays when cells are present or attached to the electrodes to determine the change in the resistance with the cells present relative to the baseline resistance;
(C2) then finding or determining the maximum value in the change of the resistance.

In this case, "cell-number index" is derived based on the maximum change in the resistance across the measured frequency range with the cells present relative to the baseline resistance. This cell index would have a dimension of ohm.

In yet another example (D), the cell index can be calculated by:

(D1) at each measured frequency, calculating the magnitude of the impedance (equaling to $\sqrt{R_s^2+X_s^2}$, where $R_s$ and $X_s$ are the serial resistance and reactance, respectively).

(D2) subtracting the magnitude of the baseline impedance from the magnitude of the impedance of the electrode arrays when cells are present or attached to the electrodes to determine the change in the magnitude of the impedance with the cells present relative to the baseline impedance;

(D3) then finding or determining the maximum value in the change of the magnitude of the impedance.

In this case, "cell-number index" is derived based on the maximum change in the magnitude of the impedance across the measured frequency range with the cells present relative to the baseline impedance. This cell index would have a dimension of ohm.

In yet another example (E), the index can be calculated by:

(E1) at each measured frequency, calculating the resistance ratio by dividing the resistance of electrode arrays when cells are present or attached to the electrodes by the baseline resistance, (E2) then calculating the relative change in resistance in each measured frequency by subtracting one from the resistance ratio, (E3) then integrating all the relative-change value (i.e., summing together all the relative-change values at different frequencies).

In this case, "cell-number index" is derived based on multiple-frequency points, instead of single peak-frequency like above examples. Again, a zero or near-zero "cell number index" indicates that on cells are present on the electrodes. A higher value of "cell number index" indicates that, for same type of the cells and cells under similar physiological conditions, more cells are attached to the electrodes.

In yet another example (F), the cell index can be calculated by:

(F1) at each measured frequency, subtracting the baseline resistance from the resistance of the electrode arrays when cells are attached to the electrodes to determine the change in the resistance with the cells present relative to the baseline impedance; (here the change in the resistance is given by $\Delta R(f_i)=R_{s\text{-}cell}(f_i)-R_{s\text{-}baseline}(f_i)$ for the frequency $f_i$, $R_{s\text{-}cell}$ and $R_{s\text{-}baseline}$ are the serial resistances with the cells present on the electrode array and the baseline serial resistances, respectively);

(F3) analyzing the frequency dependency of the change of the resistance to derive certain parameters that can quantify such dependency. In one example, such parameters can be calculated as $$\sqrt{\sum_i [\Delta R(f_i)]^2}.$$

In another example, such parameter can be calculated as $$\sum_i |\Delta R(f_i)|.$$

The parameter(s) are used as cell index or cell number index.

In this case, "cell-number index" is derived based on the analysis of the frequency spectrum of the change in the resistance. Depending how the parameters are calculated, the cell index may have a dimension of ohm.

In yet another example (G), the cell index can be calculated by:

(G1) at each measured frequency, calculating the magnitude of the impedance (equaling to $\sqrt{R_s^2+X_s^2}$, where $R_s$ and $X_s$ are the serial resistance and reactance, respectively).

(G2) subtracting the magnitude of the baseline impedance from the magnitude of the impedance of the electrode arrays when cells are attached to the electrodes to determine the change in the magnitude of the impedance with the cells present relative to the baseline impedance; (here, the change in the magnitude of the impedance is given by $\Delta Z(f_i)=|Z_{cell}(f_i)|-|Z_{baseline}(f_i)|$ for the frequency $f_i$, $|Z_{cell}(f_i)|=\sqrt{R_{s\text{-}cell}(f_i)^2+X_{s\text{-}cell}(f_i)^2}$, $R_{s\text{-}cell}$ and $X_{s\text{-}cell}$ being the serial resistance and reactance with the cells present on the electrode arrays, respectively, $|Z_{cell}(f_i)|$ is the magnitude of the impedance of the electrode array with cells present on the electrode arrays, $|Z_{baseline}(f_i)|$ is the magnitude of the baseline impedance of the electrode array);

(G3) analyzing the frequency dependency of the change of the magnitude of the impedance to derive certain parameters that can quantify such dependency. In one example, such parameters can be calculated as $$\sqrt{\sum_i [\Delta Z(f_i)]^2}.$$

In another example, such parameter can be calculated as $$\sum_i |\Delta Z(f_i)|.$$

The parameter(s) are used as cell index or cell number index.

In this case, "cell-number index" is derived based on the analysis of the frequency spectrum of the change in the magnitude of the impedance. Depending how the parameters are calculated, the cell index may have a dimension of ohm.

As described in the U.S. patent application Ser. No. 10/705,447, entitled "Impedance based devices and methods for use in assays", filed on Nov. 10, 2003 and PCT application number PCT/US03/22557, entitled "Impedance based devices and methods for use in assays", filed on Jul. 18, 2003, and U.S. patent application Ser. No. 10/987,732, all herein incorporated by reference for disclosure of Cell Index or Cell Number Index and its calculation, there are different methods for calculating the parameter termed Cell Index or Cell Number Index from the measured cell-substrate impedance (resistance or reactance). Cell Index or Cell Number Index is a quantitative measure of cells in the wells under cell-substrate impedance measurement.

It is worthwhile to point out that it is not necessary to derive such a "cell number index" for utilizing the impedance information for monitoring cell conditions over the electrodes. Actually, one may choose to directly use measured impedance (e.g., at a single fixed frequency; or at a maximum relative-change frequency, or at multiple frequencies) as an indicator of cell conditions. If measured impedance values are directly used for monitoring cell conditions, then resistance, or reactance or both resistance and reactance can be used.

Still, deriving "cell index" or "cell number index" and using such index to monitor cell conditions may have advantages. There are several advantages of using "cell number index" to monitor cell growth and/or attachment and/or viability conditions.

First, one can compare the performance of different electrode geometries by utilizing such cell number index.

Secondly, for a given electrode geometry, it is possible to construct "calibration curve" for depicting the relationship between the cell number and the cell number index by performing impedance measurements for different number of cells added to the electrodes (in such an experiment, it is important to make sure that the seeded cells have well-attached to the electrode surfaces). With such a calibration curve, when a new impedance measurement is performed, it is then possible to estimate cell number from the newly-measured cell number index.

Thirdly, cell number index can also be used to compare different surface conditions. For the same electrode geometry and same number of cells, a surface treatment given a larger cell number index indicates a better attachment for the cells to the electrode surface and/or better surface for cell attachment.

As shown above, for some methods of calculating cell index or cell number index, it is important to know the impedance (resistance and/or reactance) of the electrode structures with and without cells present on them. Based on the equation (1), the impedance of the electrode array (with or without cells present on the electrodes) is given by $$Z_{electrode-array} = Z_{total} - Z_{trace} - Z_{switch} \quad (5)$$

Where $Z_{switch}$ is the impedance of electronic switch at its on stage, $Z_{trace}$ is the impedance of the electrical connection traces (or electrical conductive traces) on the substrate between the connection pads and the electrode buses, $Z_{total}$ is the total impedance measured at the impedance analyzer. By choosing electronic switches with good quality, it is possible to have all the electronic switches have a consistent on-impedance (mainly resistance). For example, the on-resistance of electronic switches can be about 3 ohm (+/−10%) with the on reactance being negligible (for example, less than 0.2 ohm in the frequency range of interest). Thus, if the trace impedance is determined or calculated, then formula (5) can be used to calculate the impedance of the electrode arrays with or without cells present.

A method is invented in the present application to determine the impedance of electrical conductive (electrical connection) traces (mainly trace resistance, trace reactance is very small for the thin conductive film trace) based on the relationships among two or more essentially identical arrays on a cell-substrate impedance monitoring device. In the following, the four electrode arrays A, B, C and D as indicated in FIG. 1, are used to illustrate this method. The electrical reactance (serial reactance) of the electronic switches and the electrical reactance (serial reactance) of the electrical connection traces are small as compared with the corresponding electrical resistances (serial resistances). Thus, we focus on the analysis of the resistance of the electrical connection traces. The impedance determined from the impedance analyzer does contain both resistance (serial resistance, $R_{total}$) and reactance (serial reactance). For the electrode arrays A-D, the measured total resistance $R_{total}$, the resistance ($R_{trace}$) of electrical conductive (connection) trace, the switch resistance ($R_{switch}$) and the resistance ($R_{e-array}$) of the electrode array satisfy the following equations:

$$R_{e-array-A} = R_{total-A} - R_{trace-A} - R_{switch-A} \quad (6A)$$

$$R_{e-array-B} = R_{total-B} - R_{trace-B} - R_{switch-B} \quad (6B)$$

$$R_{e-array-C} = R_{total-C} - R_{trace-C} - R_{switch-C} \quad (6C)$$

$$R_{e-array-D} = R_{total-D} - R_{trace-D} - R_{switch-D} \quad (6D)$$

With chosen electronic switches having consistent switch-on resistance, $R_{switch-A}$, $R_{switch-B}$, $R_{switch-C}$ and $R_{switch-D}$ have very similar values and can be assumed to be the same, $R_{switch}$. Thus, in above equations, the known parameters are $R_{total-A}$, $R_{total-B}$, $R_{total-C}$ and $R_{total-D}$, and $R_{switch-A}$, $R_{switch-B}$, $R_{switch-C}$ and $R_{switch-D}$, and there are eight unknown parameters $R_{e-array-A}$, $R_{e-array-B}$, $R_{e-array-C}$ and $R_{e-array-D}$, and $R_{trace-A}$, $R_{trace-B}$, $R_{trace-C}$ and $R_{trace-D}$. It is impossible to solve these equations for the eight unknown variables from these four equations directly. Additional relationships between these variables are needed to solve for them. Each trace resistance ($R_{trace-A}$, $R_{trace-B}$, $R_{trace-C}$ and $R_{trace-D}$) depends on the metal film type used, and the geometry of the trace such as the how many rectangular segments the trace has, the film thickness(es) of the segments, the width(s) of the segments, the length(s) of the segment(s). For example, $$R_{trace-A} = \sum_{i=1}^{N} \rho \frac{L_{A-i}}{t_{A-i} * d_{A-i}} \quad (7)$$

where N is the number of the segments of the trace-A, $t_{A-i}$, $d_{A-i}$ and $L_{A-i}$ is the thickness, width and length of the i-th segment of the traces for the electrode array A, and $\rho$ is the resistivity of the thin film. The equation here applies to the film comprising a single type of metal. The equation can be readily modified to be applicable to the film comprising two or more metal types (e.g. gold film over chromium adhesion layer).

If the film thickness is reasonably uniform (for example, less than 10% in thickness variation) across the substrate, then the relationship among the trace resistances is simply determined by the pre-determined geometrical shapes (e.g. the length, width of the segments). For example, it would be straightforward to calculate the ratio $\alpha_{A-D}$ between the resistance of the electrically conductive traces for the electrode array A to the resistance of the electrically conductive traces for the electrode array D as below, where the film thickness is assumed to be the same everywhere on these traces and the resistivity is also the same everywhere on these traces, $$\alpha_{A-D} = \frac{R_{trace\_A}}{R_{trace\_D}} = \frac{\sum_{i=1}^{N} \rho \frac{L_{A-i}}{t_{A-i} * d_{A-i}}}{\sum_{i=1}^{M} \rho \frac{L_{D-i}}{t_{D-i} * d_{D-i}}} = \frac{\sum_{i=1}^{N} \frac{L_{A-i}}{d_{A-i}}}{\sum_{i=1}^{M} \frac{L_{D-i}}{d_{D-i}}}. \quad (8)$$

Similarly, one can determine the ratio $\alpha_{B-D}$ and $\alpha_{C-D}$ based on the pre-determined geometrical relationships for the traces of the electrode arrays B, C and D. Note that above equations can be similarly derived for the cases where the thin film in these traces comprises more than one metal type. Thus, based on the equalities $$R_{switch-A}=R_{switch-B}=R_{switch-C}=R_{switch-D}=R_{switch}, \quad (9A)$$

$$R_{trace-A}=\alpha_{A-D} \cdot R_{trace-D}, \quad (9B)$$

$$R_{trace-B}=\alpha_{B-D} \cdot R_{trace-D}, \quad (9C)$$

and $$R_{trace-C}=\alpha_{C-D} \cdot R_{trace-D} \quad (9D)$$

equations (6A)-(6D) can be re-written in the following format:

$$R_{e-array-A}=R_{total-A}-\alpha_{A-D} \cdot R_{trace-D}-R_{switch} \quad (10A)$$

$$R_{e-array-B}=R_{total-B}-\alpha_{B-D} \cdot R_{trace-D}-R_{switch} \quad (10B)$$

$$R_{e-array-C}=R_{total-C}-\alpha_{C-D} \cdot R_{trace-D}-R_{switch} \quad (10C)$$

$$R_{e-array-D}=R_{total-D}-R_{trace-D}-R_{switch-D} \quad (10D)$$

For equations (10A) through (10D), there are five unknown variables, $R_{e-array-A}$, $R_{e-array-B}$, $R_{e-array-C}$, and $R_{e-array-D}$ and $R_{trace-D}$. Mathematically, these unknown variables cannot be determined from these equations. Additional information is needed to solve for these variables $R_{e-array-A}$, $R_{e-array-B}$, $R_{e-array-C}$, and $R_{e-array-D}$ and $R_{trace-D}$.

One approach is invented and described in the present invention. In this approach, same biological or chemical solutions or suspensions are applied to the electrode-arrays A through D. Because the electrode arrays A through D have essentially identical electrode structures, the electrode array resistances $R_{e-array-A}$, $R_{e-array-B}$, $R_{e-array-C}$ and $R_{e-array-D}$ should be of same, or very similar value for such a condition when all the electrode arrays are exposed to the same biological or chemical solutions or suspensions i.e.: $R_{e-array-A} \approx R_{e-array-B} \approx R_{e-array-C} \approx R_{e-array-D}$. If we assume the averaged electrode array resistance is $R_{e-array}$, then these approximate relationship exists $R_{e-array-A} \approx R_{e-array-B} \approx R_{e-array-C} \approx R_{e-array-D} \approx R_{e-array}$. Thus, equations (10A-10D) can be changed to the following:

$$R_{e-array} \approx R_{total-A}-\alpha_{A-D} \cdot R_{trace-D}-R_{switch} \quad (11A)$$

$$R_{e-array} \approx R_{total-B}-\alpha_{B-D} \cdot R_{trace-D}-R_{switch} \quad (11B)$$

$$R_{e-array} \approx R_{total-C}-\alpha_{C-D} \cdot R_{trace-D}-R_{switch} \quad (11C)$$

$$R_{e-array} \approx R_{total-D}-R_{trace-D}-R_{switch-D} \quad (11D)$$

Thus, we would need to find $R_{trace-D}$ and $R_{e-array}$ that satisfy the above approximate equality as close as possible. One mathematical approach is to find $R_{trace-D}$ and $R_{e-array}$ that would result in the minimum value for the following expression—an expression that quantifies the differences between the two sides of the approximate equality in (11A, 11B, 11C and 11D), $$F(R_{trace-D}, R_{e-array})=[R_{e-array}-(R_{total-A}-\alpha_{A-D}R_{trace-D}-R_{switch})]^2+[R_{e-array}-(R_{total-B}-\alpha_{B-D}R_{trace-D}-R_{switch})]+[R_{e-array}-(R_{total-C}-\alpha_{C-D}R_{trace-D}-R_{switch})]^2+[R_{e-array}-(R_{total-D}-R_{trace-D}-R_{switch})]^2 \quad (12)$$

The expression $F(R_{trace-D}, R_{e-array})$ is the sum of the squared-differences between the two-sides of the approximate equality in (11A, 11B, 11C and 11D). The smaller $F(R_{trace-D}, R_{e-array})$, the closer the two sides of the approximate equality (11A, 11B, 11C and 11D). Thus, values of $R_{trace-D}$ and $R_{e-array}$ that result in the minimum value of $F(R_{trace-D}, R_{e-array})$ should be determined. Mathematical approach involves in the calculation of the first order derivative of $F(R_{trace-D}, R_{e-array})$ to $R_{trace-D}$ and to $R_{e-array}$ and let such first order derivatives equal to zero. The values of $R_{trace-D}$ and $R_{e-array}$ that result in zero for these first-order-derivatives are those that result in the minimum value of $F(R_{trace-D}, R_{e-array})$. The first order derivatives are as follows:

$$\frac{\partial[F(R_{trace-D}, R_{e-array})]}{\partial R_{trace-D}} = 2 \cdot \alpha_{A-D} \cdot [R_{e-array}-(R_{total-A}-\alpha_{A-D}R_{trace-D}-R_{switch})] + 2 \cdot \alpha_{B-D} \cdot [R_{e-array}-(R_{total-B}-\alpha_{B-D}R_{trace-D}-R_{switch})] + 2 \cdot \alpha_{C-D} \cdot [R_{e-array}-(R_{total-C}-\alpha_{C-D}R_{trace-D}-R_{switch})] + 2 \cdot [R_{e-array}-(R_{total-D}-R_{trace-D}-R_{switch})] = 0; \quad (13A)$$

$$\frac{\partial[F(R_{trace-D}, R_{e-array})]}{\partial R_{e-array}} = 2 \cdot [R_{e-array}-(R_{total-A}-\alpha_{A-D}R_{trace-D}-R_{switch})] + 2 \cdot [R_{e-array}-(R_{total-B}-\alpha_{B-D}R_{trace-D}-R_{switch})] + 2 \cdot [R_{e-array}-(R_{total-C}-\alpha_{C-D}R_{trace-D}-R_{switch})] + 2 \cdot [R_{e-array}-(R_{total-D}-R_{trace-D}-R_{switch})] = 0. \quad (13B)$$

Equations (13A) and (13B) can be re-written as $$R_{e-array} \cdot [\alpha_{A-D}+\alpha_{B-D}+\alpha_{C-D}+1]+R_{trace-D} \cdot [\alpha_{A-D}^2+\alpha_{B-D}^2+\alpha_{C-D}^2+1] = \alpha_{A-D} \cdot [R_{total-A}-R_{switch}]+\alpha_{B-D} \cdot [R_{total-B}-R_{switch}]+\alpha_{C-D} \cdot [R_{total-C}-R_{switch}]+[R_{total-D}-R_{switch}] \quad (14A)$$

$$4 \cdot R_{e-array}+R_{trace-D} \cdot [\alpha_{A-D}+\alpha_{B-D}+\alpha_{C-D}+1]=[R_{total-A}-R_{switch}]+[R_{total-B}-R_{switch}]+[R_{total-C}-R_{switch}]+[R_{total-D}-R_{switch}] \quad (14B)$$

Thus, we can solve for $R_{trace-D}$ as follows:

$$R_{trace-D} = \frac{4 \cdot S_1 - A_{11} \cdot S_2}{4 \cdot A_{12} - A_{11} \cdot B_{12}} \quad (15)$$

where $$A_{11} = [\alpha_{A-D} + \alpha_{B-D} + \alpha_{C-D} + 1];$$

$$A_{12} = [\alpha_{A-D}^2 + \alpha_{B-D}^2 + \alpha_{C-D}^2 + 1];$$

$$S_1 = \alpha_{A-D} \cdot [R_{total-A} - R_{switch}] + \alpha_{B-D} \cdot [R_{total-B} - R_{switch}] + \alpha_{C-D} \cdot [R_{total-C} - R_{switch}] + [R_{total-D} - R_{switch}];$$

-continued $$B_{12} = [\alpha_{A-D} + \alpha_{B-D} + \alpha_{C-D} + 1];$$

$$S_2 = [R_{total-A} - R_{switch}] + [R_{total-B} - R_{switch}] +$$
$$[R_{total-C} - R_{switch}] + [R_{total-D} - R_{switch}].$$

Thus, with the determined $R_{trace-D}$ the trace resistances of $R_{trace-A}$, $R_{trace-B}$, and $R_{trace-C}$ can be calculated using equations (9B), (9C) and (9D). Furthermore, the electrode array resistance $R_{e-array-A}$, $R_{e-array-B}$, $R_{e-array-C}$ and $R_{e-array-D}$ can be calculated from the measured resistance $R_{total-A}$, $R_{total-B}$, $R_{total-C}$ and $R_{total-D}$ respectively using equations (10A), (10B), (10C) and (10D).

Thus, one aspect of the present invention is directed to a method of calculation of the resistances of the electrical connection traces s from the measured, total resistances for two or more essentially identical electrode arrays, comprising the following steps:
 (1) exposing the electrode arrays to the solutions having same or similar solutions or suspensions;
 (2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses), and the resistance of the electrode array with the solutions or suspensions present;
 (3) solving for the resistances of electrical connection traces using equation (15) and equations (9B), (9C) and (9D), noting in the calculation with equation (15), the geometrical relationships between the electrode arrays are used to determine the factor $\alpha_{A-D}$, $\alpha_{B-D}$ and $\alpha_{C-D}$.

Another aspect of the present invention is directed to a method of calculating the resistance of the electrode arrays from the measured, total electrode resistances for two or more essentially identical electrode arrays if the same or similar solutions or suspensions are added to be in contact with the electrode assays, comprising the following steps:
 (1) exposing the electrode arrays to the solutions having same or similar solutions or suspensions;
 (2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses) and the resistance of the electrode arrays with the solutions or suspensions present;
 (3) solving for the resistances of electrical connection traces using equation (15) and equations (9B), (9C) and (9D), noting in the calculation with equation (15), the geometrical relationships between the electrode arrays are used to determine the factor $\alpha_{A-D}$, $\alpha_{B-D}$ and $\alpha_{C-D}$;
 (4) calculating the resistances of the electrode arrays using equations (10A, 10B, 10C and (10D)).

In many applications, the solutions or suspensions (for example, cell suspension) applied to each electrode array may have different compositions. For example, cell suspensions of different cell numbers may be used so that the suspensions applied to each electrode array are quite different. Under such cases, the determination of the resistance of the electrode arrays with the cells present would require the determination of the resistance of the electrical connection traces by performing a "reference run" or "calibration run" in which the electrode arrays are exposed to a same, reference solution. From the "reference run", the resistances of the electrical connection traces can be determined. In a separate test, the electrode arrays are exposed to the solutions or cell suspensions of interest and the resistances for the electrode arrays under such conditions are measured with an impedance analyzer or impedance measuring circuit. The resistance of the electrode arrays with such cell suspensions present can be determined (or continuously determined) from the measured resistance by subtracting the sum of the resistance of the electronic switches and the resistance of the electrical connection traces for corresponding electrode arrays from the measured resistances.

Thus, another aspect of the present invention is directed to a method of calculating the resistance of the electrode arrays from the total electrical resistances measured at an impedance analyzer for essentially identical electrode arrays if different solutions or suspensions of interest are applied to the electrode assays, comprising the following steps:
 (1) exposing the electrode arrays to the solutions having same or similar solutions or suspensions (reference solutions);
 (2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses) and the resistance of the electrode arrays with the reference solutions present;
 (3) solving for the resistances of electrical connection traces using equation (15) and equations (9B), (9C) and (9D), noting in the calculation with equation (15), the geometrical relationships between the electrode arrays are used to determine the factor $\alpha_{A-D}$, $\alpha_{B-D}$ and $\alpha_{C-D}$;
 (4) applying the solutions or suspensions of interest to each electrode array; and with an impedance analyzer or impedance measurement circuit, measuring the resistance (serial resistance) of each electrode array, such resistance being the sum of the resistance of electronic switches, the resistance of the electrical connection traces between the connection pads and the electrode structures, the resistance of the electrode arrays with the solutions or suspensions of the interest present,
 (5) Calculating the resistance of the electrode arrays using equations (10A), (10B), (10C) and (10D) by subtracting the electronic switch resistances and the resistances of electrical connection traces from the measured resistances in the step (4).

Note that in above method, the steps of exposing the electrode arrays to reference solutions for the determination of the resistances of electrically conductive traces (step (1), (2) and (3)) may be performed before or after the steps of applying the solutions or suspensions of interest to the electrode arrays and measuring the total electrical resistance (step (4)). For example, step (4) may be performed first. After that, the solutions or suspensions of the interest may be removed from the electrode array. The reference solutions can then be added to the electrode arrays (step (1)). Step (2) and step (3) can be then performed to determine the resistances of electrical connection traces. Finally, Step (5) can be done.

In another approach, step (1) and (2) can be performed ahead of step (4).

Another aspect of the present invention is directed to a method of determining the resistance of the electrode arrays with the cells present for a cell-based assay based on the total electrical resistance measured at an impedance analyzer for essentially identical electrode arrays. In this method, the electrode arrays are exposed to a same, reference solution (for example, a same cell culture medium that does not contain any cells) and electrical measurement is conducted to determine the resistance of electrical connection traces. With the resistances of the electrical connection traces determined, electrical resistances of the electrode arrays with cell suspensions added to electrode arrays can be calculated from the total electrical resistances measured at an impedance analyzer. Such total electrical resistance would include the resistance of the electrode arrays with cells present, the resistance of electronic switches and the resistance of electrical connection traces. The method comprises following steps (1) exposing the electrode arrays to the solutions having same or similar solutions or suspensions (reference solutions);
(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses) and the resistance of the electrode arrays with the reference solutions present;
(3) solving for the resistances of electrical connection traces using equation (15) and equations (9B), (9C) and (9D), noting in the calculation with equation (15), the geometrical relationships between the electrode arrays are used to determine the factor $\alpha_{A-D}$, $\alpha_{B-D}$ and $\alpha_{C-D}$;
(4) applying the cell suspensions of interest to each electrode array; and with an impedance analyzer or impedance measurement circuit, measuring the resistance (serial resistance) of each electrode array, such resistance being the sum of the resistance of electronic switches, the resistance of the electrical connection traces between the connection pads and the electrode structures, the resistance of the electrode arrays with the cell suspensions of the interest present,
(5) Calculating the resistance of the electrode arrays using equations (10A), (10B), (10C) and (10D) by subtracting the electronic switch resistances and the resistances of electrical connection traces from the measured resistances in step (4).

Note that in above method, the steps of exposing the electrode arrays to reference solution for the determination of the electrical resistance of electrically conductive traces (step (1), (2) and (3)) may be performed before or after the steps of applying the solutions of interest or cell suspensions of interest to the electrode arrays and measuring the total electrical resistance (step (4)). For example, step (4) may be performed first, followed by steps (1) and (2). In one approach, after step (4), the cell suspensions of the interest may be removed from the electrode array. Then reference solutions can be added to the electrode arrays. In another approach, after step (4), the cells are all lysed with some cell lysis solutions so that the electrodes are exposed to the same, reference solutions for the measurement and calculation of step (2) and (3). And then, step (5) is performed to determine the electrical resistance of electrode arrays with the cell suspensions of interest present.

The determination of the resistances of the electrical conductive traces for the electrode arrays that essentially identical electrode arrays may be, or may not be, part of the monitoring of cell-substrate impedance for cell-based assays. It depends on how the impedance data (measured at a single frequency or multiple frequencies, measured at multiple time points) of the electrode arrays is analyzed.

In some assays, one is interested in the relative change in the resistance or impedance of the electrode arrays with the cells present relative to the baseline resistance or impedance. For such cases, it is preferred to determine the resistance (or impedance) of the electrode arrays from the total, measures resistance (or impedance) by subtracting the resistance of the electrical conductive traces and the resistance of electronic switches. Thus, determination of the resistances or impedance of the electrically conductive traces may be required.

In some other assays, one is interested in the absolute changes in the resistance (or impedance) of the electrode arrays with cells present relative to the baseline resistance (or impedance). In these cases, one can directly subtract the measured resistance or impedance for the baseline condition from the measured resistance or impedance for the condition that the cells are present on the electrode arrays. The contribution of the resistance (or impedance) of the electronic switches and the resistance (or impedance) of the electrically conductive traces to the total measured resistance (or impedance) values is cancelled out in such subtractions. Thus, there is no need for determining the resistances of the electrically conductive traces.

In some assays, one is interested in calculating the Cell Index or Cell Number Index based on the monitored impedance values. Depending on which method is used for calculating the Cell Index, it may, or may not, be necessary to determine the resistances of the electrically conductive traces. For example, for the Cell Index calculation method (A) described above, the resistances of the electrically conductive traces are needed, in order to remove the effect of the resistance of the electrically conductive traces on the analysis of the relative change of the resistance or impedance. In another example, for the Cell Index calculation method (F) described above, there is no need to determine the resistances of the electrically conductive traces since the effect of the resistance of the electrically conductive traces is canceled out in the calculations.

The monitoring of the cell-substrate impedance may be or may not be based on the change with respect to the baseline impedance (or resistance). For example, a cell-based assay is performed to assess the effect of a test compound on the cells. One method in performing such an assay is by monitoring of the cell-substrate impedance and determining the change in the cell-substrate impedance before and after the addition of the test compound to the cells. The monitoring of cell-substrate impedance can be performed at a single frequency point or multiple frequency points, at a single time point or multiple time points after drug addition. For example, the impedance is first measured at a single frequency or multiple frequencies for the electrode arrays with the cells present just before addition of test compound. The test compound is then added to the cells. The impedance is then measured again at the same single frequency or multiple frequencies for the electrode arrays with the cells after the addition of test compound. Such post-compound addition measurement may be performed for many time points continuously in a regular or irregular time intervals. The change in the cell-substrate impedances can be determined or quantified by subtracting the impedance(s) (resistance and/or reactance) measured before addition of the test compound from the impedance(s) (resistance and/or reactance) measured after addition of the test compound. If the measurement is done at multiple frequencies, a single parameter or multiple parameters may be further derived for each time point after compound addition based on the calculated change in the cell-substrate impedances. Such parameters are used to quantify the cell changes after compound addition. Such approaches can be used further to analyze the responses of the cells to a test compound at multiple concentrations to derive dose-dependent response curves.

Similarly, impedance may be monitored prior to electroporating a cell or cell population. Impedance monitoring may provide information regarding the viability of the cells and may determine whether the cells will be used for an experiment or whether a new cell or cell population is necessary. Thus, monitoring or measuring impedance may function as a quality control.

Also, impedance may be monitored after electroporating a cell or cell population. Impedance monitoring may provide information regarding the effect of molecules that are introduced or transfected to cells on cellular processes or cell properties.

In addition, impedance may be monitored before or after or before and after electrostimulating a cell or cell population. Electrostimulating a cell or cell population is done by applying appropriate electrical voltage signals to electrostimulation electrodes to affect cell membrane potential, thus affecting a voltage gated ion channel in cell membranes.

Normalized Cell Index, Delta Cell Index

A "Normalized Cell Index" at a given time point is calculated by dividing the Cell Index at the time point by the Cell Index at a reference time point. Thus, the Normalized Cell Index is 1 at the reference time point. Normalized cell index is cell index normalized against cell index at a particular time point. In most cases in the present applications, normalized cell index is derived as normalized relative to the time point immediately before a compound addition or treatment. Thus, normalized cell index at such time point (immediately before compound addition) is always unit one for all wells. One possible benefit for using such normalized cell index is to remove the effect from difference in cell number in different wells. A well having more cells may produce a larger impedance response following compound treatment. Using normalized cell index, it helps to remove such variations caused by different cell numbers.

A "delta cell index" at a given time point is calculated by subtracting the cell index at a standard time point from the cell index at the given time point. Thus, the delta cell index is the absolute change in the cell index from an initial time (the standard time point) to the measurement time.

Cell Change Index

The time-dependent cellular response (including cytotoxicity response) may be analyzed by deriving parameters that directly reflect the changes in cell status. For example, time dependent cellular response may be analyzed by calculating the slope of change in the measured impedance responses (that is equivalent to the first order derivative of the impedance response with respect to time, impedance response here can be measured impedance data or derived values such as cell index, normalized cell index or delta cell index). In another example, the time-dependent cellular responses (including cytotoxic responses) responses may be analyzed for their higher order derivatives with respect to time. Such high order derivatives may provide additional information as for how cells responding to different compounds and as for the mechanisms of compound action.

As an example, we describe how one can to derive a parameter, called Cell Change Index, based on the real time, quantitative information (i.e., cell index, CI) about biological status of cells in the wells provided from RT-CES system. This new parameter, Cell Change Index (CCI), can effectively link time dependent cell index I with cell status, is calculated as, $$CCI(t) = \frac{dCI(t)}{CI(t) \cdot dt}. \quad (5)$$

Thus CCI is the normalized rate of change in cell index. CCI values can be used to quantify the cell status change. For cells in an exponential growth under regular cell culture condition, the cell index determined by a cell-substrate impedance monitoring system described herein is expected to be a proportionate measure of the cell number in the well since the cell morphology and average extent of cell adhesion to the electrode surfaces among the whole cell population do not exhibit significant changes over time. Thus, the cell index (CI) increase with time following an exponential function, such that $$CI(t) = CI(0) * 2^{\frac{t}{DT}} \quad (6)$$

where DT is the cell doubling time. For such exponential growth culture, CCI(t) is a constant, giving $$CCI(t) = \frac{0.693}{DT} \approx \frac{0.7}{DT}. \quad (7)$$

Thus, several types of CCI(t) can be classified as:
(1) If CCI is about 0.7/DT, cell index increases in the same rate as that expected for an exponential growth of the cells.
(2) If CCI>>0.7/DT, cell index increases faster than that expected for an exponential growth (or log growth) of the cells. This indicates that cells may grow faster than regular exponential growth, or cells may exhibit some morphology change (e.g. cell spreading out or adhering better to the electrode surfaces), leading to large impedance signal, or both of above effects, or there may be other cell behaviors occurring particular to the assay or culture conditions.
(3) If CCI is more than zero but somewhat smaller than 0.7/DT, then cell index increases in the rate slowed than that expected for an exponential growth. This indicates that cell growth rate may be slowed down relative to exponential growth, or cell growth may be somewhat inhibited by chemical compounds added to the culture media or by other cell culture parameters, or that certain populations of cells are dying off and detaching from the electrode surfaces, or there may be other cell behaviors occurring particular to the assay or culture conditions.
(4) If CCI is about zero, then cell index shows a near constant value. This may indicate that the cell growth is nearly-completely inhibited. For example, all the cells are arrested at certain points of cell cycle and are not progressing further. Or, this may indicate that the number of cells dying off in the culture is nearly as the number of newly-divided cells. Alternatively this may indicate that cells reach stationary phase of cell culture. Alternatively this may indicate that number of cells are above the detection upper limit of the cell-substrate impedance monitoring system. There is also the possibility of other cell behaviors occurring particular to the assay or culture conditions.
(5) If CCI is negative, then the cell index is decreasing with time, showing the cells losing attachment to the electrode surface or changing their morphology.

(6) If CCI is very negative, then the cell index decreases rapidly with time, showing that either cells lose attachment to the electrode surfaces quickly or cells change their morphology very quickly.

D. Methods for Performing Real-Time Cell-Based Assays

The present invention provides a method of monitoring a cellular response in real time, comprising, transfecting a cell or cell population with a molecule and monitoring impedance of said cell or said cell population. The monitoring of impedance of cell or cell population may be performed prior to transfection of cells with molecules, or after transfection of cells with molecules, or prior to and after transfection of cells with molecules. The present invention provide cell-based assays that can be performed in real time to assess cell proliferation, cell growth, cell death, cell morphology, cell membrane properties (for example, size, morphology, or composition of the cell membrane) cell adhesion, cell spreading and/or cell motility and to assess the effects of transfected molecules in cells on cell proliferation, cell growth, cell death, cell morphology, cell membrane properties (for example, size, morphology, or composition of the cell membrane) cell adhesion, cell spreading and/or cell motility. Thus the assays can be cytotoxicity assays, proliferation assays, apoptosis assays, cell adhesion assays, cell activation or stimulation assays, anti-cancer compound efficacy assays, receptor-ligand binding or signal transduction analysis, assays of cytoskeletal changes, assays of cell structural changes (including but not limited to, changes in cell membrane size, morphology, or composition), cell quantification, cell quality control, time-dependent cytotoxicity profiling, assays of cell differentiation or de-differentiation, detection or quantitation of neutralizing antibodies, specific T-cell mediated cytotoxic effect assays, assays of cell adhesion or spreading, assays of cell-cell interactions, analysis of microbial, viral, or environmental toxins, etc. In particular, the present invention permits the investigation of the effects of introducing molecules or macromolecules into the cells in these different cell-based assays. The molecules or macromolecules include, but not limited to, DNA molecules (in the form of plasmids, cDNA, linear DNA, oligos or anti-sense DNA stands) RNA molecules (in the form of siRNA, mRNA, shRNA, ribozymes, RNAi,) aptamers, proteins (antibodies, polypeptides, peptides or fragment of proteins), compounds (fluorescent dyes, small molecular inhibitors of specific proteins). The method of introduction of these molecules or macromolecules into the cells, collectively referred to as transfection, may include but is not limited to chemical and lipid-mediated transfection, electroporation, viral-mediated infection and microinjection.

For example, if the role of a particular receptor tyrosine kinase needs to be assessed in cell proliferation, then either an siRNA, shRNA, mRNA, cDNA encoding for dominant negative version of the receptor, an inhibitory antibody, protein fragment, peptide or a small molecular inhibitor maybe introduced into the cell by any or combination of the methods mentioned above and the effect of such reagents can then be assessed on cell proliferation using the present invention. This assay will be performed using the following method: 1) cells expressing the specific growth factor receptors are introduced using any one of the methodologies described above with any one or combination of molecules or macromolecules which target the receptor physically or functionally, 2) impedance of the transfected cells is monitored prior to and after the introduction of the molecules or macromolecules and is compared with impedance of the control cells that have not been treated with any molecules or macromolecule or or introduced with control molecules or macromolecules that do not have direct effects on the receptor of interest. Preferably, the impedance of transfected cells and the control cells is monitored at multiple time points. For the transfected cells, the molecules and macromolecules transfected will functionally or physically interfere with the function of the receptor tyrosine kinase of interest. Thus, if such receptor tyrosine kinase plays an important role in cell growth and proliferation, then growth or proliferation of the transfected cells will be expected to be reduced significantly, as compared with control cells which were transfected with control molecules or macromolecules.

In another example, if an orphan GPCR is being validated as a target for a particular agonist or ligand, then specific inhibitory molecules such as siRNA, mRNA, shRNA or a cDNA encoding a dominant negative version of the receptor of interest is introduced into a cell which is expressing the particular receptor. The inhibitory molecules are expected to interfere with either the expression or function of the GPCR and inhibit its activation by its cogante ligand. As a control, the cells are also transfected with a control molecule. The activation of the receptor by addition of the particular agonist or ligand can be monitored using impedance at various time points after addition of the agonist or ligand to the cells transfected with inhibitory molecules. If the GPCR of interest does serve as the receptor for the identified agonist or ligand then interfering with its function or expression is expected to prevent activation of the cell as monitored by impedance measurement. Cells transfected with the control molecules should respond to the agonist or ligand. Using cell-substrate impedance sensing to monitor activation of GPCR has been disclosed in U.S. patent application Ser. No. 11/198,831, entitled, "Dynamic Monitoring of Activation of G-Protein Coupled Receptor (GPCR) and Receptor Tyrosine Kinase (RTK) in Living Cells using Real-Time Microelectronic Cell Sensing Technology, filed on Aug. 4, 2005, which is herein incorporated by reference in its entirety.

Alternatively, a complimentary method to test whether a particular GPCR can serve a receptor for a particular agonist or ligand is to transfect the cDNA encoding for the GPCR in a cell line which does not express the receptor of interest. Two basic methods can be employed to express the receptor. In the first method a cell line stably expressing the receptor could be established. Alternatively, the receptor can be transfected transiently in the cell line. As a control, the cells can be stably or transiently transfected with a control cDNA. The functional activation of the transient or stably expressed receptor in response to the agonist or ligand can be assessed using impedance readout. If the ligand or agonist does bind and activate the receptor, then it is expected that it would activate the cells as monitored by impedance. The control cells should not respond to the ligand. Again, using cell-substrate impedance sensing to monitor activation of GPCR has been disclosed in U.S. patent application Ser. No. 11/198,831, entitled, "Dynamic Monitoring of Activation of G-Protein Coupled Receptor (GPCR) and Receptor Tyrosine Kinase (RTK) in Living Cells using Real-Time Microelectronic Cell Sensing Technology, filed on Aug. 4, 2005, which is herein incorporated by reference in its entirety.

In another example if the role of a signaling protein is being determined in cell adhesion and spreading assays, then molecules such as siRNA, shRNA, anti-sense DNA stand, or cDNA encoding a dominant negative version of the protein of interest can be transfected into the cell by said methods. The cells will be transfected in regular tissue culture dishes, incubated with the inhibitory molecule for a given optimal time point and detached and then re-seeded on special plates which contain electronic sensors integrated in the bottom of the well for the detection of cell impedance. The attachment and spreading of the cells will be monitored by impedance measurements. As a control the impedance of cells transfected with a control molecule or non-transfected cell will be monitored concomitantly. If the function of the protein is necessary for cell attachment and spreading, it is expected interfering with its function by any of the indicated methods should significantly hamper the attachment and spreading of the cells as monitored using impedance readout. The attachment and spreading of the transfected cell will be compared with a control cell which should display normal attachment and spreading. The method for applying cell-substrate impedance sensing for cell adhesion and spreading has been disclosed in U.S. patent application Ser. No. 11/235,938, entitled, "Dynamic Monitoring of Cell Adhesion and Spreading Using the RT-CES System", filed on Sep. 27, 2005, which is incorporated by reference in its entirety.

In yet another example, if the function of a receptor on target cells needs to be tested in mediating the cytotoxic effect of effector cells, such as natural killer cells (NK), cytotoxic T lymphocytes (CTLs), or PBMCs, then molecules such as siRNA, shRNA, anti-sense DNA, aptamers, and antibodies targeting the receptor of interest can be transfected into the target cells by a transfection method such as chemical or viral or electroporation-based transfection method. For example, the transfection can be directly carried out using electroporation methods on the plates that are integrated with the microelectrodes. After waiting for a specified period of time to allow the inhibitory molecule to take effect, then the effector cells can be added to the target cells growing in the bottom of the well in the plates. As a control, the target cells can also be transfected with a control molecule that has no effect on the protein of interest. If the receptor of interest is involved in mediating the cytotoxic activity of the effector cells upon target cells, then interfering with its function or expression should block to a significant degree the cytotoxic effect of effector cells upon target cells. The control cells would be expected to undergo cytotoxicity and as a result the cell-substrate impedance is expected to decrease over time. The cells transfected with the inhibitory molecules are expected to be resistant to the effector cells mediated cytotoxicity. The method for applying cell-substrate impedance sensing in monitoring effector-cell mediated cytotoxicity has been disclosed in U.S. patent application Ser. No. 11/197,994, entitled, "Method for Assaying for Natural Killer, Cytotoxic T-Lymphocyte and Neutrophil-Mediated Killing of Target Cells Using Real-Time Microelectronic Cell Sensing Technology", filed on Aug. 4, 2005, which is incorporated by reference in its entirety.

In yet another example the combination of transfection and impedance measurements can be used for target-validation assessment of a target molecule (e.g., a protein) in the cells that may be involved in cytotoxicity. The experiment would be performed by transfecting molecules to the cells using a transfection method. The transfected molecules inhibit or interfere with the expression or function of the target of interest. Once, it is determined that the target molecule is sufficiently compromised in terms of its expression or function, then a cytotoxic agent, such anti-miotics or DNA damaging agents can be added to the cells and the degree of cytotoxicity taking place can be evaluated by impedance measurements. As a control, the target cells can be transfected with a control molecule which does not affect the target molecule. If the target molecule is involved in mediating cytotoxicity, then its ablation or interfering with its function should curtail the effect of the cytotoxic agent. As an additional control, cells transfected with the inhibitory molecules will be left untreated to ascertain that the mere down-regulation or inhibition of target function does not affect cell viability. Application of cell-substrate impedance sensing for cytotoxicity assays has been disclosed in U.S. patent application Ser. No. 11/055,639, entitled "Real time electronic cell sensing system and applications for cytotoxicity profiling and compound assays" filed on Feb. 9, 2005, which is incorporated by reference in its entirety.

The assays are real-time assays in the sense that cell behavior or cell status being assayed can be assessed continuously at regular or irregular intervals. Cell behaviors, cell responses, or cell status can be assayed and the results recorded or displayed within seconds to minutes of their occurrence. The cell response during an assay can be monitored essentially continuously over a selected time period. For example, a culture can be monitored every five to fifteen minutes for several hours to several days before or after addition of a reagent. The interval between impedance monitoring, whether impedance monitoring is performed at regular or irregular intervals, and the duration of the impedance monitoring assay can be determined by the experimenter.

Thus, the cell-based impedance assays of the present invention avoid inadvertently biased or misleading evaluation of cell responses due to the time point or time points chosen for sampling or assaying the cells. In addition, the assays do not require sampling of cell cultures or addition of reagents and thus eliminate the inconvenience, delay in obtaining results, and error introduced by many assays.

Descriptions of cell-substrate monitoring and associated devices, systems and methods of use have been provided in U.S. provisional application No. 60/379,749, filed on Jul. 20, 2002; U.S. provisional application No. 60/435,400, filed on Dec. 20, 2002; U.S. Provisional application 60/469,572, filed on May 9, 2003, PCT application number PCT/US03/22557, entitled "Impedance based devices and methods for use in assays", filed on Jul. 18, 2003; PCT application number PCT/US03/22537, entitled "Impedance based apparatuses and methods for analyzing cells and particles", filed on Jul. 18, 2003; U.S. patent application Ser. No. 10/705,447, entitled "Impedance based devices and methods for use in assays", filed on Nov. 10, 2003; U.S. patent application Ser. No. 10/987,732 U.S. patent application Ser. No. 10/705,615, entitled "Impedance based apparatuses and methods for analyzing cells and particles", filed on Nov. 10, 2003, all incorporated herein by reference for their disclosure of cell-substrate impedance devices, systems, and methods of use. Additional details of cell-substrate impedance monitoring technology is further disclosed in the present invention.

In brief, for measurement of cell-substrate or cell-electrode impedance using the technology of the present invention, cell-substrate impedance monitoring devices are used that have microelectrode arrays with appropriate geometries fabricated onto the bottom surfaces of wells such as microtiter plate wells, or have a similar design of having multiple fluid containers (such as wells) having electrodes fabricated on their bottom surfaces facing into the fluid containers. Electroporation or electrostimulation electrodes with appropriate geometries and configurations may also be microfabricated or incorporated. Cells are introduced into the fluid containers of the devices, and make contact with and attach to the electrode surfaces. Cells or cell populations may be transfected with molecules using any appropriate method such as chemical, thermal, viral, or electroporation-assisted methods. The cell membrane potential may be affected resulting in modulation of a voltage gated ion channel. The presence, absence or change of properties of cells affects the electronic and ionic passage on the electrode sensor surfaces. Measuring the impedance between or among electrodes provides important information about biological status of cells present on the sensors. When there are changes to the biological status of the cells analogue electronic readout signals can be measured automatically and in real time, and can be converted to digital signals for processing and for analysis.

Preferably, cell-substrate impedance assays are performed using a system of the present invention that comprises a device of the present invention, an impedance monitor, a device station that comprises electronic circuitry and engages the device and the impedance analyzer, and a software program that controls the device station and records and analyzes impedance data.

Using a system of the present invention, a cell index can optionally be automatically derived and provided based on measured electrode impedance values. The cell index obtained for a given well reflects: 1) how many cells are attached to the electrode surfaces in this well, and 2) how well (tightly or extensively) cells are attached to the electrode surfaces in this well. Thus, the more the cells of same type in similar physiological conditions attach the electrode surfaces, the larger the cell index. And, the better the cells attach to the electrode surfaces (e.g., the cells spread-out more to have larger contact areas, or the cells attach tighter to electrode surfaces), the larger the cell index.

In another aspect of the present invention, a method is provided for performing cell-based assays, comprising: a) providing a cell-substrate impedance monitoring device of the present invention that comprises two or more electrode arrays, each of which is associated with fluid containers of the device; b) providing a set of electroporation electrodes; c) attaching the device to an impedance monitor; c) introducing cells into one or more fluid containers of the device; d) electroporating cells to allow introduction of a compound or molecule into the cells by applying appropriate electrical voltage signals to the set of electroporation electrodes; and e) monitoring cell-substrate impedance of at least one of the fluid containers that comprises an electrode array and cells. Compounds or molecules to be introduced into the cells by electroporation method may be any suitable molecules such as biomolecules, proteins, polypeptides, nucleic acid molecules, RNAi, siRNA, mRNA, DNA, cDNA, organic compounds and the like. Impedance may also be monitored prior to transfecting the cells. Preferably, impedance is monitored from the at least one fluid container to obtain impedance measurements at least three time points. Preferably, impedance measurements or impedance values derived from impedance measurements from at least three time points are plotted versus time to generate one or more impedance curves for the one or more fluid containers. In a preferred embodiment of the method, the set of electroporation electrodes is also associated with fluidic containers of the device so that at least one fluidic container comprises a set of electroporation electrodes. In this preferred embodiment, cell electroporation and cell-substrate impedance monitoring take place in the same fluidic containers. In other embodiments, the sets of electroporation electrodes is not associated with fluidic containers of the devices. Cells are electroporated in different devices from those used for monitoring cell-substrate impedance. After cells are electroporated to be transfected with molecules of interest, the cells are introduced into one or more fluidic containers.

In a related aspect of the present invention, a method is provided for performing cell-based assays in an impedance-monitoring system, comprising: a) providing a cell-substrate impedance monitoring system of the present invention that comprises a device having two or more electrode arrays; b) introducing cells into one or more wells of the device; c) electrostimulating cells to induce a change in the cell membrane potential; and c) monitoring cell-substrate impedance of at least one of the wells that comprises an electrode array and cells. The method may further comprise adding a test compound into the one or more wells of the device containing the cells prior to (or after) inducing a change in cell membrane potential. The test compound may be or is suspected to be ion channel inhibitor or ion channel blocker or stimulator. Monitoring cell-substrate impedance may provide information on cell responses to electrostimulation. For example, if the change in cell membrane potential leads directly to a change in cell morphology or cell adhesion on the electrode surfaces, then the cell-substrate impedance can be used to monitor cell responses to an electrostimulation. Or, if the change in cell membrane potential results in opening or closing of certain voltage-gated ion channels and if the opening or closing of such voltage-gated ion channels causes a change in cell morphology or cell adhesion on the electrode surfaces, then the cell-substrate impedance can be used to monitor the activities of the voltage-gated ion channels. The method may further comprise monitoring ion-channel-activity associated parameters using fluorescent or other optical methods. For example, membrane potential-sensitive fluorescent dyes may be added to the cells prior to inducing a change in the membrane potential. The time-dependent change in cell membrane potential after electrostimulating the cells may be monitored by measuring the fluorescent intensity of the membrane potential-sensitive fluorescent dyes. The time-dependent change in cell membrane potential may depend on activities of voltage-gated ion channels. Thus, the effect of the test compound on ion-channel activity can be analyzed by comparing the time-dependent change in cell membrane potential after electrostimulating the cells with or without the presence of the test compound. Similarly the dose-response effect of the test compound can also be determined by having different concentrations of the test compound in the well when cell electrostimulation is conducted. In another example, a calcium-specific dye may be used to monitor the activity of certain voltage-gated, calcium channels after electrostimulating the cells. After the cells are electrostimulated leading to a change in cell membrane potential, there may be specific responses of voltage-gated, calcium channels. The activity of such channels may lead to a transient change in intracellular calcium concentration, which can be monitored using calcium-specific, fluorescent dye. Similar to the case of using membrane potential sensitive dye, the effect of a test compound on the voltage gated, calcium ion channels can be monitored and analyzed. Preferably, impedance is monitored from the one or more wells of the device to obtain impedance measurements using at least three time points. Preferably, impedance measurements or impedance values derived from impedance measurements from at least three time points are plotted versus time to generate one or more impedance curves for the one or more wells.

The method can be used to assay cell status and to assay the effect of transfected molecules on cell status or cellular property and to assay the effect of electrostimulation on cell status or cellular property, where cell status includes, but is not limited to, cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well;

cytoskeleton change and re-organization and number of cells going through apoptosis and/or necrosis. The cell-based assays that can be performed with above methods include, but are not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, and cell-based assays for screening and measuring ligand-receptor binding. A variety of assays to monitor transcription or translation may also be performed. These assays can further provide information about the effect of the transfected molecules on cells or in a variety of cellular processes including cell adhesion, cell death, cell differentiation, cell proliferation, cell survival, cytotoxicity, cell morphology dynamics, cytotoxicity response, IgE-mediated cell activation or stimulation, receptor-ligand binding, ligand-induced receptor activation j, viral and bacterial toxin mediated cell pathologic changes and cell death, specific T-cell mediated cytotoxic response.

The cells used in the assay can be primary cells isolated from any species or cells of cell lines. Primary cells can be from blood or tissue. The cells can be engineered cells into which nucleic acids or proteins have been introduced. In some embodiments, different cell types are added to different wells and the behavior of the cell types is compared.

An impedance monitoring assay can be from seconds to minutes to days or even weeks in duration. Preferably, impedance is monitored at three or more time points, although this is not a requirement of the present invention. Impedance can be monitored at regular or irregular time intervals, or a combination of irregular and regular time intervals. In one embodiment of a cell-based impedance assay, the cell-substrate impedance is monitored at regular time intervals. In some embodiments of the present invention, impedance is monitored at irregular intervals and then at regular intervals during a particular time window of the assay. Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

In yet another aspect, the present invention provides a method for performing real-time cell-based assay investigating the effect of a compound on cells, comprising: a) providing an above described system; b) seeding the cells to the wells of multiple-well devices; c) adding a compound to the wells containing cells; d) monitoring cell-substrate impedance before and after adding the compound at a regular or irregular time interval; wherein the time dependent impedance change provides information about time dependent cell status before addition of the compound and about time dependent cell status under the interaction of the compound. The cells used in the above assays may have been transfected with molecules of interest using chemical, viral, or electroporation-assisted transfection methods. Molecules that are introduced into cells may include a DNA molecule, a recombinant DNA molecule, a native DNA molecule, a plasmid, a cDNA, anti-sense DNA strand or oligonucleotides, an RNA molecule, a siRNA molecule, a microRNA molecule, native RNA molecule, ribozyme RNA or an aptamer, an oligopeptide, a polypeptide, a protein, a compound or an organic compound. The molecules that are introduced to the cells may be capable of affecting transcription or affecting translation or affecting RNA splicing or affecting RNA editing, or affecting a cellular function selected from the group consisting of cell proliferation, cell adhesion, and cell spreading, or affecting cell morphology, or affecting a cellular receptor or signal transduction pathway activated by the said receptor. In a preferred embodiment of the methods of the present invention, the method comprise a) providing an above described device of the present invention that comprises wells or fluidic containers, at least one of which comprises an electrode array and a set of electroporation electrodes; b) seeding the cells to the wells of multiple-well devices; c) electroporating cells to result in introduction of molecules of interest to the cells; d) adding a test compound to the wells containing cells; e) monitoring cell-substrate impedance before and after adding the compound at a regular or irregular time interval; wherein the time dependent impedance change provides information about time dependent cell status before addition of the compound and about time dependent cell status under the interaction of the compound. Molecules that are introduced into cells may include a DNA molecule, a recombinant DNA molecule, a native DNA molecule, a plasmid, a cDNA, anti-sense DNA strand or oligonucleotides, an RNA molecule, a siRNA molecule, a microRNA molecule, native RNA molecule, ribozyme RNA or an aptamer, an oligopeptide, a polypeptide, a protein, a compound or an organic compound. The molecules introduced to the cells may affect one or more cellular functions, leading to a change in the way cells interact with the test compound. Thus, the effect of the test compound can be investigated by monitoring cell-substrate impedance after the test compound is added to the cells.

Information about cell status includes, not limited to, cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. In particular, information about change in cell status as a result of cells being transfected with the molecules of interest can be provided. Information about cell status may also include any compound-cell interaction leading to any change to one or more of above cell status indicators. For example, if the test compound binds to a receptor on the cell surface and such binding leads to a change in cell morphology, then the binding of compound to the receptor can be assayed by the monitored cell-substrate impedance. In this example, the cells may be transfected with a molecule that may have an effect the receptor in the cells (for example, transfecting a siRNA molecule to target and silence the gene corresponding to the receptor) or effect on signal transduction pathway activated by this receptor. Thus, the cells and the receptor-associated functions are altered because of the transfection, leading to a change in the interaction of the test compound with the cells. The cell-based assays that are performed with above methods include, but not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, cell-based assay for screening and measuring ligand-receptor binding.

In one embodiment of the above cell-based assay, the cell-substrate impedance is monitored at regular time intervals. In exemplary embodiments, the impedance is measured at a regular 2 hour, 1 hour, 30 min or 15 min time interval before and after adding the compound. In the present application, a real-time assay means that one can perform the measurement on cell-substrate impedance with various time resolutions, for example, measurement taking place at a longer time interval such as every hour or every two hours, or at a shorter time interval every minute or a few minutes. Real-time assay does not mean that the measurements are provided in a continuous, uninterrupted fashion. In another word, real-time assay does not mean that the measurements are performed at every single moment.

D.1. Cell Proliferation Assays

The present invention provides methods for performing cell proliferation assays. In these assays, an increase in monitored impedance is indicative of an increases cell number. The impedance measurements or impedance values derived from impedance measurements can be plotted versus time to obtain growth curves for cells growing in a fluid container of a cell-substrate monitoring device of the present invention. Cells in the proliferation assay may be transfected with molecules of interest. Thus, the effect of the molecules of interest that are introduced into the cells on cell proliferation may be investigated using cell-substrate impedance monitoring. Thus, combining cell transfection with impedance monitoring in cell proliferation assays may permit the study of the roles of specific intracellular molecules in cell proliferation. For example, if the role of a particular receptor tyrosine kinase needs to be assessed in cell proliferation, then either an siRNA, shRNA, mRNA, cDNA encoding for dominant negative version of the receptor, an inhibitory antibody, protein fragment, peptide or a small molecular inhibitor maybe introduced into the cell by any or combination of the methods mentioned above and the effect of such reagents can then be assessed on cell proliferation using the present invention. This assay will be performed using the following method: 1) cells expressing the specific growth factor receptors are introduced using any one of the methodologies described above with any one or combination of molecules or macromolecules which target the receptor physically or functionally, 2) impedance of the transfected cells is monitored prior to and after the introduction of the molecules or macromolecules and is compared with impedance of the control cells that have not been treated with any molecules or macromolecule or or introduced with control molecules or macromolecules that do not have direct effects on the receptor of interest. Preferably, the impedance of transfected cells and the control cells is monitored at multiple time points. For the transfected cells, the molecules and macromolecules transfected will functionally or physically interfere with the function of the receptor tyrosine kinase of interest. Thus, if such receptor tyrosine kinase plays an important role in cell growth and proliferation, then growth or proliferation of the transfected cells will be expected to be reduced significantly, as compared with control cells which were transfected with control molecules or macromolecules.

The present invention provides a method of generating at least one cell growth curve, comprising: providing a device of the present invention having two or more electrode arrays, each of which is associated with a fluid container of the device; attaching the device to an impedance analyzer; adding cells to one or more fluid containers of the device; monitoring impedance from the one or more fluid containers to obtain impedance measurements at three or more time points after adding the cells to one or fluid containers; and plotting the impedance measurements or values for the three or more time points versus time to generate at least one growth curve for the cells in the one or more fluid containers. The cells may be transfected with molecules of interest such as a protein, a polypeptide, a nucleic acid molecule, a RNAi, a siRNA, or an organic compound before they are added to the fluidic containers of the device in above method. The molecules that are transfected into the cells may interact with certain target intracellular molecules that play roles in cell proliferation and thus affect the cell proliferation. The effect of such transfected molecules on cell proliferation can be monitored using the method of the present invention. The transfection method may be a chemical (for example: lipid-mediated or amine-mediated) transfection, viral transfection, electroinjection-based transfection or electroporation-based transfection. The electroporation-based transfection may be performed in different devices from those used for cell-substrate impedance monitoring. Or, the electroporation-based transfection may be performed in the same devices as those used for cell-substrate impedance monitoring. Thus, the present invention provides a method for generating a cell growth curve for cells that are transfected with molecules of interest.

In a preferred embodiment of the method for generating at least one cell growth curve, comprising: providing an above described device of the present invention that comprises wells or fluidic containers, at least one of which comprises an electrode array and a set of electroporation electrodes; seeding cells to one or more fluid containers of the device; electroporating cells to result in introduction of molecules of interest to the cells; monitoring impedance from the one or more fluid containers to obtain impedance measurements at three or more time points after adding the cells to the one or fluid containers; and plotting the impedance measurements or values for the three or more time points versus time to generate at least one growth curve for the cells in the one or more fluid containers. Molecules that are introduced into cells may include a DNA molecule, a recombinant DNA molecule, a native DNA molecule, a plasmid, a cDNA, anti-sense DNA strand or oligonucleotides, an RNA molecule, a siRNA molecule, a microRNA molecule, native RNA molecule, ribozyme RNA or an aptamer, an oligopeptide, a polypeptide, a protein, a compound or an organic compound. The molecules introduced to the cells may affect cell proliferation and thus affect cell growth curve.

The present invention also provides a method of generating at least one growth curve using a system of the present invention, where the system includes a multi-well cell-substrate impedance monitoring device, an impedance analyzer, a device station, and a software program. The method includes; providing a multi-well cell-substrate impedance measuring system; adding cells to one or more wells of the system; monitoring impedance from the one or more wells to obtain impedance measurements at three or more time points after adding cells to the one or more wells; and plotting impedance measurements or impedance values for the three or more time points versus time to generate a growth curve for the cells in the one or more wells. The cells may be transfected with molecules of interest such as a protein, a polypeptide, a nucleic acid molecule, a RNAi, a siRNA, or an organic compound before they are added to the fluidic containers of the device in above method. The molecules that are transfected into the cells may interact with certain target intracellular molecules that play roles in cell proliferation and thus affect the cell proliferation. The effect of such transfected molecules on cell proliferation can be monitored using the method of the present invention. The transfection method may be a chemical transfection, viral transfection, electroinjection-based transfection or electroporation-based transfection. The electroporation-based transfection may be performed in different devices from those used for cell-substrate impedance monitoring. Or, the electroporation-based transfection may be performed in the same devices as those used for cell-substrate impedance monitoring.

Preferably, using a device or system of the present invention, impedance is monitored at four or more time points, in which at least one of the four or more time points is measured from a fluid container prior to adding cells to the fluid container. Preferably, impedance is monitored at regular or irregular time intervals for an assay period of from minutes to days. In many cases, proliferation assays can be performed by monitoring impedance for a period of between several hours and several days.

It is preferable to perform replicate proliferation assays in which more than one fluid container is seeded with same number of cells of the same type. In this case, a plot can optionally be generated by plotting averaged impedance measurements of values at assayed time points for replicate wells versus time. Preferably, a standard deviation for the averaged values is also calculated.

A growth curve can be generated by plotting impedance measurements versus time, or by plotting cell index values that are calculated from impedance measurements, such as normalized cell index values or delta cell index values versus time. The impedance measurement or cell index axis (typically the y-axis) can optionally use a log scale.

An impedance value can be any indices of impedance derived from impedance measurement, including, as nonlimiting examples, a cell index, a normalized cell index or a delta cell index. In certain embodiment, impedance value can also be a "raw" measured or monitored impedance value. Cell index (including normalized and delta cell index) can be a useful value for plotting growth curves, as it relates impedance measurements to cell number. For cell growth curves, a delta cell index for a given time point can be derived by subtracting the cell index at a baseline point, such as a time point after cell attachment and just before log phase growth, from the cell index measurement at the given time point. Preferably, determinations of impedance values and generating growth curves based on impedance measurements or values can be performed by software, and preferably by software that interfaces directly with the impedance analyzer. For example, where the growth assays are performed by a system of the present invention, impedance values (where used) can be measured or derived or calculated and growth curves generated by a software program that controls and receives data from the impedance analyzer.

A growth curve generated from impedance measurements or cell index values (including normalized cell index values and delta cell index values) can optionally be used to calculate one or more kinetic parameters of cell growth or behavior. For example, a growth curve can be used to calculate the length of a lag phase, cell attachment time, cell attachment rate, or a cell doubling time. As described above, the cells in these analyses and calculations may be transfected with molecules of interest. The transfected molecules may be a protein, a polypeptide, a nucleic acid molecule, a RNAi, a siRNA, or an organic compound.

Comparing Growth Curves of Two of More Cell Types

Two or more cell types can be seeded to separate wells in a proliferation assay using the methods of the present invention to generate growth curves of the two or more cell types. The growth curves or kinetic parameters derived from the growth curves of the cell types can be compared. The two or more cell types in the proliferation assay may be transfected with molecules of interest such as a protein, a polypeptide, a nucleic acid molecule, a RNAi, a siRNA, or an organic compound before or after they are added to the fluidic containers of the devices. The molecules that are transfected into the cells may interact with certain target intracellular molecules that play roles in cell proliferation and thus affect the cell proliferation. The effect of such transfected molecules on cell proliferation can be monitored using the method of the present invention. The transfection method may be a chemical transfection, viral transfection, electroinjection-based transfection or electroporation-based transfection. The electroporation-based transfection may be performed in different devices from those used for cell-substrate impedance monitoring. Or, the electroporation-based transfection may be performed in the same devices as those used for cell-substrate impedance monitoring.

In this aspect, the invention includes a method of generating growth curves for at least two cell types, comprising: providing a device of the present invention having two or more electrode arrays, each of which is associated with a fluid container of the device; attaching the device to an impedance analyzer; adding cells of two or more cell types to two or more fluid containers of the device, in which at least one of the two or more fluid containers receives one cell type and at least one other of the two or more fluid containers receives a different cell type, to provide two or more fluid containers comprising two or more different cell types; monitoring impedance from the two or more fluid containers comprising different cell types at three or more time points after adding the two or more cell types to the two or more fluid containers; and plotting impedance measurements or impedance values for the three or more time points versus time to generate a growth curve for the two or more cell types. Each of the cell types may be transfected using a transfection method with molecule such as a protein, a polypeptide, a nucleic acid molecule, a RNAi, a siRNA, an organic compound and the like. The molecules that are transfected into the cells may interact with certain target intracellular molecules that play roles in cell proliferation and thus affect the cell proliferation. The effect of such transfected molecules on cell proliferation can be monitored using the method of the present invention. The transfection method may be a chemical transfection, viral transfection, electroinjection-based transfection or electroporation-based transfection. The electroporation-based transfection may be performed in different devices from those used for cell-substrate impedance monitoring. Or, the electroporation-based transfection may be performed in the same devices as those used for cell-substrate impedance monitoring.

The present invention also provides a method of generating at least one growth curve using a system of the present invention, where the system includes a multi-well cell-substrate impedance monitoring device, an impedance analyzer, a device station, and a software program. The method includes; providing a multi-well cell-substrate impedance measuring system; adding cells of two or more cell types to two or more wells of the device, in which at least one of the two or more wells receives one cell type and at least one other of the two or more wells receives a different cell type, to provide two or more wells comprising two or more different cell types; monitoring impedance from the two or more wells comprising different cell types at three or more time points after adding the two or more cell types to the two or more wells; and plotting impedance measurements or impedance values for the three or more time points versus time to generate a growth curve for the two or more cell types. Each of the cell types may be transfected with molecules such as a protein, a polypeptide, a nucleic acid molecule, a RNAi, a siRNA, an organic compound and the like. The molecules that are transfected into the cells may interact with certain target intracellular molecules that play roles in cell proliferation and thus affect the cell proliferation. The effect of such transfected molecules on cell proliferation can be monitored using the method of the present invention. The transfection method may be a chemical transfection, viral transfection, electroinjection-based transfection or electroporation-based transfection. The electroporation-based transfection may be performed in different devices from those used for cell-substrate impedance monitoring. Or, the electroporation-based transfection may be performed in the same devices as those used for cell-substrate impedance monitoring.

As, described above for proliferation assays, impedance is preferably monitored using an impedance monitoring device or system at four or more time points, in which at least one of the four or more time points is measured from fluid containers prior to adding cells to the fluid containers. Preferably, impedance is monitored at regular or irregular time intervals for an assay period of from minutes to days, for example, for a period of between several hours and several days.

It is preferable to perform replicate proliferation assays in which more than one fluid container is seeded with same number of cells of the same type. In this case, a plot can optionally be generated by plotting averaged impedance measurements of values at assayed time points for replicate wells versus time. Preferably, a standard deviation for the averaged values is also calculated.

Growth curves for different cell types can be generated as described above. Impedance or impedance values, such as cell index, normalized cell index, or delta cell index can be plotted versus time. The impedance measurement or cell index axis (typically the y-axis) can optionally use a log scale.

A growth curve generated from impedance measurements or cell index values (including normalized cell index values and delta cell index values) can optionally be used to calculate one or more kinetic parameters of cell growth or behavior. For example, a growth curve can be used to calculate the duration of a lag phase, cell attachment time, cell attachment rate, or a cell doubling time.

Preferably, the growth curves of the two or more different cell types, or kinetic parameters derived from the growth curves of the two or more different cell types, are compared to determine differences among the cell types in proliferation patterns or rates, or in kinetic parameters that can be derived from growth curves. The different cell types used can be any cell types, including primary cells isolated from blood or tissue of an animal or human, or cells from cell lines. For example, proliferation rates of two types of primary cancer cell can be compared, or of primary cancer cells of the same type but different grades. In another example, primary cells of individuals of different genotypes can be compared. In another example, proliferation rates of primary or cell line stem cells can be compared. In yet another example, growth curves or parameters of control and genetically modified cells of a cell line can be compared. In yet another example, growth curves or parameters of cells infected with virus and control cells can be compared.

D.2. Quantifying Cells Using Cell-Substrate Impedance Devices

The present invention also includes a method of quantifying cells, comprising: providing a device of the present invention having two or more electrode arrays, each of which is associated with a fluid container of the device; attaching the device to an impedance analyzer; adding cells to one or more fluid containers of the device; monitoring impedance from the one or more fluid containers to obtain impedance measurements at one or more time points after adding the cells to the one or more fluid containers; deriving a cell index for the one or more time points; and using the cell index to determine the number of cells in the one or more fluid containers at least one of the one or more time points. The cell index is used to determine the number of cells using a formula that relates cell index to cell number, in which the formula is obtained by: providing a device for cell-substrate monitoring, attaching the device to an impedance monitor; adding cells to one or more fluid containers of the device; measuring impedance of the one or more fluid containers comprising cells; calculating a cell index from the impedance measurements; determining the number of cells of said at least one fluid container at the time of impedance monitoring by a means other than impedance monitoring; and deriving a formula that relates the number of cells of the one or more fluid containers at the two or more time points with the impedance measurements at the two or more time points.

Cells in above method for cell quantification may be transfected with molecules such as a protein, a polypeptide, a nucleic acid molecule, a RNAi, a siRNA, an organic compound and the like. Thus, the present invention provides a method for quantifying cells that have been transfected with the molecules of interest. The molecules that are transfected into the cells may interact with certain intracellular targets that play roles in cell proliferation or cell adhesion or cell morphology and thus affect the cell proliferation or cell adhesion or cell morphology. The effect of such transfected molecules on cell proliferation can be monitored using the method of the present invention. The transfection method may be a chemical transfection, viral transfection, electroinjection-based transfection or electroporation-based transfection. The electroporation-based transfection may be performed in different devices from those used for cell-substrate impedance monitoring. Or, the electroporation-based transfection may be performed in the same devices as those used for cell-substrate impedance monitoring.

In the embodiment of above method for obtaining the formula, sometimes, the number of cells introduced to the wells are pre-known or predetermined before cells are added in to the wells. Under such conditions, one assumes that there will be no change in cell number or little change in cell number when the impedance measurement for obtaining the formula is performed.

The number of cells determined by a method other than impedance monitoring can be determined by, for example, cell plating, hemacytometer counting, flow cytometry, Coulter counting, or by laser or optical detection techniques.

The method can also be practiced using an impedance monitoring system of the present invention, where the system includes a multi-well cell-substrate impedance monitoring device, an impedance analyzer, a device station, and a software program. The method includes; providing a multi-well cell-substrate impedance measuring system; adding cells one or more wells of the system; monitoring impedance from the one or more wells comprising cells at one or more time points after adding the cells to the one or more wells; deriving a cell index for the one or more time points; and using the cell index to determine the number of cells in said at least well at at least one of said one or more time points.

The cell index is used to determine the number of cells using a formula that relates cell index to cell number, in which the formula is obtained by: providing a system for cell-substrate monitoring, where the system comprises at least one multi-well cell-substrate impedance monitoring device, adding cells to one or more wells of a device of the system; measuring impedance of the one or more wells comprising cells at two or more time points; calculating a cell index from the impedance measurement at the two or more time points;

determining the number of cells of the one or more wells at the two or more time points by a means other than impedance monitoring; and deriving a formula that relates the number of cells of the one or more wells at the two or more time points with the impedance measurements at the two or more time points.

In the embodiment of above method for obtaining the formula, sometimes, the number of cells introduced to the wells are pre-known or predetermined before cells are added in to the wells. Under such conditions, one assumes that there will be no change in cell number or little change in cell number when the impedance measurement for obtaining the formula is performed.

The number of cells determined by a method other than impedance monitoring can be determined by, for example, cell plating, hemacytometer counting, flow cytometry, coulter counting or by an optical detection technique.

Formulas relating cell index (including normalized cell index and delta cell index, which can also be used) to cell number for a given cell type can be used to quantitate cells of that type in assays using a cell-substrate impedance monitoring device, such as a device described herein. Generally, for a give cell type and for cells under similar physiological conditions, the derived formulas relating cell index to cell number can be used in subsequent assays. There is no need to obtain the formula each time when an assay is performed. However, it is worthwhile to point that the formula can only be valid as long as the cells are under same physiological conditions in the assays where the formula was derived and where the formula is used. If the cell condition is different, for example, the composition of culture medium changed, or the cell attachment surface is altered, then the formula will not hold. In another example, if cells are in log-growth phase in one assay and are in stationary phase in another assay, then the formula may not hold. Another point worth mentioning here is that relates the fact the derived cell index or impedance also depends on cell attachment quality on the surface as well as cell morphology. If cell morphology or cell attachment changes during an assay, then one need to distinguish between the changes caused by change in cell number or in cell morphology or in cell attachment.

As an example, we can derive the correlation formula between cell index and cell number for NIH3T3 cells under the experimental conditions. The formula for converting cell index to cell number for this particular case is: Cell number=2000*Cell index−145.

D.3. Cell-Based Assays to Test the Effects of Compounds on Cells

In yet another aspect, the present invention provides a method for performing a cell-based assay investigating the effect of one or more test compounds on cells, comprising: providing a device of the present invention having two or more electrode arrays, each of which is associated with a fluid container of the device; attaching the device to an impedance analyzer; introducing cells into two or more fluid containers of the device that comprise an electrode array; adding at least one test compound to at least one of the one or more of the fluid containers comprising cells and an electrode array to provide at least one test compound well; providing at least one control well to which cells are added that does not receive test compound; and monitoring cell-substrate impedance of the one or more test compound fluid containers and the one or more control fluid containers at least three time points after adding the one or more test compounds, and analyzing impedance measurements from the one or more test compound fluid containers and the one or more control fluid containers at at least three time points after adding the one or more test compounds, in which changes in impedance can provide information about cell responses to the one or more test compounds. The cells used in the above method for investigating the effect of one or more test compounds on cells may have been transfected with molecules of interest using chemical, viral, or electroporation-assisted transfection methods. Molecules that are introduced into cells may include a DNA molecule, a recombinant DNA molecule, a native DNA molecule, a plasmid, a cDNA, anti-sense DNA strand or oligonucleotides, an RNA molecule, a siRNA molecule, a microRNA molecule, native RNA molecule, ribozyme RNA or an aptamer, an oligopeptide, a polypeptide, a protein, a compound or an organic compound. The molecules that are introduced to the cells may be capable of affecting transcription or affecting translation or affecting RNA splicing or affecting RNA editing, or affecting a cellular function selected from the group consisting of cell proliferation, cell adhesion, and cell spreading, or affecting cell morphology, or affecting a cellular receptor or signal transduction pathway activated by the said receptor. The molecules introduced to the cells may affect one or more cellular functions, leading to a change in the way cells interact with the test compound. Thus, the effect of the test compound can be investigated by monitoring cell-substrate impedance after the test compound is added to the cells.

In a preferred embodiment of the methods of the present invention, the method comprise a) providing an above described device of the present invention that comprises wells or fluidic containers, at least one of which comprises an electrode array for cell-substrate impedance monitoring and a set of electroporation electrodes; b) seeding the cells to the wells of multiple-well devices; c) electroporating cells to result in introduction of molecules of interest to the cells; d) adding a test compound to the wells containing cells; e) monitoring cell-substrate impedance before and after adding the compound at a regular or irregular time interval; wherein the time dependent impedance change provides information about time dependent cell status before addition of the compound and about time dependent cell status under the interaction of the compound. Molecules that are introduced into cells may include a DNA molecule, a recombinant DNA molecule, a native DNA molecule, a plasmid, a cDNA, anti-sense DNA strand or oligonucleotides, an RNA molecule, a siRNA molecule, a microRNA molecule, native RNA molecule, ribozyme RNA or an aptamer, an oligopeptide, a polypeptide, a protein, a compound or an organic compound. The molecules introduced to the cells may affect one or more cellular functions, leading to a change in the way cells interact with the test compound. Thus, the effect of the test compound can be investigated by monitoring cell-substrate impedance after the test compound is added to the cells.

In one example, a test compound is suspected to be a ligand or agonist for an orphan GPCR (G-Protein Coupled Receptor) in a particular cell type, monitoring cell substrate impedance for cells transfected with certain molecules may allow validation of the orphan GPCR as a target for the test compound (as an agonist or ligand). In one approach, if an orphan GPCR is being validated as a target for a particular agonist or ligand, then specific inhibitory molecules such as siRNA, mRNA, shRNA or a cDNA encoding a dominant negative version of the receptor of interest is introduced into a cell which is expressing the particular receptor. The inhibitory molecules are expected to interfere with either the expression or function of the GPCR and inhibit its activation by its cogante ligand. As a control, the cells are transfected with a control molecule. The activation of the receptor by addition of the particular agonist or ligand (the test compound) to the cells can be monitored using impedance at various time points after addition of the agonist or ligand for cells transfected with inhibitory molecules. If the GPCR of interest does serve as the receptor for the identified agonist or ligand then interfering with its function or expression is expected to prevent activation of the cell as monitored by impedance measurement. Cells transfected with the control molecules should respond to the agonist or ligand, i.e., after addition of the agonist or ligand to the cells, the receptors are activated and activation of such receptors can be monitored using cell-substrate impedance sensing. Using cell-substrate impedance sensing to monitor activation of GPCR has been disclosed in U.S. patent application Ser. No. 11/198,831, entitled, "Dynamic Monitoring of Activation of G-Protein Coupled Receptor (GPCR) and Receptor Tyrosine Kinase (RTK) in Living Cells using Real-Time Microelectronic Cell Sensing Technology, filed on Aug. 4, 2005, which is herein incorporated by reference in its entirety.

Alternatively, a complimentary approach to test whether a particular GPCR can serve a receptor for a particular agonist or ligand (the test compound) is to transfect the cDNA encoding for the GPCR in a cell line which does not express the receptor of interest. Two basic methods can be employed to express the receptor. In the first method a cell line stably expressing the receptor could be established. Alternatively, the receptor can be transfected transiently in the cell line. As a control, the cells can be stably or transiently transfected with a control cDNA. The functional activation of the transient or stably expressed receptor in response to the agonist or ligand can be assessed using impedance readout. If the ligand or agonist does bind and activate the receptor, then it is expected that it would activate the cells as monitored by impedance. The control cells should not respond to the ligand.

In a related aspect the present invention also provides a method for performing a cell-based assay investigating the effect of one or more test compounds on cells, where the system includes a multi-well cell-substrate impedance monitoring device, an impedance analyzer, a device station comprising electronic circuitry that engages the device and connects the two or more electrode arrays of the device to the impedance analyzer, and a software program that controls the device station and can record and analyze data from the impedance analyzer. The method includes: providing a multi-well cell-substrate impedance measuring system; adding at least one test compound to at least one of the one or more of the wells comprising cells to provide at least one test compound well; providing at least one control well to which cells are added that does not receive test compound; monitoring cell-substrate impedance of the one or more test compound wells and the one or more control wells at at least three time points after adding the one or more test compounds; and analyzing impedance measurements from the one or more test compound wells and the one or more control wells at at least three time points after adding the one or more test compounds, in which changes in impedance can provide information about cell responses to the one or more test compounds. The cells used in the above method for investigating the effect of one or more test compounds on cells may have been transfected with molecules of interest using chemical, viral, or electroporation-assisted transfection methods. Molecules that are introduced into cells may include a DNA molecule, a recombinant DNA molecule, a native DNA molecule, a plasmid, a cDNA, anti-sense DNA strand or oligonucleotides, an RNA molecule, a siRNA molecule, a microRNA molecule, native RNA molecule, ribozyme RNA or an aptamer, an oligopeptide, a polypeptide, a protein, a compound or an organic compound. The molecules that are introduced to the cells may be capable of affecting transcription or affecting translation or affecting RNA splicing or affecting RNA editing, or affecting a cellular function selected from the group consisting of cell proliferation, cell adhesion, and cell spreading, or affecting cell morphology, or affecting a cellular receptor or signal transduction pathway activated by the said receptor. The molecules introduced to the cells may affect one or more cellular functions, leading to a change in the way cells interact with the test compound. Thus, the effect of the test compound can be investigated by monitoring cell-substrate impedance after the test compound is added to the cells.

In a preferred embodiment of the method of the present invention for performing a cell-based assay investigating the effect of one or more test compounds on cells, the method comprises: providing an above described multi-well cell-substrate impedance measuring system, wherein for at least two wells, each of which comprises an electrode array for cell-substrate impedance monitoring and a set of electroporation electrodes; adding at least one test compound to at least one of the one or more of the wells comprising cells to provide at least one test compound well; providing at least one control well to which cells are added that does not receive test compound; electroporating cells in the test compound wells and control wells to result in introduction of molecules of interest in the cells; monitoring cell-substrate impedance of the one or more test compound wells and the one or more control wells at at least three time points after adding the one or more test compounds; and analyzing impedance measurements from the one or more test compound wells and the one or more control wells at at least three time points after adding the one or more test compounds, in which changes in impedance can provide information about cell responses to the one or more test compounds.

A test compound can be any compound, including a small molecule, a large molecule, a molecular complex, an organic molecule, an inorganic molecule, a biomolecule such as but not limited to a lipid, a steroid, a carbohydrate, a fatty acid, an amino acid, a peptide, a protein, a nucleic acid, a DNA molecule, a cDNA molecule, a RNA molecule, a RNAi molecule, a siRNA molecule, a oligonucletide, an aptamer, a ribozyme RNA or any combination of these. A test compound can be a synthetic compound, a naturally occurring compound, a derivative of a naturally-occurring compound, etc. The structure of a test compound can be known or unknown.

Information about cell responses to the one or more test compounds includes, but is not limited to, information about cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance.

The cells used in the assay can be primary cells isolated from any species or can be cells of cell lines. The cells can be genetically engineered cells (For example, cells from a genetically modified organism, such as for example from a "gene knockout" organism, or cells that have been engineered to over-express an endogenous gene or a transgene, or cells whose normal gene expression has been manipulated by use of antisense molecules or silencing RNA.) In some embodiments, different cell types are added to different wells and the behavior of the different cell types in response to one or more compounds is compared.

The cell-based assays that be performed with above methods include, but are not limited to, cell adhesion, cell spreading apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral, bacterial, or environmental toxin mediated cell pathologic changes or cell death, detection or quantification of neutralizing antibodies, specific T-cell mediated cytotoxic effect, and cell-based assay for screening or measuring ligand-receptor binding.

For cell adhesion assay, the method of the present invention may be used to investigate the role of a signaling protein in cell adhesion or cell spreading. For example, if the role of a signaling protein is being determined in cell adhesion and spreading assays, then molecules such as siRNA, shRNA, anti-sense DNA stand, or cDNA encoding a dominant negative version of the protein of interest can be transfected into the cell by certain transfection methods such as chemical or viral transfection or electroporation-assisted transfection. The cells will be transfected in regular tissue culture dishes, incubated with the inhibitory molecule for a given optimal time point and detached and then re-seeded on special plates which contain electronic sensors integrated in the bottom of the well for the detection of cell impedance. The attachment and spreading of the cells will be monitored by impedance measurements. As a control the impedance of cells transfected with a control molecule or non-transfected cell will be monitored concomitantly. If the function of the protein is necessary for cell attachment and spreading, it is expected interfering with its function by any of the indicated methods should significantly hamper the attachment and spreading of the cells as monitored using impedance readout. The attachment and spreading of the transfected cell will be compared with a control cell which should display normal attachment and spreading. The method for applying cell-substrate impedance sensing for cell adhesion and spreading has been disclosed in U.S. patent application Ser. No. 11/235,938, entitled, "Dynamic Monitoring of Cell Adhesion And Spreading Using the RT-CES System", filed on Sep. 27, 2005, which is incorporated by reference in its entirety.

For effector-cell mediated cytotoxicity assay, the method of the present invention may be used to investigate the function of a receptor on target cells in mediating the cytotoxicity effect of effector cells. For example, if the function of a receptor on target cells needs to be tested in mediating the cytotoxic effect of effector cells, such as natural killer cells (NK), cytotoxic T lymphocytes (CTLs), or PBMCs, then molecules such as siRNA, shRNA, anti-sense DNA, aptamers, and antibodies targeting the receptor of interest can be transfected into the target cells by a transfection method such as chemical or viral or electroporation-based transfection method. For example, the transfection can be directly carried out using electroporation methods on the plates that are integrated with the microelectrodes. After waiting for a specified period of time to allow the inhibitory molecule to take effect, then the effector cells can be added to the target cells growing in the bottom of the well in the plates. As a control, the target cells can also be transfected with a control molecule that has no effect on the protein of interest. If the receptor of interest is involved in mediating the cytotoxic activity of the effector cells upon target cells, then interfering with its function or expression should block to a significant degree the cytotoxic effect of effector cells upon target cells. The control cells would be expected to undergo cytotoxicity and as a result the cell-substrate impedance is expected to decrease over time. The cells transfected with the inhibitory molecules are expected to be resistant to the effector cells mediated cytotoxicity. The method for applying cell-substrate impedance sensing in monitoring effector-cell mediated cytotoxicity has been disclosed in U.S. patent application Ser. No. 11/197,994, entitled, "Method for Assaying for Natural Killer, Cytotoxic T-Lymphocyte and Neutrophil-Mediated Killing of Target Cells Using Real-Time Microelectronic Cell Sensing Technology", filed on Aug. 4, 2005, which is incorporated by reference in its entirety.

In the methods of the present invention that investigate test compound effects on cells, impedance is preferably monitored from at least one test compound well at at least one time point before adding said at least one test compound to said at least one test compound well. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurement taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

It is preferable to perform replicate test compound assays in which more than one fluid container of cells receives the same compound at the same concentration. In this case, impedance measurements or values can be averaged for the assayed time points for replicate wells. Preferably, a standard deviation for the averaged values is also calculated.

In the methods of the present invention, analyzing impedance can comprise plotting cell impedance versus time to obtain at least one test compound impedance curve and at least one control impedance curve. Preferably, at least one test compound impedance curve and said at least one control impedance curve are compared to identify a time frame, if any, in which a test compound curve differs significantly from a control curve, indicating a time frame of an effect of a test compound on cells. For example, depending on the time frame at which a test compound curve differs significantly from a control curve, the test compound can be hypothesized to affect one or more of, for example, cell attachment or adhesion, cell growth or proliferation, cytoskeleton organization or function, or apoptosis or cell death.

Preferably, data from impedance monitoring of a well that comprises cells and a test compound is compared with data from impedance monitoring of a well that comprises cells in the absence of a test compound, however, this is not a requirement of the present invention. For example, it is also possible to compare impedance measurements from one or more time points prior to the addition of compound to compare impedance measurements from one or more time points after the addition of compound. Such comparisons can be used directly to assess the cells' response to a compound. It is also possible to calculate a cell index (or cell number index) using the impedance values obtained.

Methods of calculating a cell index (cell number index) are disclosed herein as well as in parent application U.S. patent application Ser. No. 10/705,447, U.S. patent application Ser. No. 10/987,732, both herein incorporated by reference for disclosures relating to cell number index and its calculation. The cell index calculated from impedance measurements of wells receiving compound can be compared with the cell index calculated from impedance measurements of control wells to assess the effect of a compound on cells. Alternatively, cell index calculated from impedance measurements of wells from one or more time points after the addition of a compound can be compared with the cell index calculated from impedance measurements of wells from one or more time points prior to the addition of a compound to assess the effect of a compound on cells. In some preferred embodiments, the cell index can be used as an indicator of cytotoxicity.

The derivation of cell index from impedance measurements is provided in Section C of the present application. Cell index values (including normalized cell index values and delta cell index values) from at least three time points from at least one test compound well and at least one control well can be plotted versus time to obtain one or more test compound cell index curve and one or more control cell index curves. The one or more test compound cell index curves and the one or more control cell index curves can be compared to identify a time frame, if any, in which a test compound curve differs significantly from a control curve, indicating a time frame of an effect of a test compound on cells. For example, depending on the time frame at which a test compound curve differs significantly from a control curve, the test compound can be hypothesized to affect one or more of, for example, cell attachment or adhesion, cell growth or proliferation, cytoskeleton organization or function, or apoptosis or cell death.

Cell index values at three or more assay time points for one or more test compound wells and one or more control wells can be used to derive cell change index (CCI) values or a second order derivatives of cell index at three or more assay time points. The calculation of cell change index is provided in Section C of the present application. The value of CCI at a give time point can be determined to be either approximately equal to 0.7, much greater than 0.7, greater than zero and less than 0.7, approximately equal to zero, less than zero, or much less than zero. These values can indicate cell behavior at an assay time point, as CCI approximately equal to 0.7 indicates log rate growth, a CCI much greater than 0.7 indicates faster than log rate growth, a CCI greater than zero and less than 0.7 indicates slower than log rate growth, a CCI approximately equal to zero indicates no growth (a constant cell index), a CCI less than zero indicates cells are detaching from the substrate, and a CCI much less than zero indicates cell are detaching rapidly from the substrate.

For a given assay time point, differences in CCI value between control and compound treated wells can indicate a time at which the compound has an effect on cells, as well as providing information on the type of effect the compound has.

The CCI can further be used to obtain information on the effect of a test compound by plotting CCI versus time for at least three assay time points to obtain a cell change index curve (CCI curve) for at least one control container or well and at at least one test compound container or well. One or more test compound CCI curves can be compared with one or more control CCI curves to obtain information on cell status or behavior in response to said at least one test compound, wherein said cellular status or behavior is at least one of: cell attachment or adhesion status; cell growth or proliferation status; the number of viable cells or dead cells; cytoskeleton change or re-organization; or the number of cells going through apoptosis or necrosis.

Cell-Based Assays with More than One Cell Type

The present invention also provides methods of comparing the effects of a compound on two or more cell types. In one aspect, the method comprises: providing a device of the present invention having two or more electrode arrays, each of which is associated with a fluid container of the device; attaching the device to an impedance analyzer; introducing cells into two or more fluid containers of the device that comprise an electrode array, wherein at least one of the two or more fluid containers receives one cell type and at least one other of the two or more fluid containers receives a different cell type; adding a test compound to the one or more fluid containers receiving one cell type and adding the test compound to the one or more fluid containers receiving a different cell type to provide at least two test compound fluid containers that comprise cells of different types; providing at least two control fluid containers that do not receive test compound, in which at least one of the control fluid containers receives cells of the one type and at least one of the control fluid containers receives cells of the different type; monitoring cell-substrate impedance of the two or more test compound fluid containers that comprise different cell types and the one or more control fluid containers at at least three time points after adding the one or more test compounds; and analyzing impedance measurements from the two or more test compound fluid containers comprising different cell types and from the one or more control fluid containers at at least three time points after adding the one or more test compounds, in which changes in impedance can provide information about cell responses to the one or more test compounds. Each of the cell types may be transfected using a transfection method with molecule such as a protein, a polypeptide, a nucleic acid molecule, a RNAi, a siRNA, an organic compound and the like. The molecules that are transfected into the cells may interact or interfere with certain target molecules in the cells which play roles in one or more cell functions and thus affect one or more cell functions, leading to a change in the way cells interact with a test compound. The effect of such transfected molecules on cell functions or on cell responses to a test compound may be monitored using the method of the present invention. The transfection method may be a chemical transfection, viral transfection, electroporation-based transfection or other means of transfection. The electroporation-based transfection may be performed in different devices from those used for cell-substrate impedance monitoring. Or, the electroporation-based transfection may be performed in the same devices as those used for cell-substrate impedance monitoring.

In a related aspect the present invention also provides a method for performing a cell-based assay investigating the effect of one or more test compounds on cells using a cell-substrate impedance monitoring system of the present invention, where the system includes a multi-well cell-substrate impedance monitoring device, an impedance analyzer, a device station comprising electronic circuitry that engages the device and connects the two or more electrode arrays of the device to the impedance analyzer, and a software program that controls the device station and can record and analyze data from the impedance analyzer. The method includes: providing a multi-well cell-substrate impedance measuring system; introducing cells into two or more wells of the device that comprise an electrode array, wherein at least one of the two or more wells receives one cell type and at least one other of the two or more wells receives a different cell type; adding a test compound to the one or more wells receiving one cell type and adding the test compound to the one or more wells receiving a different cell type to provide at least two test compound wells that comprise cells of different types; providing at least two control wells that do not receive test compound, in which at least one of the wells receives cells of the one type and at least one of the control wells receives cells of the different type; monitoring cell-substrate impedance of the two or more test compound wells that comprise different cell types and the one or more control wells at at least three time points after adding the one or more test compounds; and analyzing impedance measurements from the two or more test compound wells comprising different cell types and from the one or more control wells at at least three time points after adding the one or more test compounds, in which changes in impedance can provide information about cell responses to the one or more test compounds. Each of the cell types may be transfected using a transfection method with molecule such as a protein, a polypeptide, a nucleic acid molecule, a RNAi, a siRNA, an organic compound and the like. The molecules that are transfected into the cells may interact or interfere with certain target molecules in the cells which play roles in one or more cell functions and thus affect one or more cell functions, leading to a change in the way cells interact with test compounds. The effect of such transfected molecules on cell functions or on cell responses to test compounds may be monitored using the method of the present invention. The transfection method may be a chemical transfection, viral transfection, or electroporation-based transfection or other means of transfection. The electroporation-based transfection may be performed in different devices from those used for cell-substrate impedance monitoring. Or, the electroporation-based transfection may be performed in the same devices as those used for cell-substrate impedance monitoring.

In the methods of the present invention that investigate test compound effects on cells, impedance is preferably monitored from at least two test compound wells comprising different cell types at at least one time point before adding test compound to the at least one two compound wells. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurement taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

As disclosed in an earlier section on compound assays, a test compound can be any compound whose effect on cells can be investigated. A test compound used in assays comparing cell responses can be a compound whose effect on one or more of the cell types to be assayed is known, or can be a compound whose effects on any of the cell types to be assayed are unknown. In preferred methods of the present invention, cells are introduced into at least three wells of the device that each comprise an electrode array, and at least one well that comprises an electrode array and comprises cells does not receive a test compound. A control well that does not receive a test compound can be monitored, and its impedance data can be compared with that of wells that receive a compound to determine the effect of the test compounds on cells.

As disclosed in a previous section for compound assays, the cell types used in the assay can be primary cells isolated from any species or can be cells of cell lines. In some preferred embodiments, the different cell types are the same type of cell from different individuals, and thus have different genotypes. One or more of the cell types can be genetically engineered (For example, cells from a genetically modified organism, such as for example from a "gene knockout" organism, or cells that have been engineered to overexpress an endogenous gene or a transgene, or cells whose normal gene expression has been manipulated by use of antisense molecules or silencing RNA.) In these cases, genetically modified cells can be compared with control cells. In another example the cells can be, for example, stem cells from different stages of differentiation or of different genotypes whose response to growth factors is being compared. In other examples the cells can be cancer cells where the test compound is tested for its cytotoxic effects. The cells can be primary cancer cells of the same type isolated from different individuals, for example, or different cancer cell lines, or cancer cells of the same type but of different grades. In some embodiments, three or more different cell types are added to different wells and the behavior of the three or more different cell types in response to one or more compounds is compared. In preferred embodiments of the present invention, for each cell type tested there is a control performed in which the control does not receive test compound.

A variety of assays can be employed, where the effect of a test compound on the behavior of two or more cell types in the assay is under investigation. Such assays include, as nonlimiting examples, cell adhesion assays, apoptosis assays, cell differentiation assays, cell proliferation assays, cell survival assays, cytotoxicity assays, cell morphology detection assays, cell quantification assays, cell quality control assays, time-dependent cytotoxicity profiling assays, IgE-mediated cell activation or stimulation assays, receptor-ligand binding assays, viral, bacterial, or environmental toxin mediated cell pathologic changes or cell death assays, detection or quantification of neutralizing antibodies, specific T-cell mediated cytotoxic effect assays, and cell-based assays for screening or measuring ligand-receptor binding.

In the assays of the present invention is preferable to perform replicate test compound assays in which more than one fluid container of cells of the same type receives the same compound at the same concentration. In this case, impedance measurements or values can optionally be averaged for the assayed time points for replicate wells. Preferably, a standard deviation for the averaged values is also calculated.

Preferably, time-dependent responses of the first and second types of cells are compared to see how similar or different the responses from the two types of cells are. In one method of the present invention, impedance from a first cell type well is plotted versus time to give a first cell type impedance curve and impedance from a second cell type well is plotted versus time to give a second cell type impedance curve. Cell index (including normalized cell index or delta cell index) from wells comprising cells of different types can also be calculated from impedance data and plotted versus time to give cell index curves.

The impedance curves or cell index curves from the different cell types can be compared to determine whether the time frame, magnitude, and duration of a cells response to a compound are similar or different. Preferably, impedance curves or cell index curves generated from control wells comprising each cell type in the absence of compound are compared with the test compound curves to assess the compound-specific effects on each cell type. The effects of the compounds on one or more of the two or more cell types can be effects on cell attachment or adhesion, cell growth or proliferation; the number of viable cells or dead cells; cytoskeleton organization or function; or the number of cells going through apoptosis or necrosis in response to a test compound. Assays can be designed to investigate the compound's effects on particular cellular processes or activities.

The effect of a compound on at least one of the cell types used in the assay may be known. The mechanism of action of a compound on at least one of the cell types used in the assay may be known. In such cases, comparison of the compound response of one or more different cell types with the compound response of a cell type whose response to the compound is characterized can give information as to the similarity or difference in response of a different cell type to the compound.

The CI derived from impedance data from wells comprising different cell types and a test compound can be used to derive cell change index (CCI) values for assay time points. CCI values of particular cell types at assay time points can be compared. Such comparisons can indicate whether different cell types are responding similarly to a compound. CCI can also be plotted versus time, and CCI curves of cells of different types assayed with one or more test compounds can be compared to determine the similarities or differences in cellular responses of different cell types to a test compound.

Cell-Based Assays with More than One Compound

The present invention also provides methods of comparing the effects of two or more different compounds on cells. In one aspect, the method comprises:
providing a device of the present invention having three or more electrode arrays, each of which is associated with a fluid container of the device; attaching the device to an impedance analyzer; introducing cells into three or more fluid containers of the device that comprise an electrode array; adding at least one test compound to at least one of the three or more fluid containers comprising cells and adding at least one different test compound to at least one other of the three or more fluid containers comprising cells to provide at least two different test compound fluid containers; providing as a control fluid container at least one of the three or more fluid containers, in which the control fluid container receives cells but does not receive compound; attaching an impedance analyzer to the device; monitoring cell-substrate impedance of the two or more different test compound fluid containers that comprise different compounds and the one or more control fluid containers at at least three time points after adding the one or more test compounds; and analyzing impedance measurements from the two or more different test compound fluid containers and from the one or more control fluid containers at at least three time points after adding the one or more test compounds, in which changes in impedance can provide information about cell responses to the one or more test compounds. Cells may be transfected using a transfection method with molecule such as a protein, a polypeptide, a nucleic acid molecule, a RNAi, a siRNA, an organic compound and the like. The molecules that are transfected into the cells may interact or interfere with certain target molecules in the cells which play roles in one or more cell functions and thus affect one or more cell functions, leading to a change in the way cells interact with one or more test compounds. The effect of such transfected molecules on cell functions or on cell responses to one or more test compounds may be monitored using the method of the present invention. The transfection method may be a chemical transfection, viral transfection, or electroporation-based transfection or other means of transfection. The electroporation-based transfection may be performed in different devices from those used for cell-substrate impedance monitoring. Or, the electroporation-based transfection may be performed in the same devices as those used for cell-substrate impedance monitoring.

In a related aspect, the present invention provides a method for performing a cell-based assay investigating the effect of two or more test compounds on cells using a cell-substrate impedance monitoring system. The method includes: a) providing a cell-substrate impedance monitoring system of the present invention; b) introducing cells into at least two wells of the device that each comprise an electrode array; c) adding to at least one well of the device comprising cells and an electrode array a first test compound; d) adding to at least one other well of the device comprising cells and an electrode array a second test compound; and e) monitoring cell-substrate impedance of at least one well comprising cells and a first compound and at least one well comprising cells and a second compound, in which changes in impedance can provide information about cell responses to the first and second compounds. Cells may be transfected using a transfection method with molecule such as a protein, a polypeptide, a nucleic acid molecule, a RNAi, a siRNA, an organic compound and the like. The molecules that are transfected into the cells may interact or interfere with certain target molecules in the cells which play roles in one or more cell functions and thus affect one or more cell functions, leading to a change in the way cells interact with one or more test compounds. The effect of such transfected molecules on cell functions or on cell responses to one or more test compounds may be monitored using the method of the present invention. The transfection method may be a chemical transfection, viral transfection, or electroporation-based transfection or other means of transfection. The electroporation-based transfection may be performed in different devices from those used for cell-substrate impedance monitoring. Or, the electroporation-based transfection may be performed in the same devices as those used for cell-substrate impedance monitoring.

Preferably, time-dependent responses of cells to the first compound and the second compound are compared to see how similar or different the responses from the two compounds are. In one preferred embodiment of this method, time-dependent cytotoxic responses are compared.

The cells and test compound that can be used in the assay can be any as described above for assays testing effects of test compounds.

In the assays of the present invention is preferable to perform replicate test compound assays in which more than one fluid container of cells of the same type receives the same compound at the same concentration. In this case, impedance measurements or values can optionally be averaged for the assayed time points for replicate wells. Preferably, a standard deviation for the averaged values is also calculated.

Impedance monitoring can be as described above for assays testing effects of test compounds. Preferably impedance is monitored from the at least two different test compound wells and at least one control well at at least one time point before adding said at least one test compound to said at least one test compound well. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurement taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

Preferably, data from impedance monitoring of wells that comprise different test compounds are compared.

In one embodiment, for at least two different compound wells, impedance at three or more assay time points can be plotted versus time. Preferably, for a control well that does not receive compound, impedance at the same three or more assay time points is also plotted versus time. The impedance curves of different compound wells can be compared with the control impedance curve to determine whether the compounds have a similar or different effect on cells.

Cell index (including normalized cell index or delta cell index) from wells comprising cells of different types can also be calculated from impedance data and plotted versus time to give cell index curves.

The impedance curves or cell index curves from the different cell types can be compared to determine whether the time frame, magnitude, and duration the response of cells to different compounds are similar or different. Preferably, impedance curves or cell index curves generated from one or more control wells comprising cells in the absence of compound are compared with the test compound curves to assess the compound-specific effects of each compound. The effects of the compounds on cells can be for example, effects on cell attachment or adhesion, cell growth or proliferation; the number of viable cells or dead cells; cytoskeleton organization or function; or the number of cells going through apoptosis or necrosis in response to a test compound. Assays can be designed to investigate the compound's effects on particular cellular processes or activities.

The effect on cells of one or more of the compounds used in the assay may be known. The mechanism of action of one or more compounds used in the assay may be known. In such cases, comparison of the responses of cells to other test compounds used in the assay with cellular responses to the one or more compounds whose effects are characterized can give information as to the similarity or difference in response of different compounds to a known compound.

Information about cell responses to the compound includes, but is not limited to, information about cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance. The cell-based assays that be performed with above methods include, but not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, cell-based assay for screening and measuring ligand-receptor binding.

A plurality of compounds can be assayed with multiple cell types. In one preferred embodiment of this method, time-dependent cytotoxic responses of different cell types to a set of compounds are compared.

The CI derived from impedance data from wells comprising different cell types and a test compound can be used to derive cell change index (CCI) values for assay time points. CCI values of particular cell types at assay time points can be compared. Such comparisons can indicate whether different cell types are responding similarly to a compound. CCI can also be plotted versus time, and CCI curves of cells of different types assayed with one or more test compounds can be compared to determine the similarities or differences in cellular responses of different cell types to a test compound.

For example, the time frame, magnitude, and duration of a difference in response as evidenced by the curves can indicate a difference in efficacy or mechanism of compounds. The impedance differences can reflect differences in, for example, cell attachment or adhesion, cell growth or proliferation; the number of viable cells or dead cells; cytoskeleton organization or function; or the number of cells going through apoptosis or necrosis in response to a test compound.

A variety of assays can be employed, where the effect of two or more test compound on the behavior cells is under investigation. Such assays include, as nonlimiting examples, cell adhesion assays, apoptosis assays, cell differentiation assays, cell proliferation assays, cell survival assays, cytotoxicity assays, cell morphology detection assays, cell quantification assays, cell quality control assays, time-dependent cytotoxicity profiling assays, IgE-mediated cell activation or stimulation assays, receptor-ligand binding assays, viral, bacterial, or environmental toxin mediated cell pathologic changes or cell death assays, detection or quantification of neutralizing antibodies, specific T-cell mediated cytotoxic effect assays, and cell-based assays for screening or measuring ligand-receptor binding.

In one preferred embodiment of this method, time-dependent cytotoxic responses of cells to a set of compounds are compared. "Cytotoxicity profiling" in which the impedance responses of cells in response to a plurality of potentially cytotoxic compounds are compared, can provide information on the efficacy and mechanism of a test compound. Cytotoxicity profiling can be performed by comparing any combination of impedance plots, kinetic parameters derived from impedance plots, CI plots, CCI values, and CCI plots.

In one embodiment of the method, analyzing the cytotoxicity response may include derivation of the slope of change in the time dependent cytotoxicity response at a given compound concentration. In yet another embodiment of the method, analyzing real-time cytotoxicity response may include derivation of high-order derivatives of the time dependent cytotoxicity response with respect to time at a given compound concentration.

Evaluating the Effect of Different Concentrations of a Compound on Cells

The present invention also includes methods of performing assays to test the effect of different concentrations of one or more test compounds on cells.

In one aspect, a method for testing different concentrations of a test compound on cells comprises: providing a device of the present invention having three or more electrode arrays, each of which is associated with a fluid container of the device; attaching the device to an impedance analyzer; introducing cells into at least two of the three or more fluid containers of the device that comprise an electrode array; adding different concentrations of a test compound to the two or more fluid containers of the device that comprise cells; providing a control fluid container that comprises cells but does not receive compound; monitoring cell-substrate impedance of the two or more different test compound fluid containers that comprise different concentrations of a test compound and of the one or more control fluid containers at at least three time points after adding a test compound; and analyzing impedance measurements from the two or more different test compound fluid containers and one or more control fluid containers at at least three time points after adding a test compound, in which changes in impedance can provide information about cell responses to the test compounds. Cells may be transfected using a transfection method with molecule such as a protein, a polypeptide, a nucleic acid molecule, a RNAi, a siRNA, an organic compound and the like. The molecules that are transfected into the cells may interact or interfere with certain target molecules in the cells which play roles in one or more cell functions and thus affect one or more cell functions, leading to a change in the way cells interact with one or more test compounds. The effect of such transfected molecules on cell functions or on cell responses to one or more test compounds may be monitored using the method of the present invention. The transfection method may be a chemical transfection, viral transfection, or electroporation-based transfection or other means of transfection. The electroporation-based transfection may be performed in different devices from those used for cell-substrate impedance monitoring. Or, the electroporation-based transfection may be performed in the same devices as those used for cell-substrate impedance monitoring.

In a related aspect, the present invention provides a method for performing a cell-based assay investigating the effect of two or more concentrations of a test compound on cells using a cell-substrate impedance monitoring system. The method includes: providing a cell-substrate impedance monitoring system of the present invention; introducing cells into at least two of the three or more wells of the device that comprise an electrode array; adding different concentrations of a test compound to the two or more wells of the device that comprise cells; providing a control well that comprises cells but does not receive test compound; monitoring cell-substrate impedance of the two or more different test compound wells that comprise different concentrations of a test compound and the one or more control wells at at least three time points after adding a test compound; and analyzing impedance measurements from the two or more different test compound wells and the one or more control wells at at least three time points after adding a test compound, in which changes in impedance can provide information about cell responses to the test compounds. Cells may be transfected using a transfection method with molecule such as a protein, a polypeptide, a nucleic acid molecule, a RNAi, a siRNA, an organic compound and the like. The molecules that are transfected into the cells may interact or interfere with certain target molecules in the cells which play roles in one or more cell functions and thus affect one or more cell functions, leading to a change in the way cells interact with one or more test compounds. The effect of such transfected molecules on cell functions or on cell responses to one or more test compounds may be monitored using the method of the present invention. The transfection method may be a chemical transfection, viral transfection, or electroporation-based transfection or other means of transfection. The electroporation-based transfection may be performed in different devices from those used for cell-substrate impedance monitoring. Or, the electroporation-based transfection may be performed in the same devices as those used for cell-substrate impedance monitoring.

The cells and test compound that can be used in the assay can be any as described above for assays testing effects of test compounds.

Impedance monitoring can be as described above for assays testing effects of test compounds. Preferably impedance is monitored from the at least two different test compound wells and at least one control well at at least one time point before adding said at least one test compound to said at least one test compound well. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurements taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

In one embodiment, for at least two different compound concentrations, impedance or, preferably, cell index (including normalized cell index or delta cell index), at three or more assay time points is be plotted versus time. Preferably, for a control well that does not receive compound, impedance at the same three or more assay time points is also plotted versus time. An impedance curve or cell index curve can give an indication of the time frame at which a compound affects cell response. In some preferred embodiments, the cell index can be used as an indicator of cytotoxicity.

Cytotoxicity Profiling

In another aspect, the present invention provides a method for performing real-time cytotoxicity assay of a compound, comprising: a) providing an above described system; b) seeding cells to the wells of multiple-well devices; c) adding the compound to the wells containing cells; d) monitoring cell-substrate impedance before and after adding the compound at a regular or irregular time interval; wherein the time dependent impedance change provides information about time dependent cytotoxicity of the compound. In one embodiment, the cell-substrate impedance is monitored at regular time intervals. In exemplary embodiments, the impedance is measured at a regular 2 hour, 1 hour, 30 min or 15 min time interval before and after adding the compound. Cells in the cytotoxicity assays may be transfected using a transfection method with molecule such as a protein, a polypeptide, a nucleic acid molecule, a RNAi, a siRNA, an organic compound and the like. The molecules that are transfected into the cells may interact or interfere with specific target molecules in the cells which may play a role in a compound-induced cytotoxicity. The effect of such transfected molecules on cell responses to one or more test compounds may be monitored using the method of the present invention. The transfection method may be a chemical transfection, viral transfection, or electroporation-based transfection or other means of transfection. The electroporation-based transfection may be performed in different devices from those used for cell-substrate impedance monitoring. Or, the electroporation-based transfection may be performed in the same devices as those used for cell-substrate impedance monitoring.

For example, the method of the present invention may be used for target-validation assessment of a target molecule (e.g., a protein) in the cells that may be involved in cytotoxicity. The experiment would be performed by transfecting molecules into the cells using a transfection method. The transfected molecules inhibit or interfere with the expression or function of the target of interest. Once, it is determined that the target molecule is sufficiently compromised in terms of its expression or function, then a cytotoxic agent, such antimiotics or DNA damaging agents can be added to the cells and the degree of cytotoxicity taking place can be evaluated by impedance measurements. As a control, the target cells can be transfected with a control molecule which does not affect the target molecule. If the target molecule is involved in mediating cytotoxicity, then its ablation or interfering with its function should curtail the effect of the cytotoxic agent. As an additional control, cells transfected with the inhibitory molecules will be left untreated to ascertain that the mere down-regulation or inhibition of target function does not affect cell viability. Application of cell-substrate impedance sensing for cytotoxicity assays has been disclosed in U.S. patent application Ser. No. 11/055,639, entitled "Real time electronic cell sensing system and applications for cytotoxicity profiling and compound assays" filed on Feb. 9, 2005, which is incorporated by reference in its entirety.

In one embodiment of the above method, multiple wells with same cell types are used, wherein each well is added with the compound of different concentrations. The method provides the time-dependent and concentration-dependent cytotoxic responses.

In yet another aspect, the present invention provides a method for analyzing and comparing time-dependent cytotoxic effects of a first compound and a second compound on a cell type, comprising: a) performing a real-time cytotoxicity assay on a cell type with the first compound using the method described above; b) performing a real-time cytotoxicity assay on said cell type with the second compound using the method described above; c) comparing the time-dependent cytotoxic responses of the first compound and the second compound to see how similar or different the responses from the two compounds are. In one embodiment of this method, time-dependent cytotoxic responses are determined for the first compound at multiple dose concentrations. In another embodiment, time-dependent cytotoxic responses are determined for the second compound at multiple dose concentrations. In yet another embodiment, time-dependent cytotoxic responses are determined for both first compound and second compound at multiple dose concentrations.

In another embodiment of above methods, the first compound is a compound with a known mechanism for its cytotoxic effect and the second compound is a compound with an unknown mechanism for its cytotoxic effect. If the time dependent cytotoxic responses from the second compound are similar to that of the first one, the second compound may follow a similar mechanism for its cytotoxic effect to the first compound.

Various approaches may be used in comparing the cytotoxic responses of the compounds. A cell index (or cell number index) can optionally be calculated using the impedance values obtained. In one embodiment of the method described above, time dependent IC50 may be derived for the compounds and comparison between their cytotoxic responses is done by comparing their time dependent IC50 curves based on cell index values. If the IC50 curves follow a similar time-dependent trend, the two compounds may follow a similar mechanism for inducing cytotoxicity effects. In another embodiment of the method described, direct comparison of time-dependent cytotoxic responses of two compounds are done where the concentrations for the two compounds may be the same or may be different. Direct comparison between time-dependent cytotoxic responses may be done by analyzing the slope of change in the measured responses (that is equivalent to the first order derivative of the response with respect to time) and comparing the time-dependent slopes for the two compounds. In another approach, the time-dependent cytotoxic responses may be analyzed for their higher order derivatives with respect to time. Comparing such high order derivatives may provide additional information as for the mechanisms of compound-induced cytotoxicity.

In one embodiment of the method, analyzing real-time cytotoxicity response may include the derivation of time-dependent IC50 values for the compound on the multiple cell types. In another embodiment of the method, analyzing real-time cytotoxicity response may include derivation of the slope of change in the time dependent cytotoxicity response at a given compound concentration. In yet another embodiment of the method, analyzing real-time cytotoxicity response may include derivation of high-order derivatives of the time dependent cytotoxicity response with respect to time at a given compound concentration.

In yet another embodiment, the above methods are applied to perform cytotoxicity profiling of multiple compounds on multiple cell types.

In another embodiment of the method, analyzing real-time cytotoxicity response may include derivation of the slope of change in the time dependent cytotoxicity response at a given compound concentration. In yet another embodiment of the method, analyzing real-time cytotoxicity response may include derivation of high-order derivatives of the time dependent cytotoxicity response with respect to time at a given compound concentration.

Some examples of compound assays that can be performed using a cell-substrate impedance system of the present invention are provided by way of illustration with reference to the figures. In these examples, cell index is calculated using the same method as the Cell Index calculation method (A) as described in Section C of the present application. In some of the figures of the present application, Normalized Cell Index was plotted. The Normalized Cell Index at a given time point is calculated by dividing the Cell Index at the time point by the Cell Index at a reference time point. Thus, the Normalized Cell Index is 1 at the reference time point.

As described in the present application, if the cell attachment conditions remain unchanged or exhibit little change over the course of an assay that uses impedance monitoring, then the larger the cell index, the larger the number of the cells in the wells. A decrease in cell index suggests that some cells are detaching from the substrate surface or dying under the influence of the compound. An increase in cell index suggests that more cells are attaching to the substrate surfaces, indicating an increase in overall cell number.

D.4. Modulation of Cellular Transmembrane Potentials and the Effect on Ion Channels Multiple-well microtiter plates with built-in, microfabricated electrodes in the wells—developed for real time cell electronic sensing system can be used for electrical stimulation of living cells. Electric fields can be generated in the wells by applying electrical voltage pulses of suitable waveform and magnitude to the electrode arrays within each, individual wells. The electric fields in the wells will cause a change in the transmembrane potentials of the cells so that the transmembrane potential of cells is manipulated or controlled. As a result, cells are stimulated and voltage-gated ion channels will open or close, depending on of the characteristics of the ion channels. The activity of these ion channels being opened or closed or other cell properties (for example, cell membrane potential, intracellular calcium concentration) that are changed as a result of these ion channels being opened or closed can be monitored by other methods, including but not limiting, various fluorescent detection methods, radioactive element flux assays. Various methods for ion channel activities have been described in "Automated electrophysiology: high throughput of art", by X Wang and M Li, in ASSAY and Drug Development Technologies, in Vol, 1, No. 5, pp 695-708, 2003; "HTS approaches to voltage-gated ion channel drug discovery", by Denyer J, Worley J, Cox B, Allen G, Banks M, in Drug Discoery Today, Vol. 3, p 323, 1998; "Assay technologies for screening ion channel targets", by Mattheakis L C and Savchenko A, in Current Opinion Drug Discovery and Development, Vol. 4, pp 124-134, 2001; "Ion channel assay technologies: quo vadis?" by Xu J, Wang X, Ensign B, Li M, Wu L, Guia A, Xu J-Q, in Drug Discovery Today, Vol. 6, pp 1278-1287, 2001. Many of these ion channel assay methods, in particular, those non-electrophysiology based methods, can be used to investigate ion channel activities as a result of cells being electrically stimulated using the instruments and methods described in this invention.

Electrodes in each well are organized so that there are two electrical connections leading out from the well. For real time cell electronic sensing, one approach is as follows: a small electric voltage (~10 mV or smaller as a peak value) of sinusoidal waveform (other waveform is possible, but sine wave is preferred for the data interpretation) is applied to the two electrical connections, and the impedance is determined based on the measurement of the resulting electric current through the electrodes and some mathematical calculation involving the magnitudes and phases of voltage and current. In such a situation, it is preferred to apply as small voltages as possible so that the impedance measurement does not affect the cell biological status. As a contrast, for electrically stimulating the cells, voltages applied to the electrodes should be sufficient to affect and modulate the transmembrane potentials of the cells. For example, depending on the geometry of the microfabricated electrodes in the wells, voltage pulses ranging from less than 1 V to more than 100 V could be applied. The waveform of the voltage pulses can also be varied. As a non-limiting example, a variety of voltage waveforms described in U.S. Pat. No. 6,686,193 could be used.

To generate electronic signals with suitable voltage waveforms and amplitude, suitable electronic signal generators are used or developed for such purposes. Signal generators may be capable of generating suitable electronic signals for stimulating the cells. For example, the signals can be appropriate periodic or aperiodic waveform (for example, single-polarity square wave, bi-polarity square wave, sine wave, triangular wave, exponential decay wave, or combination of above). For periodic waveform, the frequency of the signals can be from less than 1 Hz to more than 1 kHz. The magnitude of the signals can be varied, for example, from <1 V to >300 V. The signals can have any suitable length of time, for example, a series of square wave having period of 100 micro-second lasting from <1 ms to >100 ms. Preferably, the signal generator can be controlled from a computer so that any desired waveforms can be generated.

Electrodes in the electronic plates for electric stimulation of cells can have a variety of electrode geometry and be made of different materials (for example, thin conductive films). As a non-limiting example, electrode geometry and electrode materials thin film thickness ranges described in U.S. patent application Ser. No. 10/705,447, filed on Nov. 10, 2003, U.S. patent application Ser. No. 10/705,615, filed on Nov. 10, 2003, U.S. patent application Ser. No. 10/987,732, filed on Nov. 12, 2004 and U.S. patent application Ser. No. 11/055, 639, filed on Feb. 9, 2005, could be used.

In the electronic plates, the electrodes may be made thin, metal film materials. For various electrode geometry and thickness ranges of the thin metal films, the electrical voltages applied to the electrodes is actually smaller than the voltages coming out of the signal generator because of the electronic resistance (or impedance) of electrically conductive traces (of thin metallic film) from the connection pads or points on the electronic plates to the actual electrodes themselves. In such cases, the voltage amplitudes and waveform may need to be carefully chosen or designed so that the effects of these trace resistances are taken into account and the desired signal waveforms and amplitudes can be actually applied to the electrodes on the electronic plates.

In one aspect, the present invention is directed to a device for monitoring a cell or cell population comprising: a) a nonconductive substrate; b) a plurality of electrode arrays positioned on the nonconductive substrate, wherein each electrode array comprises at least two electrodes, further wherein each electrode is separated from at least one adjacent electrode by an area of non-conductive material; and c) at least one set of electrostimulation electrodes, said electrostimulation electrodes capable of affecting cell membrane potential. The change in membrane potential may result in opening or closing of a voltage gated ion channel. In some embodiments, a first half of electrostimulation electrodes may be in the plane of the substrate and a second half of the set of electrodes may be outside the plane of the substrate. In some embodiments, the nonconductive substrate is a porous substrate that is located above one half of the at least one set of electrostimulation electrodes.

In some embodiments, the device includes a plate including multiple wells, further wherein at least one of the multiple wells includes a top, bottom and sidewall, further wherein the bottom and the sidewall are constructed from the nonconductive substrate, further wherein the plurality of electrode arrays are positioned at the bottom, further wherein a first half of the at least one set of electrostimulation electrodes are positioned at the bottom and a second half of the at least one set of electrostimulation electrodes are positioned at the top. The electroporation or electrostimulation electrodes at the top may take the form of a disc electrode or an electrical wire. Examples include a device having a 96 well, a 384 well or 1536 well configuration, which may have dimensions and footprint same as those of standard microtiter plates. The multiple wells are capable of electrostimulating cells together or separately. In some embodiments, the plate is capable of stacking on top of a second plate.

Appropriate mechanisms are needed to connect electronic plates to the signal generators. For example, electrodes from individual wells may be selectively addressed and connected to signal generators so that the cells in individual wells can be selectively stimulated. For such individual well selection, electronic control circuits are used so that electronic switches (e.g., relays) can be turned on or off to connect electrodes from individual wells to the signal generators. For certain applications, this is a preferred approach in that stimulation of cells with electronic signals in each well can be synchronized with appropriate detection or measurement methods.

For example, cells in the wells of an electronic plate are stained with dyes that are sensitive to the transmembrane potentials. The plate is connected electronically to an instrument that is capable of selectively address electrodes from each well to signal generators. Simultaneously, the plate is on an optical measurement stage so that the fluorescent signals from each well can be read in a sequential fashion by moving the optical detector head or optical stage. In operation, the optical detector is positioned at a first well to be measured. The electronic signals are applied to the first well to stimulate the cells. During and/or after the cells being electrically stimulated (i.e. electrical stimulation pulses or waveforms are applied to electrostimulation electrodes to result in a change in cell membrane potential), the optical measurement of cell responses (in this example, the measurement of cell membrane potential) to the electrical stimulation of the cells in the first well is conducted. After the first well is assayed, the optical detector head is moved to a second well. The electrical signals are applied to the second well to stimulate the cells in the second well. During and/or after the cells being stimulated, the optical measurement of cell responses to the electrical stimulation of the cells in the second well is conducted. This process is continued until the end when the cells in all the wells have been measured. In this example, there is a synchronization between the application of electrical signals and the optical measurements of the cells. In this example, optical measurement is used to monitor and assay cell responses to electrical stimulations. The assays in this example can be conducted in the presence of inhibitors of voltage-gated ion channels. As described above, many other ion channel assay technologies can also be used for the present application.

In other example, electrical signals can be applied to multiple wells at the same time so that the cells in these wells are stimulated. Suitable detection methods are then applied to measure the responses of the cells in individual wells. In some cases, the detection method may be used for monitoring the responses from individual cells.

In another aspect, the present invention is directed to a method of monitoring the effect of a compound on an ion channel, including: providing a device capable of monitoring impedance of a cell or cell population and capable of inducing a change in a cell membrane potential; adding a cell or cell population comprising a voltage gated ion channel to the device; adding a test compound to the device; inducing a change in a cell membrane potential; and monitoring the impedance. Monitoring the impedance may be conducted before, during, after, or before and during and after adding the test compound the device. Monitoring the impedance may be conducted before and after inducing the change in cell membrane potential. The cell or cell population may further be monitored optically or by other means to measure cell membrane potential or other ion-channel activity associated parameters before and after inducing a change in cell membrane potential. In an exemplary embodiment, monitoring cell membrane potential is performed using an optical detection method after an optically detectable compound is added to the device. For example, a cell or cell population may be observed by detecting a membrane-potential-sensitive fluorescent dye added to the cell or cell population. Assessing or measuring cell membrane potential or other ion-channel activity-associated parameters may be performed at the same time as, or different times from, monitoring the impedance of cell population. The change in membrane potential may result in opening or closing of a voltage gated ion channel. A cell index or normalized cell index may be determined and may be compared to the same cell or cell population or may be compared between different cells or cell populations.

In another aspect of the present invention, a method of identifying an ion channel inhibitor is provided including providing a microlectronic cell sensor array operably connected to an impedance analyzer, the microelectronic cell sensor array including a non-conductive substrate, a plurality of electrode arrays positioned on the substrate, each electrode array including at least two electrodes, and each electrode is separated from at least one adjacent electrode by an area of non-conductive material. The device is capable of affecting the membrane potential in a cell or cell population such that a voltage gated ion channel may open or close. A suspected inhibitor is added to a cell or cell population, the membrane potential is affected and the cell or cell population is monitored to determine whether a voltage gated ion channel has opened or closed.

EXAMPLES

Example 1

Transfection of RNAi into SKOV3 Cells

Previous studies have reported transfection cytotoxicity as one of the difficulties in using RNAi (or siRNA). Current transfection methods include optimization of particular RNAi transfection reagents and conditions for a cell type and gene of interest. The present example demonstrates an electroporation method having very good recovery and little cytotoxicity.

SKOV3 cells were acquired from ATCC (Manassas, Va.) and maintained in McCoy's media (ATCC, Manassas, Va.)+ 10% FBS, in a 37 deg humidified chamber with 5% CO2. The day before electorporation, cells were lightly trypsiniex and plated at 5000 cells per well in ACEA's 16× electronic plate devices. On the bottom of the well, each well of the device comprises an electrode array having circle-on-line electrode geometry, having size of circle diameter of 90 micron, line width 30 micron and line gap of 80 micron. The details of circle-on-line electrode geometry are disclosed in U.S. patent application Ser. No. 10/705,447 entitled "Impedance Based Devices and Methods for Use in Assays", filed on Nov. 10, 2003, which is incorporated by reference. Cells were allowed to adhere and grow overnight. The day of the electroporation, media was changed to 50 uL Opti-MEM 1 (Gibco/Invitrogen, Carlsbad, Calif.) to equilibrate cells. Prior to electroporation, 10 uL of 240 nM siCy3-Luciferase GL2 duplex (Dharmacon, Boulder, Colo.) were added to give a final concentration of 40 nM. Cells were immediately electroporated by applying electrical voltage signals to the electrode arrays on the bottom of the well and allowed to recover for 2 hours in a 37 deg humidified chamber with 5% CO2. Complete media was then added for cells to grow overnight. Electrical signals used for electroporation were of sinusoidal waveform having frequencies between 10 and 50 kHz, amplitude between 10 and 20 V (peak-to-peak), waveform duration between 100 and 300 ms.

Figure 4A:
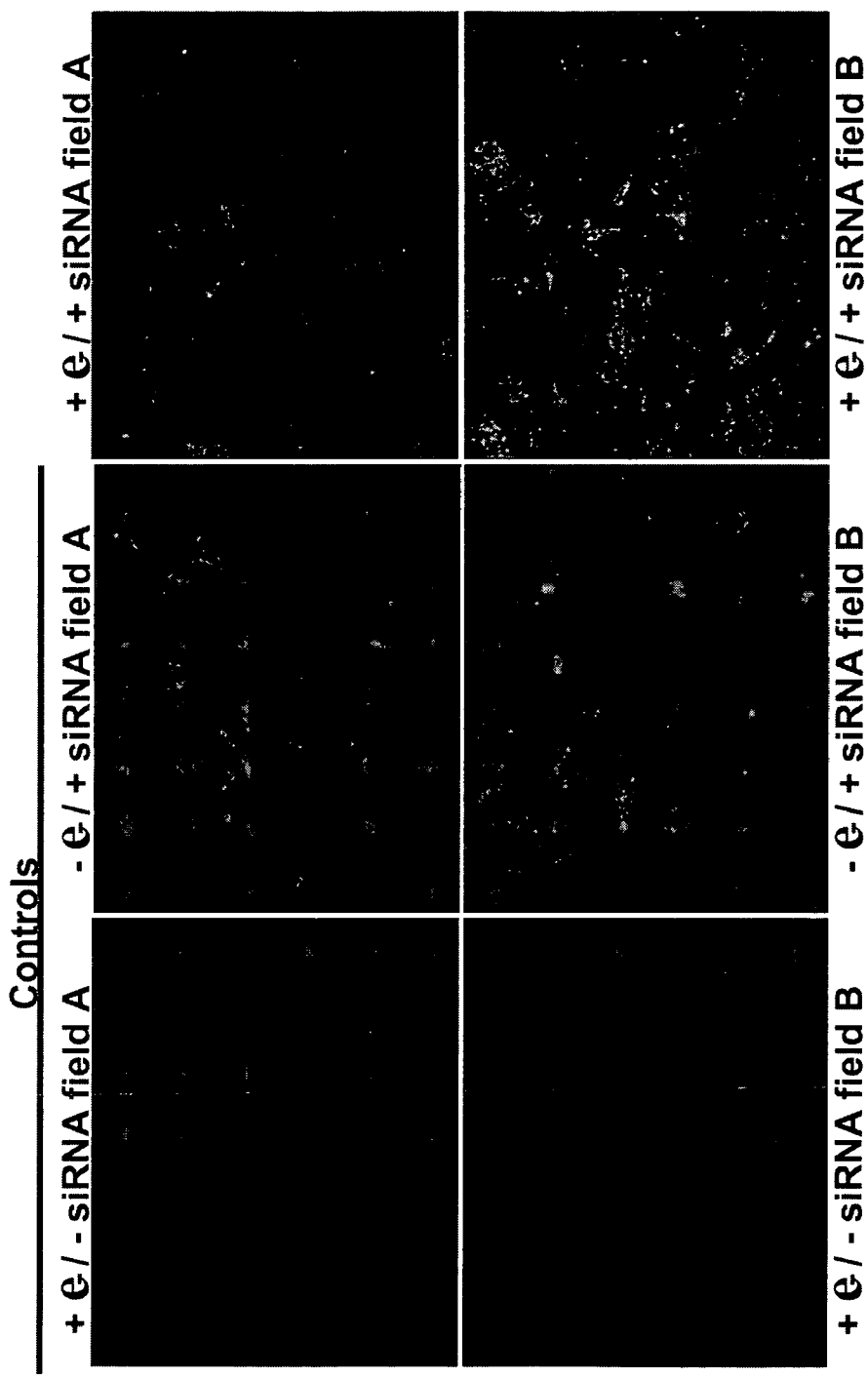
FIG. 4A shows fluorescent microscopy images of SKOV3 cells electroporated with siCy3-Luciferase GL2. $5 \times 10^3$ SKOV3 cells were plated on ACEA 16× electronic plate devices. A final concentration of 100 nM siCy3-Luciferase GL2 in Opti-MEM was overlayed on the wells and electroporated by applying electrical voltages to electrodes located at the bottom of the wells. Fluorescent images were taken 2 hours after electroporation. Two representative images are shown for experimental wells (+e/+siRNA), cells electroporated with siCy3-Luciferase GL2, and control wells (+e/−siRNA or −e/+siRNA), cells electroporated without siCy3-Luciferase GL2 or without electroporation but with siCy3-Luciferase GL2, respectively. For electroporation, the electrical voltages of sinusoidal waveform having 30 kHz frequency and 15 V peak-to-peak amplitude with a 300 msec duration were applied to the electrodes at the bottom of the wells.

To assess cell membrane permeabilization as a result of electroporation and to determine efficiency of transduction of RNAi into SKOV3 cells using electroporation, siRNA duplex conjugated to a fluorescent probe was used to monitor uptake into permeabilized cells. Cy3 labeled siLuciferase GL2 duplex was overlaid on a 16× microelectronic sensor plate covered with a near confluent layer of SKOV3 cells. Cells were electroporated and uptake of Cy3 labeled probe monitored 24 hours after electroporation using fluorescent microscopy. The amount of fluorescence in cells was used as a measure of uptake of fluorescent probe. Cells electroporated with siCy3-Luciferase GL2 showed increased Cy3 fluorescence relative to controls (FIG. 4A). This increase in fluorescence above background represents uptake of RNAi into cell as a result of transient permeabilization of the cell membrane due to an application of an electric field using the microsensor arrays.

Figure 4B:
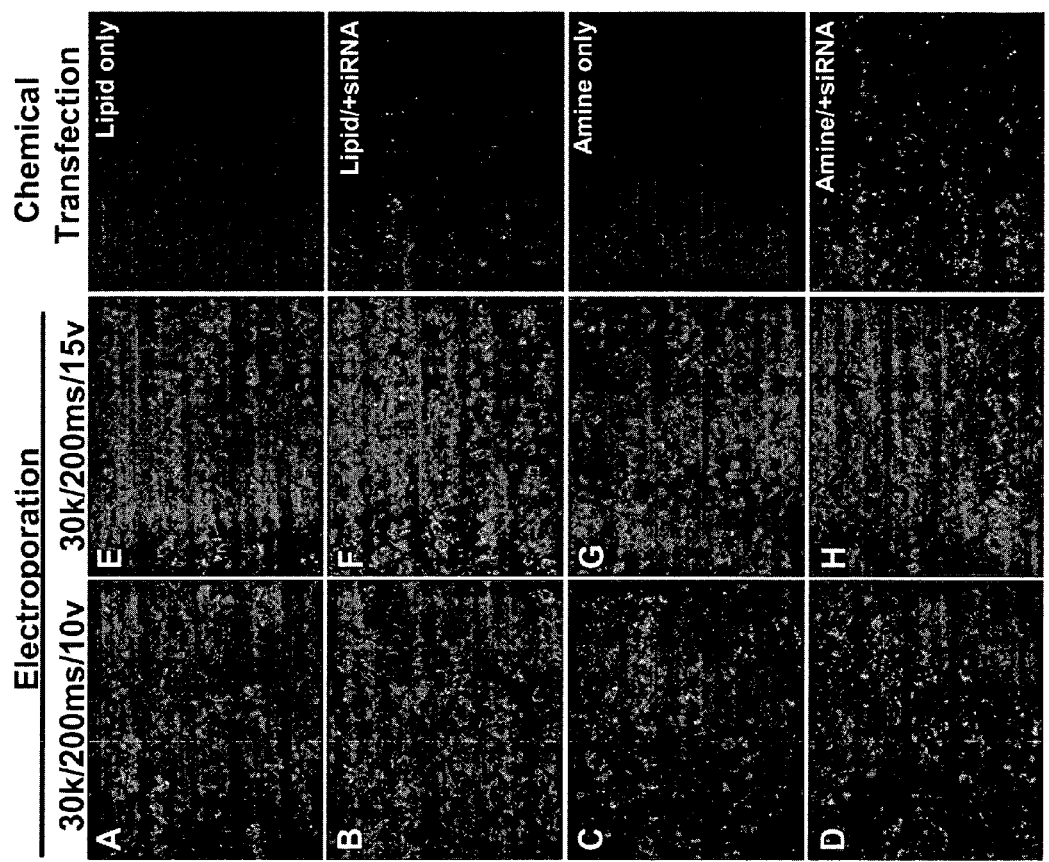
FIG. 4B shows fluorescent microscopy images comparing transfection of siCy3-Luciferase GL2 into SKOV3 cells using electroporation by applying electrical voltages to the electrode structures located at the bottom of the well and chemical transfection. Fluorescent images were taken 2 hours after electroporation. First and second columns are representative images of sequential wells (A-H) electroporated using two different electroporation conditions (sinusoidal voltage signals having 30 kHz frequency, 10 V peak-to-peak or 15 V peak-to-peak, duration of 200 ms) with 40 nM siCy3-Luciferase GL2. Third column shows representative images of cells transfected using lipid and amine based transfection reagents with 40 nM siCy3-Luciferase GL2.

To compare transfection efficiencies between electroporation and chemical transfection and to assess the effect of pulse length and field strength, cells were plated on 16× electronic plate devices as described and were either electroporated or chemically transfected using lipid or amine based reagents to introduce 40 nM siCy3-Luciferase GL2. Cells electroporated showed a more homogeneous and higher fluorescence signal compared to either lipid or amine based transfections. The intensity of fluorescence signal is directly dependent on voltage and time length of electorporation (FIG. 4B). Cells electroporated with higher pulse length or field strength showed a higher fluorescence as a result of increased uptake of siCy3-Luciferase GL2, probably due to more efficient permeabilization of the cell membrane.

Figure 5A:
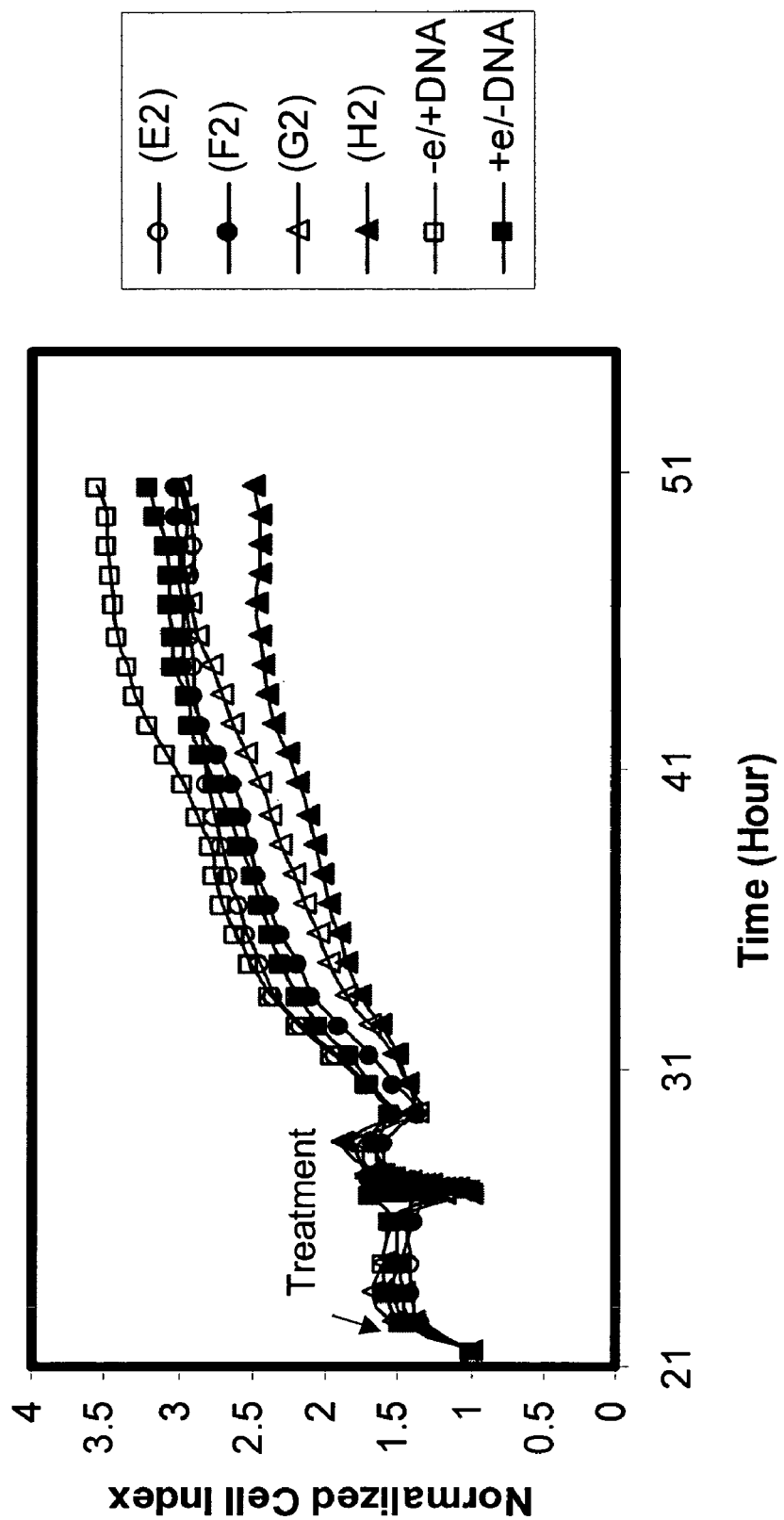
FIG. 5 shows dynamic monitoring and comparison of cytotoxicity effects of electroporation and chemical transfection of siCy3-Luciferase GL2 into SKOV3 cells using ACEA Real Time Cell Electronic Sensing system. A) Cell index measurements before and 24 hours after electroporation of SKOV3 cells with 40 nM siCy3-Luciferase GL2 in different wells (E2-H2) and including control wells (+e/−siRNA, −/+siRNA), cells electroporated without siCy3-Luciferase GL2 or without electroporation but with siCy3-Luciferase GL2, respectively. For electroporation, the electrical voltages of sinusoidal waveform having 30 kHz frequency and 15 V peak-to-peak amplitude with a 300 msec duration were applied to the electrodes at the bottom of the wells. B) Cell index measurements before and 24 hours after chemical transfection of SKOV3 cells with 40 nM siCy3-Luciferase GL2 using lipid and amine based transfection reagents, and including control wells (+e/−siRNA, −e/+siRNA), cells electroporated without siCy3-Luciferase GL2 or without electroporation but with siCy3-Luciferase GL2, respectively. For electroporation, the electrical voltages of sinusoidal waveform having 30 kHz frequency and 15 V peak-to-peak amplitude with a 300 msec duration were applied to the electrodes at the bottom of the wells.
Figure 5B:
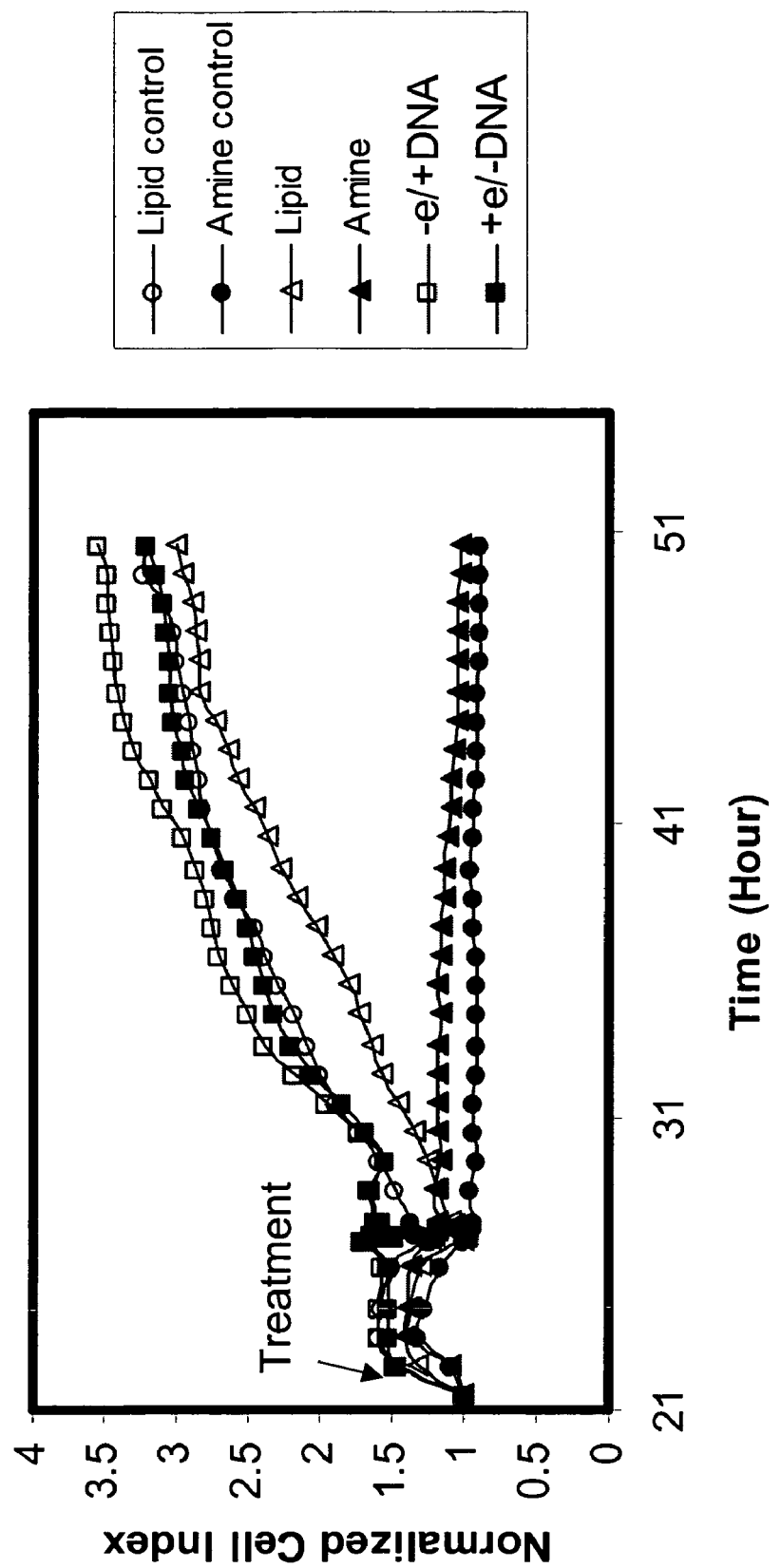

Transfection procedures are usually associated with a certain degree of cytotoxicity. Similar to other transfection protocols, electroporation may also induce cell death due to numerous factors including heat generated during the procedure and loss of intracellular ions from permeabilized membrane. Unlike conventional electroporation methodologies, the device, system and methods described in the present invention allow for continuous and dynamic monitoring of cells prior to, during and after electroporation. Cells were monitored before and 24 hours after transfection to assess recovery and compare cytoxicity from electroporation and chemical transfection (FIG. 5). Cells that were electroplated showed very good recovery from the treatment and little cytotoxicity as measured by the increase in cell index over 24 hours. Cells that were transfected with amine, which showed better transfection efficiency (FIG. 4B), had poor survival compared to cells transfected with lipid, while cells transfected with lipid have comparable survival to electroporated cells (FIG. 5).

Example 2

Cell Culture, Electroporation and Quanitation of Transfection Efficiency

MCF-7/GFP cells stably transfected with a vector expressing green fluorescent protein fused to tubulin (GFP-tubulin) is used as the primary cell line for optimization of electroporation conditions in 384 well plates. Details of 384 well plates are provided in Example 4: Adaptation of a Microelectronic Plate and Instrumentation Allowing Electroporation and Real-Time Impedance Monitoring, of the present invention. The presence of GFP in the cell line provides a useful reference to assess optimal electroporation conditions for transfection of molecules. Transfection efficiency is measured as the amount of reduction in green fluorescence as a result of siRNA uptake. MCF-7/GFP cells are maintained in DMEM supplemented with 10% fetal bovine serum and 500 ug/mL G418. In general, cells are plated on 384 well plates and allowed to adhere overnight. The following day, cell culture media is be changed to cold electroporation buffer, siRNA specific to GFP added and the cells electroporated. After electroporation, cells are allowed to recover at 4 deg C. for a few minutes; buffer replaced with growth media and returned to a humidified 37 deg C., 5% CO2 chamber for incubation.

To asses the transfection efficiency, cells on day 2 and day 4 post-transfection are washed with PBS, fixed in 4% paraformaldehyde (PFA) in PBS for 10 min, washed in PBS again to remove excess PFA, and analyzed using an epifluorescent microscope. Several representative fields for each experimental sample are randomly chosen. Successfully transfected cells have a decreased or no green fluorescence detected. In addition, to monitoring efficiency of transfection, cells are concurrently monitored for cytoxicity and cell viability. This is done using the ACEA RT-CES (Real Time Cell Electronic Sensing) system (ACEA Biosciences, San Diego, Calif., USA), which provides a useful platform for the continuous monitoring of cells during pre- and post electroporation.

Studies show that a high concentration of cell suspension and components to be transfected in a fixed volume or local area is necessary for efficient transfection. To determine the optimum range of cell number and siRNA concentration necessary to achieve transfection, a matrix including a range of cell number against varying siRNA concentrations are plated on a matrix format in 384-well plates at a minimal volume and electroporated. Transfection efficiency is assessed using fluorescent microscopy and cell viability assessed by the ACEA RT-CES system (ACEA Biosciences, San Diego, Calif., USA).

Electroporation has precluded widespread use because of its high cytotoxicity. A rising ambient temperature, created during electroporation, might have a detrimental effect on the cells. The generated heat is regarded as the cause of cell loss found in commercial equipment. In addition, cell loss has been also attributed to leakage of intracellular ions from transiently open pores created during electroporation. To decrease cell cytotoxicity due to ionic loss and heat generated during electroporation while concurrently increasing transfection efficiency, several cold buffer conditions are tested that balance the amount of cytotoxicity and facilitate transfection. High potassium and magnesium salt solution are substituted for standard high sodium chloride salt solution. This buffer condition has been show to enhance cell survival. By providing an equilibration condition that minimizes the intracellular loss of ions during electroporation when pores occur in the cell membrane, and also enhance transfection efficiency. In addition different osmotic conditions are tested to test efficiency of transfection. Studies show that the use of hypo osmolar buffer during pulsing allows for more efficient loading of cells especially with larger molecules. Transfection efficiency may be assessed using fluorescent microscopy and cell viability assessed by the ACEA RT-CES system.

The efficiency of electroporation is affected by the electrical properties of the cells being electroporated; these include the shape and size of the cell, membrane potential, and intracellular ionic composition. Increasing voltage and pulse duration generally results in an increase in transfection efficiency, but if voltage and pulse duration are too large, the transfection efficiency could reach a critical point wherein the cells become irreversibly damaged and transfection efficiency decreases. It is therefore necessary to test a range of pulse frequency, voltage and pulse duration that determine this specific threshold and identifies an optimum transfection condition. Correspondingly, the parameters should vary between about 10 Hz to about 1 MHz, 1V to about 50 V peak-to-peak, and 50 micro-seconds to about 5 seconds. The optimized condition may be determined for each cell line based on the best transfection efficiency as well as lowest cell viability loss. To assess the optimum condition for each parameter, experiments are set-up by keeping two of the parameters constant and testing a range for the third parameter. This will be repeated until all three parameters have been systematically checked. Transfection efficiency may be assessed using fluorescent microscopy and cell viability assessed by the ACEA RT-CES system.

Once electroporation conditions in the 384 well electronic plate device has been optimized, two cell lines including a primary cell line is to be chosen to optimize assay protocols for electroporation and assessing cell proliferation, cell viability and receptor ligand interactions.

To demonstrate the utility of the 384 well electronic plate device in electroporation and monitoring of cellular status A431 epidermoid carcinoma cells are seeded in the wells of 384 electronic plate device and the siRNA for the epidermal growth factor (EGFR) will be electroporated at various concentrations. As a control a scrambled siRNA is also electroporated into cells. Cellular proliferation is monitored on the RT-CES system as described by Solly et al. (Solly, K., Solly, K., Wang, X., Xu, X., Strulovici, B. & Zheng, W., 2004, *Assay Drug Dev Technol*, Vol: 2, pp: 363-372). Introduction of EGFR siRNA into A431 cells has been shown to lead to a decrease in cellular proliferation due to an increase in apoptosis (Nagy, P., Arndt-Jovin, D. J. & Jovin, T. M. 2003, *Exp Cell Res*, Vol: 285, pp: 39-49). It is expected that siRNA targeting the EGFR in A431 cells will lead to a time-dependent decrease in proliferation of A431 cells. Alternatively, an expression vector encoding for EGFR can be overexpressed in A431 cells and its function implications can be assessed in a proliferation assay as described above.

Vascular endothelial growth factor (VEGF) is a potent inducer of endothelial cell proliferation and angiogenesis and its effect is mediated through VEGF receptor 1 (R1) and or 2 (R2) (Cross, M. J., Dixelius, J., Matsumoto, T. & Claesson-Welsh, L. 2003, *Trends Biochem Sci*, Vol: 28, pp: 488-94). The role of VEGF R1 and R2 are assessed in the primary human umbilical vein endothelial cells (HUVEC). HUVECs are cultured on the electronic plate device and electroporated with siRNA targeting the VEGFR1 or the VEGFR2 receptors and its functional effect is determined by assessing proliferation of HUVECs in the presence of VEGF. As a control a scrambled siRNA is electroporated into the cell. Once again, it is expected that both VEGFR1 and R2 downregulation by the siRNA will lead to a decrease in VEGF-mediated HUVEC cell proliferation (Kim, B., Tang, Q., Biswas, P. S., Xu, J., Schiffelers, R. M., Xie, F. Y., Ansari, A. M., Scaria, P. V., Woodle, M. C., Lu, P. & Rouse, B. T. (2004). *Am J Pathol*, 165, 2177-85). The extent of down regulation of EGFR and VEGFR1 and R2 in their respective cells can be assessed by RT-PCR to evaluate the down regulation of the mRNA or by western blot to assess the down regulation of EGFR1 and VEGRR1 and R2 proteins.

Both VEGF and EGF lead to dramatic cytoskeletal remodeling and morphological changes in HUVEC cells and A431 cells, respectively (Kurokawa, K., Itoh, R. E., Yoshizaki, H., Nakamura, Y. O. & Matsuda, M. 2004. *Mol Biol Cell*, Vol: 15, pp: 1003-10, Rousseau, S., Houle, F., Landry, J. & Huot, J. 1997. *Oncogene*, Vol: 15, pp: 2169-77). The siRNAs targeting EGFR and VEGF R1 and R2 described above can also be sued to assess the functional effect of these receptors in cytoskeletal rearrangement, which can be easily measured by the RT-CES system. The siRNA is electroporated as described above following by serum starvation of the cells. EGF or VEGF is added to the appropriate cells and the cytoskeletal changes taking place in the 384 well electronic plate device is continuously monitored. Cells electroporated with the specific siRNA targeting EGFR and VEGFR1 and R2 is expected to lead to a significant decrease in cytoskeletal rearrangement as measured by the RT-CES system Example 3

Real Time Monitoring of RNAi Function in Transfected Cells

The day before electroporation, cells were lightly trypsinized and plated at 5000 cells per well. Cells were allowed to adhere and grow overnight. The day of electroporation, media was changed to 50 µL Opti-MEM I (Gibco/Invitrogen, Carlsbad, Calif.) to equilibrate cells. Prior to electroporation, 10 µL of 240 nM siCy3-Luciferase GL2 duplex (Dharmacon, Boulder, Colo.) were added to give final a concentration of 40 ηM. Cells were immediately electroporated and allowed to recover for 2 hours in a 37 deg humidified chamber with 5% $CO_2$. Complete media was then added for cells to grow overnight.

Figure 6:
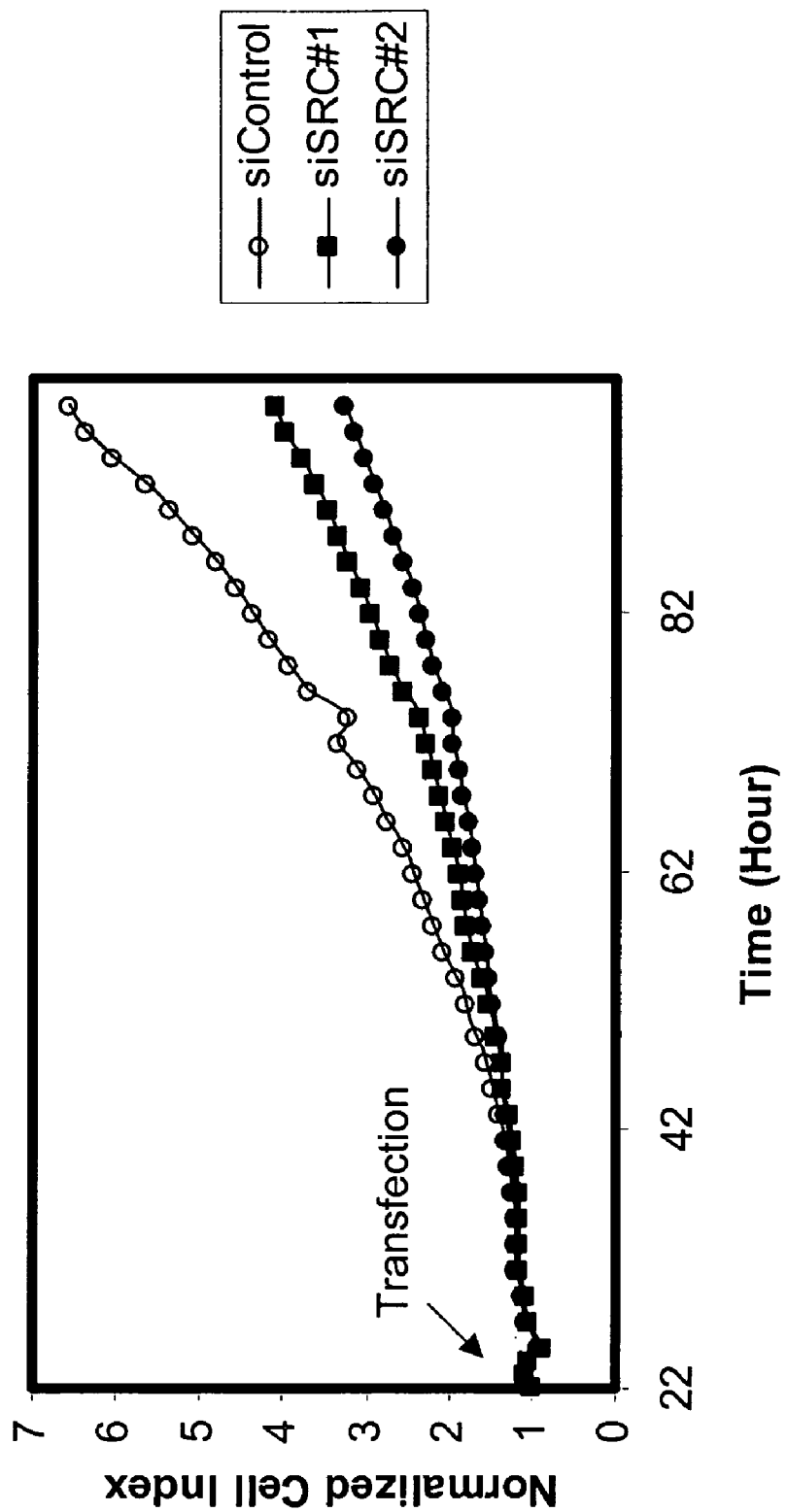
FIG. 6 shows dynamic monitoring of BxPC3 cells transfected with siSRC over 4 days. $10 \times 10^3$ BxPC3 cells were plated overnight and transfected with 20 ηM siSRC the following day using standard lipid-mediated transfection procedures. Average cell indices of 4 wells transfected with siSRC duplexes or siControl were plotted over 4 days.

In the first example, BxPC3 cells were seeded at 5000 cells per well of special microtiter plates (16× E-Plates) integrated with interdigitated microelectrodes. About 22 hours later, the cells were transfected with siRNA's directed against the c-Src mRNA (siSrc#1 and siSrc #2, FIG. 6) using standard lipid-mediated transfection procedures. Transfection was directly performed in the wells of the E-Plate which is adapted for use with the RT-CES system. The viability and proliferation of BxPC3 cells was continuously monitored after transfection using the RT-CES system. According to FIG. 6, it is apparent that both siSrc#1 and siSrc#2 significantly affected the proliferation of BxPC3 cells relative to control siRNA transfected cells.

Figure 7:
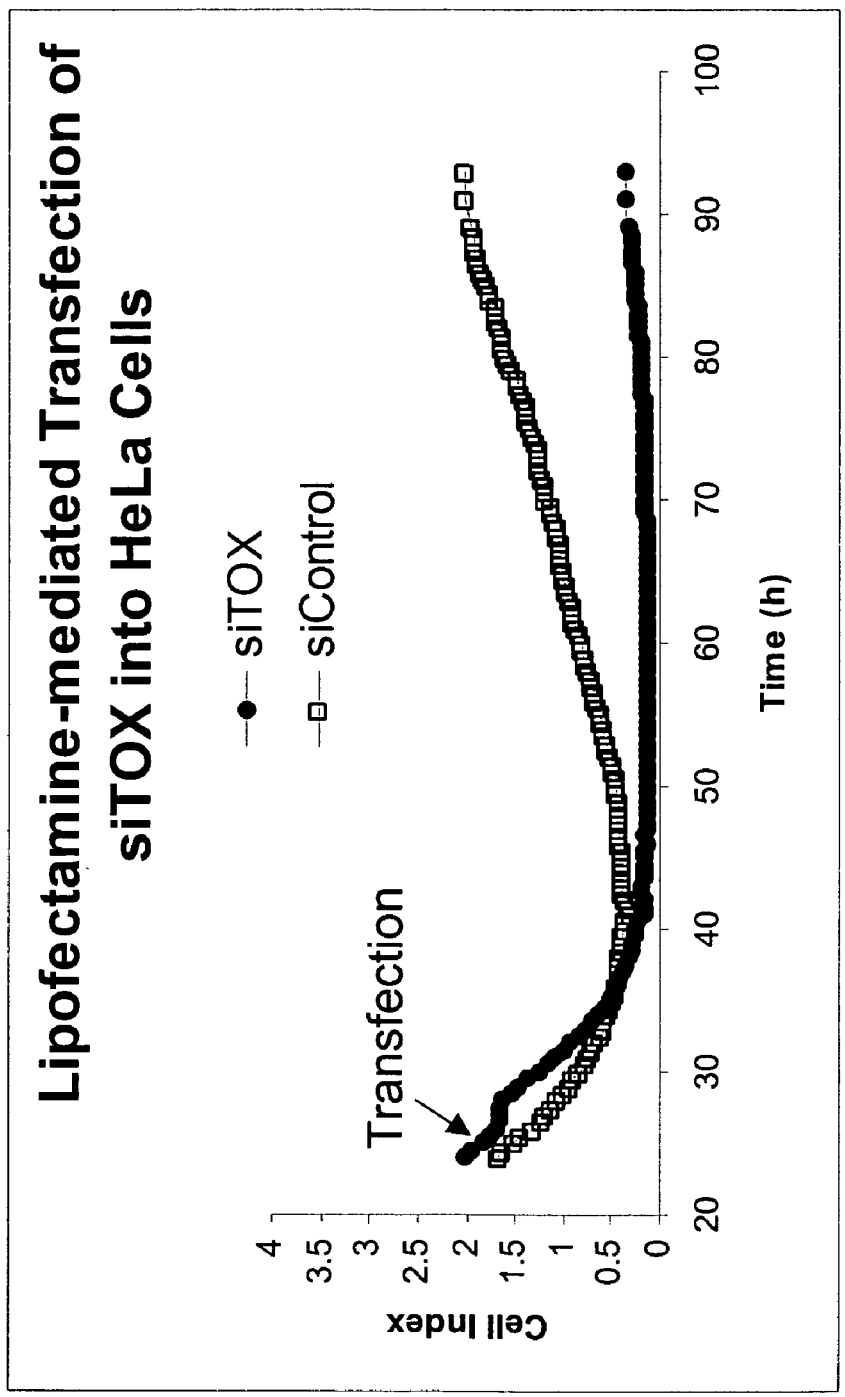
FIG. 7 shows dynamic monitoring of HeLa cells transfected with siTOX siRNA or control siRNA siControl over 3 days after lipofectamine-mediated transfection. HeLa cells were seeded in ACEA 16× E-Plates at a density of 5000 cells per well and the cells were allowed to attach and grow for about 18 hours. The cells were then transfected using standard lipid-mediated transfection procedures with 100 nM siTOX siRNA (Ambion) or 100 nM of siControl siRNA. The siTOX siRNA induces cell death and apoptosis upon uptake by the cells. siTOX transfection leads to an eventual decrease in Cell Index of HeLa cells.

In another example, HeLa cells were seeded in E-Plates at a density of 5000 cells per well and the cells were allowed to attach and grow for about 18 hours. The cells were then transfected using standard lipi-mediated transfection procedures with 100 nM siTOX siRNA (Ambion) or 100 nM of siControl siRNA. The siTOX siRNA induces cell death and apoptosis upon uptake by the cells. As shown in FIG. 7, siTOX transfection leads to an eventual decrease in Cell Index of HeLa cells. Cell Index is an indicator of cell viability and therefore the experiment shows that the RT-CES system can be used to quantitatively and specifically assess the effect of siRNA on cells.

Figure 8:
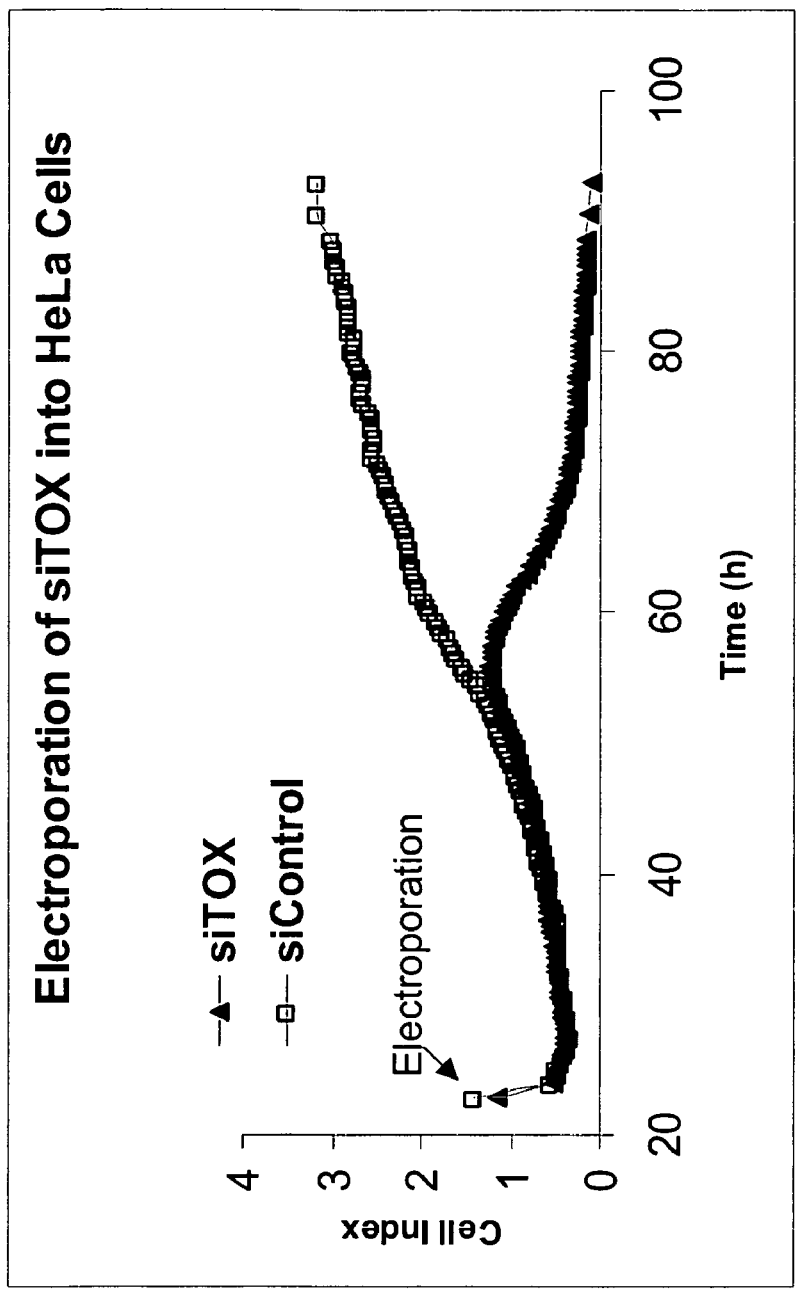
FIG. 8 shows dynamic monitoring of Hela cells transfected with siTOX siRNA or control siRNA siControl over 3 days after electroporation-mediated transfection. HeLa cells were seeded in ACEA 16× E-Plate devices at a density of 5000 cells per well and the cells were allowed to attach and grow for about 18 hours. The E-Plate devices were connected to a voltage signal generator (or electroporator) and the cells were electroporated in the presence of 100 nM of siTOX and siControl siRNAs. The cells were continually monitored after electroporation. siTOX electroporated cells lose cell viability as measured by an eventual decrease in Cell Index.

Another example shows the dynamic monitoring of Hela cells transfected with siTOX siRNA or control siRNA siControl over 3 days after electroporation-mediated transfection. HeLa cells were seeded in ACEA 16× E-Plate devices at a density of 5000 cells per well and the cells were allowed to attach and grow for about 18 hours. The E-Plate devices were connected to a voltage signal generator (or electroporator) and the cells were electroporated in the presence of 100 nM of siTOX and siControl siRNAs. The electroporation was conducted by applying voltage pulses between a top electrode (about 4 mm in diameter) and the electrode array on the bottom of the well. Here, the top electrode was made from a copper disc. It was placed into the well to be in contact with the media in the well and located about 2 mm from the bottom of the well, and used as one electrode for electroporation. The electrodes on the bottom of the well, normally used for cell-substrate impedance measurement, were connected together and used for the other electrode for electroporation. Thirty consecutive square voltage pulses having 10 micro-second duration and 35 V in amplitude, separated by 500 milli-second between neighboring pulses were applied to the top and the bottom electrodes for electroporation. The cells were continually monitored after electroporation. According to FIG. 8, siTOX electroporated cells lose cell viability as measured by an eventual decrease in Cell Index.

Example 4

Adaptation of a Microelectronic Plate and Instrumentation Allowing Electroporation and Real-Time Impedance Monitoring The electroporation devices were adapted from a proprietary microelectronic Microtiter plates, referred to as an E-Plate™. In summary, microelectronic arrays suitable for electroporation applications are fabricated on a substantially flat substrate to form an electroporation chip. The electroporation chip is then assembled to specially made, bottomless microtiter plates so that a microelectrode array is incorporated into the bottom of each well.

Figure 9:
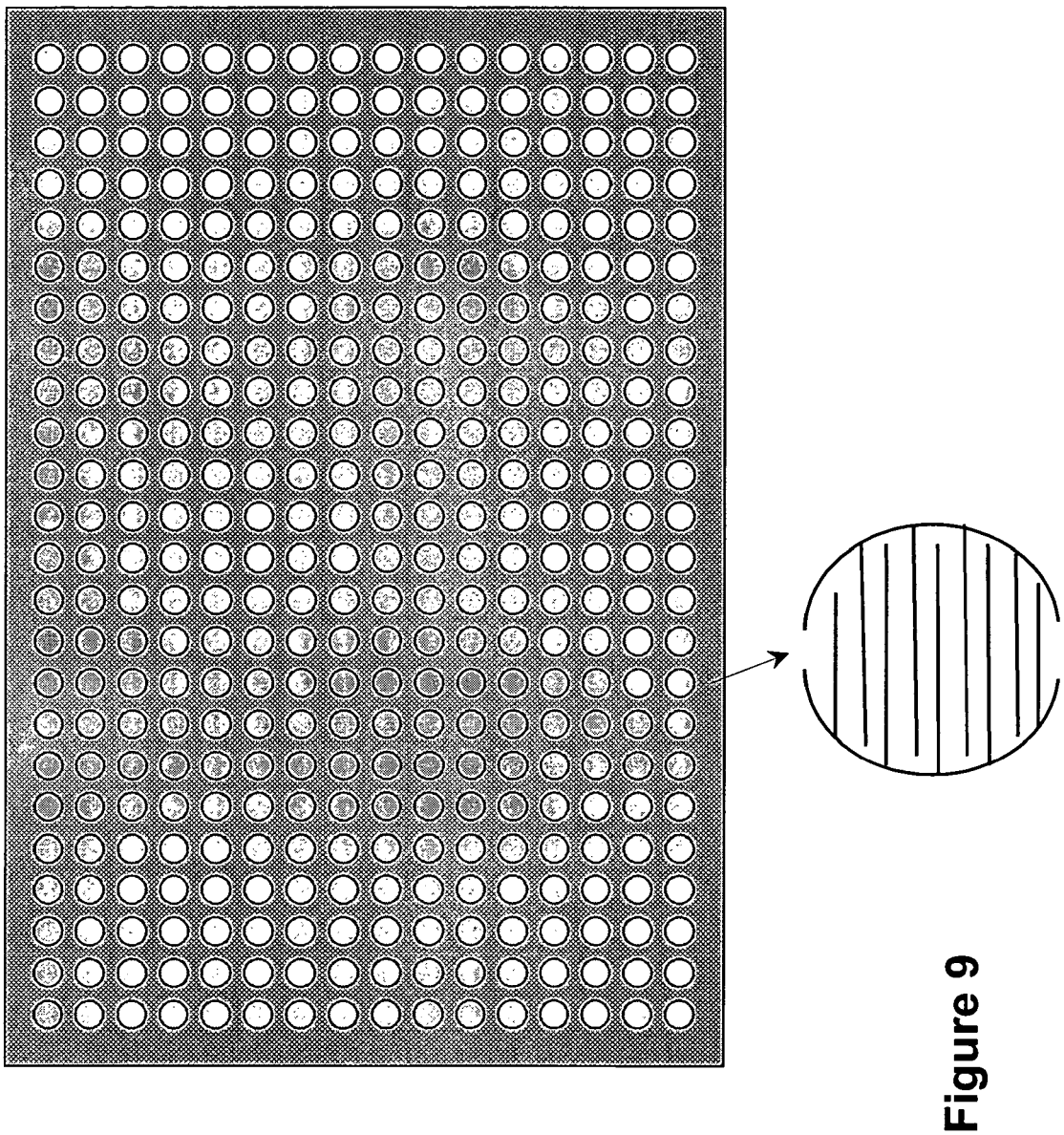
FIG. 9 shows a schematic drawing of a 384-unit electroporation device with individual unit consists of parallel electrode elements

For the 384× electroporation plates, microelectrodes are miniaturized on a substrate having dimensions of about 110 mm by about 75 mm. The spacing between adjacent units is about 2.25 mm. Each unit may include an identical microelectrode array and may be capable of producing an electric field to achieve cell electroporation and to monitor or measure cell attachment and growth over the electrode array region. FIG. 9 shows a schematic drawing for a 384-unit electroporation device with individual unit consisting of parallel electrode elements. For such devices, electrical voltages are applied to parallel electrode arrays within individual units. Each unit is associated with an individual well.

Chips with eight electrode geometric shapes may be designed fabricated and evaluated in order to select an electrode design with maximum electroporation-induced transfection efficiency as well as minimal loss in cell viability. Because the transfection efficiency and cell viability depends on the local electrical filed distribution, parameters affecting such field distribution may be tested. Variation in the electrode geometry may include electrode width (for example, 20-100 um) and ration of electrode width to gap (for example 1:1 to 1:0.2).

Chip fabrication on plastic substrates may be performed using standard photolithography processes. Fabrication may start with clean plastic substrate which is then vacuum-evaporated with an adhesion chromium layer of about 10 nm thick, followed by a 0.15 um thick gold film layer. Photoresist (S1830, Shipley) is spin-coated on to the gold film to 1 um thickness and then exposed to UVB light through a mask containing an image of the required electrode array. The exposed resist is developed using MF351 developer (Shipley), and the gold and chrome layers are etched subsequently with KI/I2 and K3Fe(CN)6/NAOH, respectively. Masks are produced commercially using electron-beam writing techniques on ultra-high resolution plates.

A challenge in the developing and producing 384× electroporation plates lies in connecting the microelectrodes from all wells to external electronic signal sources. Theoretically, if all the wells are independently addressed, one would have 768 lines with two lines from each well. The present invention includes approaches to address this challenge:

1) multiplexing of lines going to wells can be used. The number of lines may be reduced from about 768 to about 40 lines. Using this technique, each electroporation unit will not be individually addressed. Instead, common lines between some neighboring wells may be implemented.

2) Instead of providing connections from the top surface of the chip, connections to each well may be achieved on the bottom surface. Thus, plated-through holes will be used to make connections from the top surface to the bottom surface.

Thus, the bottom surface of the chip (i.e. the surface opposite to where the microelectrode arrays are located) is used for electronic connections by using electrically-conductive "via" between the bottom surface and the surface where the electrodes are located. Such conductive "via" can be pre-produced on plastic substrates by drilling holes at locations adjacent to each unit and then electrically or electrochemically plating these holes with appropriate conductive materials. During the chip fabrication, the electrical via on the electrode-array surface side will be directly interfaced with the connections from individual units. The electrical conductive via on the bottom surface of the chip can be readily connected to the chip edges or other connection locations through printed-circuit traces. For 384 units arrayed in the 16 rows by 24 columns, each unit has two connection lines, one of which is shared for all the units in the same row and the other of which is shared for all the units in the same column. In this way, we would have only 40 connections. By selectively addressing voltage signals to the shared lines for the column and row, individual units can be addressed with voltage signals.

The electroporation instrumentation has two primary components. One is a signal generator for the generation of electrical voltage signals for electroporation of adherent cells on the microelectrode arrays. Another is an interfacing apparatus between the instrument and the electroporation plates.

Example 5

Figure 10:
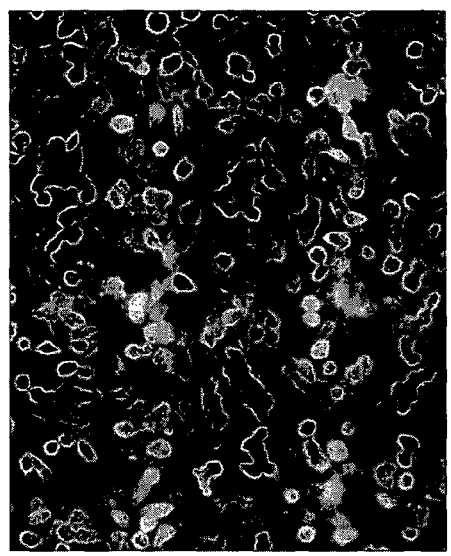
FIG. 10A shows image of the HT1080 cells that were cultured on an electronic plate overnight and were electroporated with a 10 kHz sine wave signal of 10 V peak-to-peak with pulse duration of 100 ms in the presence of Lucifer yellow dye. The cells show bright fluorescence, reflecting the fact that the cell membranes were electroporated as a result of large induced membrane potential, and that the Lucifer yellow dyes had entered the cells.
FIG. 10B shows the image of the HT1080 cells that were cultured in the wells to which no electric voltages were applied. The Lucifer yellow dye was also added to the wells.
Figure 10:

Modulation of a Cellular Transmembrane Potential and its Effects on Ion Channels To demonstrate the ability to apply electrical fields to stimulate cells in the wells of an electronic plate, we applied signals of sine waveforms having frequency 10 kHz with amplitude of 10 V peak-to-peak, having various duration between 10 and 300 ms (milli-seconds). The voltage applied here is so large that the induced transmembrane potentials of the cells have resulted in the electric breakdown of cytoplasmic membrane, leading to the well known electroporation effect. For visualization, a fluorescent dye (Lucifer yellow) was added into the cell media. When the electroporation of the cell membrane occurs, the dyes will enter the cells and can be observed. HT1080 cells were cultured on an ACEA 16× electronic plate over night and were stimulated with a 10 kHz sine wave signal of 10 V peak-to-peak with pulse duration of 100 ms. These cells showed bright fluorescence, reflecting the fact that the cells were electroporated as a result of large, induced membrane potential, and that the dyes had entered the cells as opposed to wells in which no electric voltages were applied. Such cells exhibit low florescent intensities, reflecting only the non-specific binding of dyes to the cell membrane. FIGS. 10A and 10B clearly demonstrate that it is possible to manipulate the transmembrane potential of cells on an electronic plate.

Example 6

Real-Time Monitoring of Cells on RT-CES System

ACEA's Real Time Cell Electronic Sensing (RT-CES™) system allows for for real-time, continuous monitoring and sensing of the cells through the measurement of cell-electrode impedance. At the core of the system is a 16× or 96× multi-well electronic microtiter plates, where the individual wells of the plates comprise cell-sensing microelectrode structures located on the well bottom surfaces. Adherent cells are cultured on the surfaces of microelectrode structures. The presence and absence of cells on the electrode surface sensitively affect the electronic and ionic passage between cell culture media and the electrode structures. Thus, interrogating the electrode impedance provides important information about biological status of the cells present on the electrodes. A wide range of cell-based assays can be performed on the RT-CES system, including cell proliferation assay, cell adhesion assay and cytotoxicity assay, anti-cancer compound efficacy screening and patterning, cellular differentiation analysis, receptor-ligand signaling assays, environmental toxin monitoring and detection.

Figure 11:
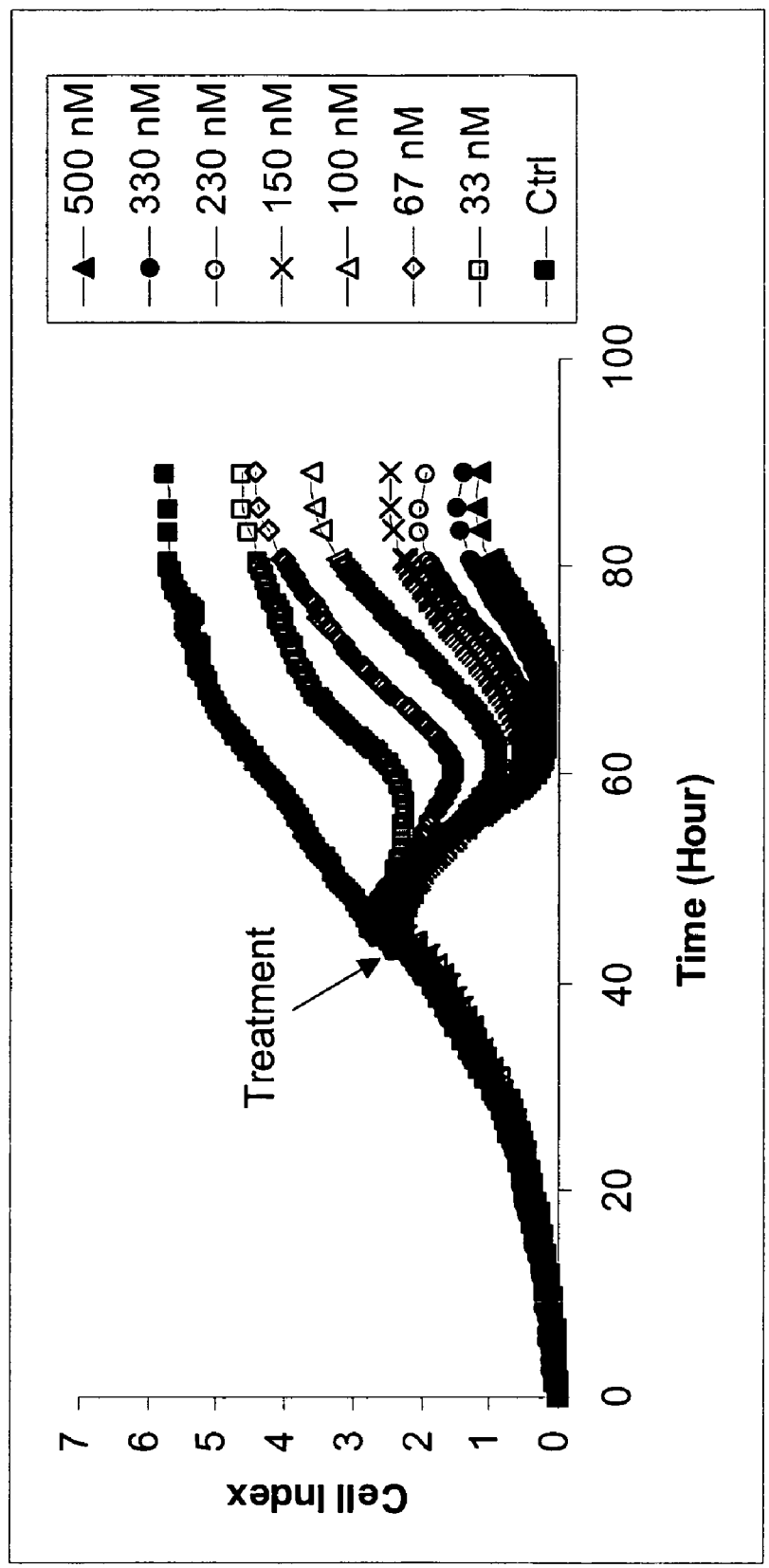
FIG. 11. shows real-time monitoring of cancer cells treated with paclitaxel. Real-time monitoring in cell-based assays allows the user to determine when is the best time to perform a certain treatment. In addition, real-time monitoring offered by the RT-CES system also allows the user to observe the mode of compound interaction with the target cells.
Figure 12A:
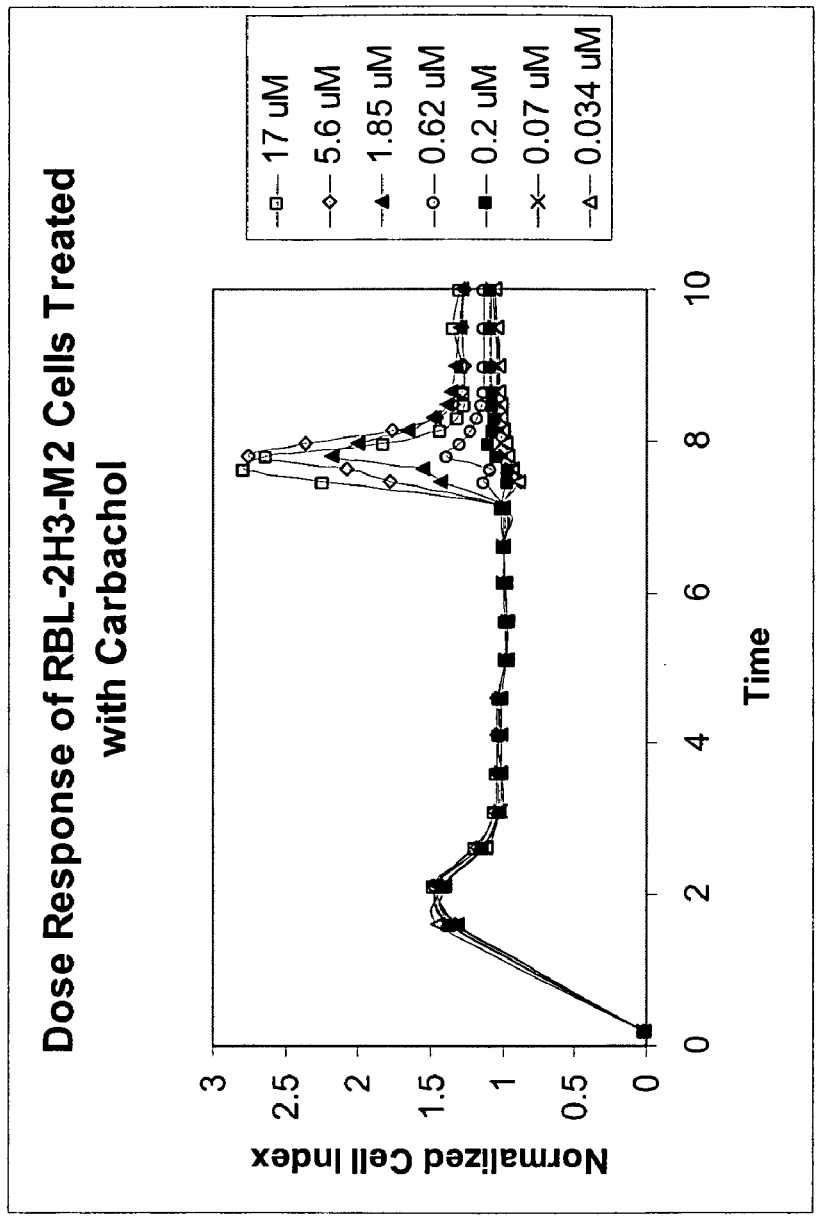
FIG. 12 shows real-time monitoring of the functional activation of G-protein-coupled muscarinic M2 (A) and M3 (B) receptors in RBL-2H3 cells using the RT-CES system. Real-time monitoring allows profiling and monitoring of receptor-specific responses.
Figure 12B:
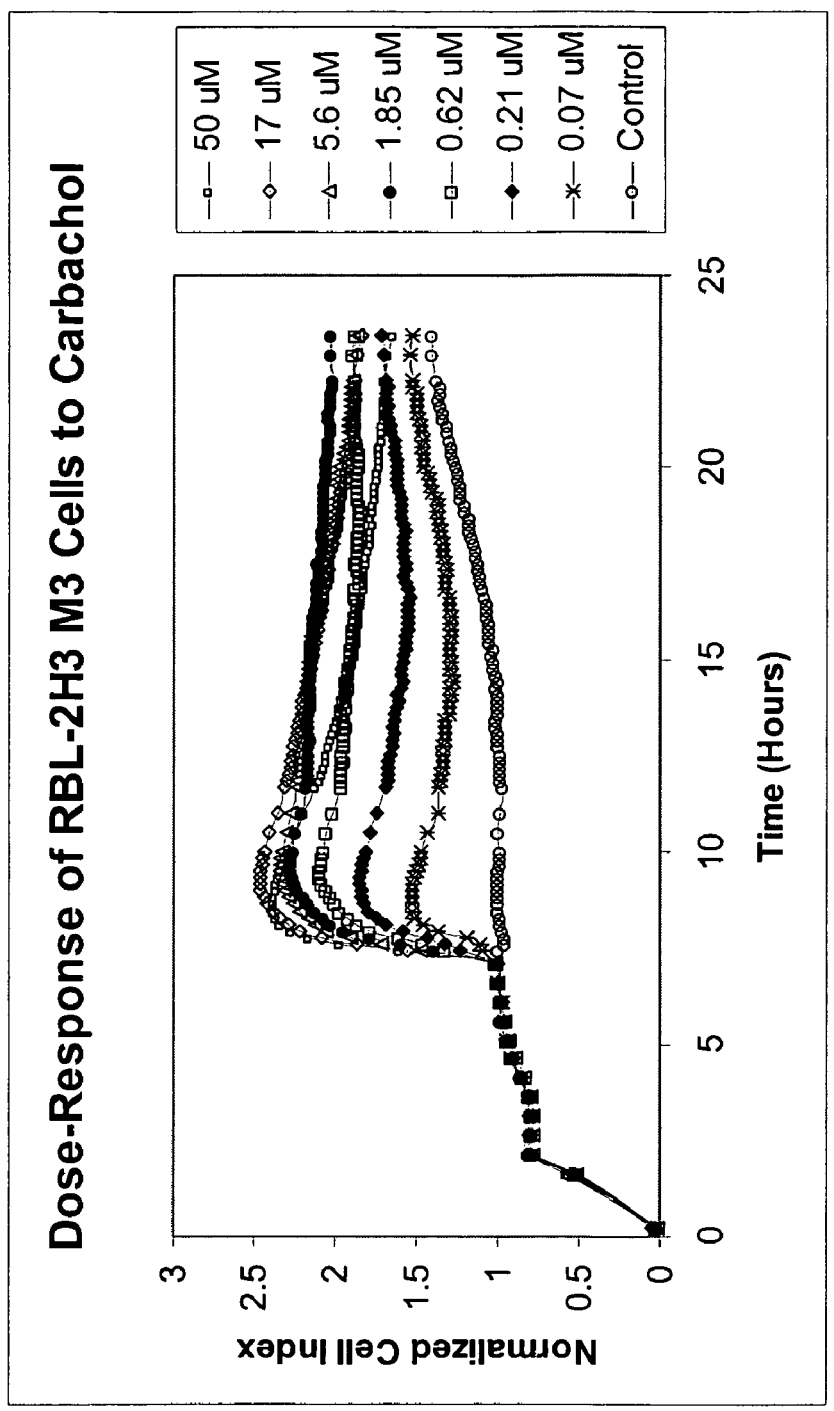

The RT-CES system allows for Real-time and continuous measurement, providing unprecedented kinetic information of the entire course of a cell-based assay process. Real-time monitoring can provide mechanistic insight into cell-based assays and is best exemplified by FIGS. 11 and 12. In the experiment represented in FIG. 10, cancer cells were seeded in ACEA electronic plates, allowed to reach growth phase, treated with different doses of an anti-mitotic compound while being continually monitored by the RT-CES system. Therefore, real-time monitoring offered by the RT-CES technology allows the user to determine when is the best time to perform a certain treatment and also provides a window into the compound's mechanism of action, which is lacking in traditional end-point cell-based assays In FIG. 12, RBL-2H3 cells expressing the muscarinic M2 and M3 receptors, seeded in ACEA electronic plates were treated with increasing doses of the agonist carbachol and continually monitored using the RT-CES system. The M2 (FIG. 12A) and M3 (FIG. 12B) muscarinic receptors, although activated by the same ligand are coupled to very different signaling pathways, which is evident by different kinetic responses obtained by the RT-CES system.

Therefore, real-time monitoring in combination with electronic-based sensing allows for functional monitoring of the receptors and provides pathway specific information.

What is claimed is:

1. A method of monitoring a cellular response in real time, comprising:
    a. monitoring at least one impedance measurement prior to transfecting a cell or cell population;
    b. determining said cell or cell population is to be transfected if said at least one impedance measurement prior to transfecting said cell or cell population is within a predetermined range;
    c. transfecting said cell or cell population with a molecule if determined to be transfected, wherein said cell or cell population is transfected using a method selected from the group consisting of a chemical transfection method, electroporation and a viral transfection method, further wherein said molecule is capable of affecting a cellular function selected from the group consisting of cell proliferation, cell adhesion and cell spreading; and
    d. monitoring impedance of said cell or said cell population when said cell or said cell population is attached to an impedance-monitoring electrode.

2. The method according to claim 1, wherein said cell is a eukaryotic cell.

3. The method according to claim 1, wherein said cell is a mammalian cell.

4. The method according to claim 1, wherein said molecule is selected from the group consisting of a DNA molecule, an RNA molecule, an oligopeptide, a polypeptide, a protein and a compound.

5. The method according to claim 4, wherein said DNA molecule is selected from the group consisting of a recombinant DNA molecule, a native DNA molecule, a plasmid, a cDNA, an anti-sense DNA strand and an oligonucleotide.

6. The method according to claim 4, wherein said RNA molecule is selected from the group consisting of a siRNA molecule, a microRNA molecule, a native RNA molecule, a ribozyme RNA and an aptamer.

7. The method according to claim 1, wherein said molecule is a capable of affecting a process selected from the group consisting of transcription, translation, RNA splicing and RNA editing.

8. The method according to claim 1, wherein said molecule is capable of affecting cell morphology.

9. The method according to claim 1, further comprising conducting an endpoint assay selected from the group consisting of a cell viability assay, an apoptosis assay, an enzymatic activity assay, a signal transduction analysis assay, and a reporter assay.

10. A method of monitoring a cellular response in real time, comprising:
    a. monitoring at least one impedance measurement prior to transfecting a cell or cell population;
    b. determining said cell or cell population is to be transfected if said at least one impedance measurement prior to transfecting said cell or cell population is within a predetermined range;
    c. transfecting said cell or cell population with a molecule if determined to be transfected, wherein said cell or cell population is transfected using a method selected from the group consisting of a chemical transfection method, electroporation and a viral transfection method, further wherein said molecule is capable of affecting a cellular receptor or a signal transduction pathway activated by said receptor; and d. monitoring impedance of said cell or said cell population when said cell or said cell population is attached to an impedance-monitoring electrode.

11. The method according to claim 10, further comprising conducting an endpoint assay selected from the group consisting of a cell viability assay, an apoptosis assay, an enzymatic activity assay, a signal transduction analysis assay, and a reporter assay.

12. The method according to claim 10, wherein said cell is a eukaryotic cell.

13. The method according to claim 10, wherein said cell is a mammalian cell.

14. The method according to claim 10, wherein said molecule is selected from the group consisting of a DNA molecule, an RNA molecule, an oligopeptide, a polypeptide, a protein and a compound.

15. The method according to claim 14, wherein said DNA molecule is selected from the group consisting of a recombinant DNA molecule, a native DNA molecule, a plasmid, a cDNA, an anti-sense DNA strand and an oligonucleotide.

16. The method according to claim 14, wherein said RNA molecule is selected from the group consisting of a siRNA molecule, a microRNA molecule, a native RNA molecule, a ribozyme RNA and an aptamer.

17. The method according to claim 10, wherein said molecule is a capable of affecting a process selected from the group consisting of transcription, translation, RNA splicing and RNA editing.

18. The method according to claim 10, wherein said molecule is capable of affecting cell morphology.

19. A method of monitoring a cellular response in real time, comprising:
   a. transfecting a cell or cell population with a molecule using electroporation, wherein said molecule is capable of affecting a cellular function selected from the group consisting of cell proliferation, cell adhesion, and cell spreading; and
   b. monitoring impedance of said cell or said cell population when said cell or said cell population is attached to an impedance-monitoring electrode.

20. The method according to claim 19, wherein said cell is a mammalian cell.

21. The method according to claim 19, wherein said molecule is selected from the group consisting of a DNA molecule, a RNA molecule and a polypeptide.

22. The method according to claim 21, wherein said DNA molecule is selected from the group consisting of a recombinant DNA molecule, a native DNA molecule, a plasmid, a cDNA, an anti-sense DNA strand and an oligonucleotide; and wherein said RNA molecule is selected from the group consisting of a siRNA molecule, a microRNA molecule, a native RNA molecule, a ribozyme RNA and an aptamer.

23. A method of monitoring a cellular response in real time, comprising:
   a. transfecting a cell or cell population with a molecule using electroporation, wherein said molecule is capable of affecting cell morphology; and
   b. monitoring impedance of said cell or said cell population when said cell or said cell population is attached to an impedance-monitoring electrode.

24. The method according to claim 23, wherein said cell is a mammalian cell.

25. The method according to claim 23, wherein said molecule is selected from the group consisting of a DNA molecule, a RNA molecule and a polypeptide.

26. The method according to claim 25, wherein said DNA molecule is selected from the group consisting of a recombinant DNA molecule, a native DNA molecule, a plasmid, a cDNA, an anti-sense DNA strand and an oligonucleotide; and wherein said RNA molecule is selected from the group consisting of a siRNA molecule, a microRNA molecule, a native RNA molecule, a ribozyme RNA and an aptamer.

27. A method of monitoring a cellular response in real time, comprising:
   a. transfecting a cell or cell population with a molecule using electroporation, wherein said molecule is capable of affecting a cellular receptor or a signal transduction pathway activated by said receptor; and
   b. monitoring impedance of said cell or said cell population when said cell or said cell population is attached to an impedance-monitoring electrode.

28. The method according to claim 27, wherein said cell is a mammalian cell.

29. The method according to claim 27, wherein said molecule is selected from the group consisting of a DNA molecule, a RNA molecule and a polypeptide.

30. The method according to claim 29, wherein said DNA molecule is selected from the group consisting of a recombinant DNA molecule, a native DNA molecule, a plasmid, a cDNA, an anti-sense DNA strand and an oligonucleotide; and wherein said RNA molecule is selected from the group consisting of a siRNA molecule, a microRNA molecule, a native RNA molecule, a ribozyme RNA and an aptamer.

* * * * *